(12) United States Patent
Jacobsen et al.

(10) Patent No.: US 6,489,093 B1
(45) Date of Patent: Dec. 3, 2002

(54) COMBINATORIAL APPROACH FOR GENERATING NOVEL COORDINATION COMPLEXES

(75) Inventors: Eric N. Jacobsen, Boston, MA (US); Matthew B. Francis, Somerville, MA (US); Nathaniel S. Finney, West Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 08/933,714

(22) Filed: Sep. 19, 1997

Related U.S. Application Data

(60) Provisional application No. 60/026,432, filed on Sep. 20, 1996.

(51) Int. Cl.[7] .............................. C12Q 1/00; G01N 33/20
(52) U.S. Cl. .................... 435/4; 435/7.1; 435/DIG. 14; 436/501; 436/518
(58) Field of Search .................... 435/47.1, DIG. 14; 436/501, 518

(56) References Cited

U.S. PATENT DOCUMENTS

| | | | |
|---|---|---|---|
| 5,637,684 A | | 6/1997 | Cook et al. |
| 5,639,603 A | | 6/1997 | Dower et al. |
| 5,665,865 A | | 9/1997 | Lerner et al. |
| 5,679,548 A | | 10/1997 | Barbas et al. |
| 5,698,391 A | | 12/1997 | Cook et al. |
| 5,717,083 A | | 2/1998 | Cook et al. |
| 5,840,485 A | * | 11/1998 | Lebl et al. ..................... 435/6 |
| 6,030,917 A | * | 2/2000 | Weinberg et al. ........... 502/104 |
| 6,107,059 A | * | 8/2000 | Hart .......................... 435/69.7 |

FOREIGN PATENT DOCUMENTS

| | | |
|---|---|---|
| WO | WO 98/03521 | 1/1998 |

OTHER PUBLICATIONS

Hwang et al., Materials Science and Engineering C3 vol. 2 pp. 137–141, 1995.*

Burgess, K, et al., "New Catalysts and Conditions for a C–H Insertion Reaction Identified by High Throughput Catalyst Screening**", *Angew Chem Int Ed. Engl.*, 35, No. 2, 1996.

Malin, R., et al., "Indentification of Technetium–99m Binding Peptides Using Combinatorial Cellulose–Bound Peptide Libraries", *J. Am. Chem. Soc.*, 117, pp. 11821–11822, 1995.

Burger, M., et al., "Synthetic Ionophores. Encoded Combinatorial Libraries of Cyclen–based Receptors for Cu2+ and Co2+", *J. Org. Chem.*, vol. 60, pp. 7382–7382, 1995.

Francis, M., et al., "Combinatorial Approach to the Discovery of Novel Coordination Complexes", *J. Am. Chem. Soc.*, vol. 118, pp. 8983–8984, 1996.

Goodman, M, Scott, et al., "A Combinatorial Library Approach to Artificial Receptor Design", *J. Am. Chem. Soc.*, vol. 117, pp. 11610–11611, 1995.

Horwitz, C., et al., "Ligand Design Approach for Securing Robust Oxidation Catalysts", *J. Am. Chem. Soc.*, vol. 120, pp. 4867–4868, 1998.

Jones, David G., "Applications Of Encoded Synthetic Libraries in Ligand Discovery", *Polym. Prep.*, vol. 35, pp. 981–982, 1994.

Lam, K.S., et al., "A New Type of Synthetic Peptide Library for Identifying Ligand– Binding Activity—Generation and Use of Synthetic Peptide Combinatorial Libraries for Basic Research and Drug Discovery", *Organic Chemistry*, vol. 5:71–72, 1992.

Reetz, T., et al., "Creation of Enantioselective Biocatalysts for Organic Chemistry by In Vitro Evolution", *Angew. Chem. Int. Ed. Engl.*, vol. 36, No. 24, 1997.

Torrado, A., et al., "Exploiting Polypeptide Motifs for the Design of Selective Cu(II) Ion Chemosensors", *J. Am. Chem. Soc.*, vol. 120, pp. 609–610, 1998.

* cited by examiner

*Primary Examiner*—Bennett Celsa
(74) *Attorney, Agent, or Firm*—Dana M. Gordon; Foley Hoag LLP

(57) ABSTRACT

The present invention provides methods and compositions, i.e. synthetic libraries of binding moities, for identifying compounds which bind to a metal atom or to non-metal ions, e.g., cationic or anionic molecules.

5 Claims, 35 Drawing Sheets

90 mm TentaGel S NH2

Position 1:
L- or D-Asp(OtBu)
L- or D-Ser(OtBu)
L- or D-Met
L- or D-Tyr(OtBu)
L- or D-Phg
L- His(Trt)
Gly

Position 2:
L-Asp(OtBu)   L-Phg
L-Ser(OtBu)   Gly
L-Tyr(OtBu)
L- His(Trt)
L-Met
L-Trp

6

Turn Element Monomers: (Ar=p-nitrophenyl)

1a: (1S.2S). n=1
1b: (1R.2R). n=1
2a: (1S.2S). n=2
2b: (1R.2R). n=2

3a: (1S.2R). n=1
3b: (1R.2S). n=1
4a: (1S.2R). n=2
4b: (1R.2S). n=2

5a: (2S). n=1
5b: (2R). n=2

End Cap Monomers:

7: R = CH3
8: R = tBu
9: R = 1-Naphthyl
10: R = CH2CO2CH3
11: R = 2-Pyridyl

12

<Blank>

16 R = CH₃
17 R = 1-naphthyl

- Amino acids provide structural and functional group diversity
- Turn element induces interactions between peptide chains
- Commercially available acylating reagents increase diversity
- Ligands encoded by established methods (W.C. Still et al. PNAS, 1993, 90, 10922).

| Structure | Linker | Amino Acid 1 | End Cap 1 | Amino Acid 2 | End Cap 2 |
|---|---|---|---|---|---|
| 1 | (R,S)-cis | His(Trt) | Bz | Pho | Bz |
| 2 | (R,S)-cis | His(Trt) | Bz | Trp | Bz |
| 3 | (R,S)-cis | His(Trt) | Bz | Pho | Bz |
| 4 | (R,S)-cis | His(Trt) | Bz | Pho | Bz |
| 5 | (R,S)-cis | His(Trt) | Bz | Thr(tBu) | Bz |
| 6 | (R,R)-trans | His(Trt) | Bz | Gly | Bz |
| 7 | (R,S)-cis | His(Trt) | Bz | Pho | Bz |
| 8 | (R,R)-trans | His(Trt) | Bz | Ile | Bz |
| 9 | (R,S)-cis | His(Trt) | Bz | Thr(tBu) | Bz |
| 10 | (R,R)-trans | His(Trt) | Bz | Asp(tBu) | Bz |
| 11 | (R,R)-trans | His(Trt) | Bz | Gly | Bz |
| 12 | (R,S)-cis | His(Trt) | Bz | His(Trt) | Bz |

| Structure | Linker | Amino Acid 1 | End Cap 1 | Amino Acid 2 | End Cap 2 |
|---|---|---|---|---|---|
| 1 | ? | His(Trt) | Piv | Asp(tBu) | Pip |
| 2 | ? | His(Trt)? | Pip | Leu | Piv |
| 3 | (R,S)-cis | His(Trt) | Piv | Asp(tBu) | Dmb |
| 4 | (S,R)-cis | His(Trt) | Piv | His(Trt) | Pip |
| 5 | (S,R)-cis | His(Trt) | Pip | Tyr(tBu) | Dmb |
| 6 | ? | His(Trt)? | Cin | Asp(tBu) | Acy |
| 7 | cis | His(Trt) | Cin | Gly | Acy |
| 8 | (S,R)-cis | His(Trt) | Dmb | Thr(tBu) | Dmb |
| 9 | ? | His(Trt) | Piv | Asp(tBu) | Acy |
| 10 | (S,R)-cis | His(Trt) | Piv | Asp(tBu) | Nap |
| 11 | cis | His(Trt) | Cin | Thr(tBu) | Pip |
| 12 | ? | Tyr(tBu) | Dmb | His(Trt) | Cyc |

FIG. 7A

| Structure | Amino Acid 1 | Turn Element | Amino Acid 2 | End Cap |
|---|---|---|---|---|
| 1 | D-Asp(OBu) | (R,S)-Nap | Iso | Mal |
| 2 | D-Ser(OBu) | (R,S)-Ind | Iso | Mal |
| 3 | D-Ser(OBu) | (S,R)-Ind | Iso | Mal |
| 4 | L-Tyr(OBu) | (R,R)-Chx | Iso | Mal |
| 5 | L-Tyr(OBu) | (S,R)-Nap | Iso | Mal |
| 6 | D-Tyr(OBu) | D-Pip | Iso | Mal |
| 7 | Gly | (R,R)-Cyp | Iso | Mal |
| 8 | L-Met | D-Pip | Iso | Mal |
| 9 | L-Met | D-Pip | Iso | Mal |
| 10 | L-Met | (R,S)-Nap | Iso | Mal |
| 11 | D-Met | (R,S)-Nap | Iso | Mal |
| 12 | D-Met | (R,S)-Nap | Iso | Mal |
| 13 | D-Met | (S,R)-Ind | Iso | Mal |
| 14 | D-Met | (S,S)-Cyp | Iso | Mal |

| | | | | | | | | | | | Al | | Ge |
|---|---|---|---|---|---|---|---|---|---|---|---|---|---|
| Sc | Ti | V | Cn | Mn | Fe | Co | Ni | Cn | Zn | Ga | | | |
| Y | Zr | Nb | Mo | Tc | Ru | Rn | Pd | Ag | Cd | In | | | Sn |
| Ln | Hf | Ta | W | Re | Os | Ir | Ph | Au | Hg | Tl | | | Pb |

▨ = Successfully Bound
▩ = Not Incorporated
☐ = Not Yet Tried

| Ce | Yo |
|---|---|

$Cu^{2+}$: Binds to 30% of the library
  Prefers His-His Structures
$Pd^{2+}$: Binds to 90% of the library
$Pt^{4+}$: Binds to 20% with a Met preference in Pos. 1
$Sn^{4+}$: Binds weakly to 50%, and more strongly to 10%

FIG. 10

COMBINATORIAL APPROACH FOR GENERATING NOVEL COORDINATION COMPLEXES

This application claims the benefit of Ser. No. 60/026,432, filed Sep. 9, 1996.

GOVERNMENT FUNDING

This invention was partially funded by NIH Grant No. GM136639 and the government has certain rights to the invention.

BACKGROUND OF THE INVENTION

Those skilled in the art are well aware of the technological importance of chelating agents for removing metal ions from various effluents, such as waste water, plating baths and the like. Chelating agents provide means of manipulating and controlling metal ions by forming complexes that usually have properties that are markedly different from those of the original metal ions or the chelators. These properties may serve to reduce undesirable effects of metal ions in drinking water, waste water, sewage and the like.

In this regard, many industries utilize heavy metals and/or rare earth metals in their manufacturing processes. Such use typically results in liquid (generally aqueous) waste streams that contain residues of the rare earth or heavy metals utilized in the given manufacturing process. For example, the waste stream resulting from electronics, electroplating and photographic processes typically contain metal ions such as copper, nickel, zinc, chromium, cadmium, aluminum, lead, antimony, silver and gold, amongst others in aqueous solutions accompanied by various anions such as sulfate, chloride, fluoroborate and cyanide. Because of the potential adverse effects of such metals on health and the environment, the removal of rare earth metals and heavy metal ions from aqueous waste streams is a problem of continuing significance. There is a growing need in the relatively new area of environmentally benign chemistry to design organic ligands in order to selectively remove and recover environmentally and economically important metal ions from aqueous solution.

Furthermore, the relationship of ligand structure to the chemical and physical properties of derived metal complexes is a central theme in such vital and disparate fields as selective catalysis, treatments for heavy metal poisoning, sensor discovery, and bioinorganic chemistry. The numerous advances made in these fields highlight the utility of complexes with well-designed structural, electronic and/or stereochemical features. However, the rational design of such complexes remains extremely challenging, especially if novel physical and chemical properties are sought. In this context, a systematic method for the expedient generation of new classes of coordination complexes would clearly be of great value.

SUMMARY OF THE INVENTION

The present invention provides methods and compositions, i.e. synthetic libraries of binding moities, for identifying compounds which bind to a metal atom. The subject method comprises (a) chemically synthesizing a variegated library of potential binding moieties ("PBMs"), and (b) screening the library of PBMs to isolate/identify those members that bind to a metal atom, or to non-metal atoms, e.g., cationic, anionic and even neutral molecules. Utilizing such combinatorial chemistry techniques as, e.g., direct characterization, encoding, spatially addressing and/or deconvolution, the molecular identity of individual members of the PBM library can be ascertained in a screening format.

Another aspect of the present invention pertains to kits for carrying of the instant method.

Still another aspect of the present invention provides compositions including one or more of the PBM compounds identified by the instant method.

BRIEF DESCRIPTION OF THE FIGURES

FIGS. 7A–D illustrate the composition of a PBM library generated with internal turn elements.

FIG. 10 is a partial periodic table indicating the various metals which could be coordinately bound by various PBMs provided in a single library.

DETAILED DESCRIPTION OF THE INVENTION

Figure 1:
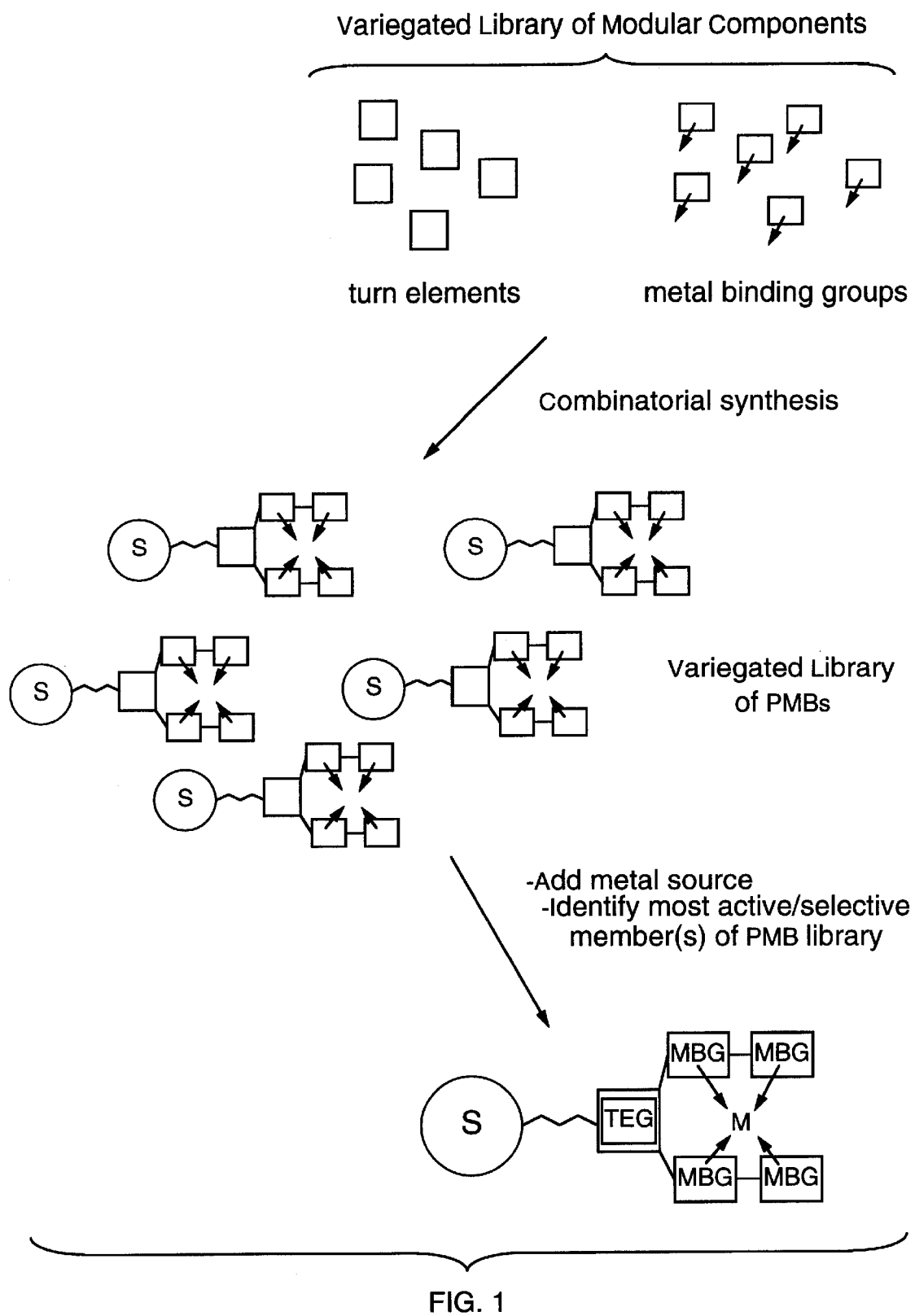
FIG. 1 depicts a general modular scheme used to construct a library of metal binding moieties. TEG=turn element group; MBG=metal binding group; and S=solid support.

The synthesis and screening of combinatorial libraries is a validated strategy for the identification and study of ligand-receptor interactions. For recent reviews on strategies for the synthesis of small-molecule libraries, see: Thompson et al. (1996) *Chem Rev.* 96:555; Armstrong et al. (1996) *Acc. Chem. Res.* 29:123; Gordon et al. (1994) *J. Med. Chem.* 37:1385. For combinatorial approaches to the study of ligand-receptor interactions, see Still et al. (1996) *Acc. Chem. Res.* 29:155, and references therein; Yu et al. (1994) *Cell* 76:933; Combs et al. (1996) *J. Am. Chem. Soc.* 118:287; Zuckermann et al. (1994) *J. Med. Chem.* 37:2678; Wang et al. (1995) *J. Med. Chem.* 38:2995; Campbell et al. (1995) *J. Am. Chem. Soc.* 117:5381. In this context, combinatorial systems have allowed many structural changes to be examined simultaneously, thus allowing an evaluation of, for example, synergistic effects in ligand binding. Since the stability and activity of metal complexes are similarly dependent on numerous interrelated variables, such as the coordination geometry required by the metal and the steric and electronic characteristics of the ligand, combinatorial chemistry could also provide a powerful approach for discovering new types of coordination compounds. For example, spatially addressed synthetic libraries have been applied with success for the identification of metal-containing solid-state materials (Briceño et al. (1995) *Science* 270:273), 99mTc-binding peptides (Malin et al. (1995) *J. Am. Chem. Soc.* 117:11821), and selective catalysts (Burgess et al. (1996) *Angew. Chem. Int. Ed. Engl.* 35:220).

The prior art teaches a strategy that may be adopted for the design of libraries of potential metal ion binders. Briefly, it involves attaching a variety of possible binding elements to a known ligand structure. In this context, Still and coworkers recently described the preparation of solid phase libraries containing cyclen units with short peptidic appendages. See Burger et al. (1995) *J. Org. Chem.* 60:7382; and Schimizu et al. (1997) *Anfewandte Chemie* 36:1704. Although cyclen is a known tetradentate ligand for metal ions such as Cu(II) and Co(II), these ions were found to bind with selectively imparted by the variable library elements.

I. Overview of the Subject Method

The method of the present invention is a fundamentally different approach to generating agents with metal binding activity through a modular combinatorial synthesis scheme. Rather than begin with predefined binding sites, the subject method involves the design of libraries of potential metal binding ligands from diverse sets of functional groups and conformational restrictions that can result in a range of potential coordination environments. As described below, we have demonstrated that the subject combinatorial libraries can be successfully applied to the identification of, for example, novel metal-ligand complexes. Moreover, the structural information thus obtained has revealed unanticipated and non-intuitive structural effects in binding selectivity and affinity.

In its most general embodiment, the process of the present method comprises: (a) chemical synthesis of a variegated library of potential binding moieties ("PBMs" or "ligands") from an assortment of functional groups and turn elements, and (b) screening the library of PBMs to isolate/identify those members that bind to a metal atom. Through the use of such techniques as, e.g., encoding, spatially addressing, mass spectroscopy and/or deconvolution, combinatorial libraries of PBMs can be synthesized by batch processes and, importantly, the molecular identity of individual members of the library can be ascertained in a screening format. It will be understood that once a library of PBMs is constructed, the library can be screened any number of times with a number of different metals or ions of choice.

Moreover, while for ease of reading the application will refer to metals as the preferred molecules against which the PBMs are screened, those skilled in the art will also appreciate that the subject method and libraries can be used to screen for PBMs which selectively bind to non-metal ions, e.g., cationic or anionic molecules. In still other embodiments, the subject PBM libraries can be used to generate new ligands for neutral molecules, e.g., which may bound by the PBM though, inter alia, molecular recognition (see, for example, Kinneary (1989) *Journal of Inclusion Phenomena and Molecular Recognition in Chemistry*, 7:155–168.

As described in greater detail below, there are a wide range of applications for the PBMs identified by the subject method. For example, since many metal complexes are highly colored, the coordination compounds identified in the present method can be used for dyes and pigments, as well as for calorimetric fluorometric reagents for detecting the presence of a metal. For instance, certain of the subject PBMs can be fluorescently active such that, e.g., fluorescence polarization of the PBM relates to metal ion concentration In other embodiments, as described below, the subject metal binding compounds can be generated according to the present method so as to be discriminatory towards certain metals. The selectivity of a PBM can be used to sequester specific metals (or non-metals as the case may be) from complex mixtures. For instance, such selectivity can be utilized in chelation therapy, e.g., when the metal to be sequestered is present in blood, or in bioremdiation, e.g., when the metal is present in water. In this regard, the subject PBMs can be used in complexometric determinations, e.g., for analyzing mixtures of metals.

In other embodiments, the present method can be used in the identification of useful chelating agents. Such PBMs can be selected from the library on the basis of binding to, e.g., a metal under certain conditions (pH, temperature, organic solvent, etc.) and/or based on the specificity of the PBM for a particular metal. In the instance of the latter, differential screening formats, e.g., screening the PBM library against two or more different metals, can allow the identification of PBMs in the library which selectively bind only a subset of those metals. The chelating agents of the present invention will include agents useful in selective extraction methods, bioremediation, as therapeutic agents, and as sensors for particular metals.

In still other embodiments, the present method can be utilized to create catalysts. In an exemplary embodiment, the subject method can be used to identify and/or optimize the metal binding core of organo-metallic catalysts. The resulting catalysts can be useful, inter alia, in all aspects of chemical synthesis. In an exemplary embodiment, the PBMs selected from the library can be used to generate stereoselective catalysts such as the salens epoxidation catalysts described in, for example, U.S. Pat. No. 5,665,890, or the asymmetric catalysts-useful for the stereoselective allylsilylation of aldehydes of Example 8.

In general, the modular components are selected to provide PBMs capable of binding to the ligand of choice. The selection of appropriate PBMs will depend upon such factors as the target to be bound, the chemical stability of the modular components and of the PBMs, the selectivity of the desired ligand for a target (e.g., the ability to discriminate between similar targets), the desired stability of the ligand-target complex, and other factors known to those skilled in the art. For example, ligands for binding metal ions will generally include functional groups capable of interaction with a metal center, e.g., heteroatoms such as nitrogen, oxygen, sulfur, and phosphorus. Thus, for example, modular components for metal-binding PBMs will generally include heteroatoms capable of associating with a metal center. It will be understood that modular components can include sidechains or other pendant groups capable of interaction with a ligand, if desired.

Ligands preferably have more than one contact point with a target. For example, the metal-binding ligands of the invention preferably are capable of chelation to at least one metal ion. Chelation is at least bidentate and, in preferred embodiments, is tridentate, tetradentate, pentadentate, or hexadentate. For ligands capable of spatial recognition, e.g., discrimination of diastereomer or enantiomer, at least three contact points between the ligand and the target will generally be required.

In preferred embodiments, PBMs are synthesized, and ligands selected, to provide a pre-determined degree of selectivity for a chosen target. Thus, for example, in certain embodiments, metal-binding ligands are capable of discriminating among metal ions, e.g., binding to a metal such as copper, while substantially not binding to a metal such as iron. High selectivity can be attained by appropriate choice of modular components for construction of a library of PBMs. Thus, ligands can be synthesized and selected which are highly selective for only a single target, e.g., metal ion, in a mixture of potential targets.

In preferred embodiments, the PBM library includes at least $10^2$, more preferably $10^3$, $10^4$, $10^5$, $10^6$ or even $10^7$ different PBMs in the library as a whole. The library may, as appropriate, include potential bidentate, tridentate, tetradentate and/or even higher order metal-chelating ligands. Preferably each PBM, without any linker chemistry for immobilization, has a molecular less than 7500 amu, more preferably less than 5000, 2500 or even 1000 amu, and even more preferably less than 500 or even 250 amu.

The PBM can be a metal chelator which is preferably selected to be a bidentate, tridentate, or tetradentate chelating agents. In embodiments wherein the subject PBMs are intended for use as, for example, components of metal catalysts, the PBM is selected in conjunction with the metal ion so that when the chelating agent coordinates the metal ion, at least two free coordination sites remain on the metal. The chelating agent and metal are selected so that the chelating agent can coordinate the metal ion with a degree of stability great enough that the metal ion will remain sequestered by the chelating agent.

The metal atom is preferably selected from those that have at least four coordination sites, preferably six coordination sites. In preferred embodiments, the subject method can be used to identify ligands for any transition metal (e.g., having d electrons), e.g., a metal selected from one of Groups 3–12 of the periodic table or from the lanthanide series. A non-limiting list of metal ions for which PBMs of the present invention can be selected for binding includes $Co^{3+}$, $Cr^{3+}$, $Hg^{2+}$, $Pd^{2+}$, $Pt^{2+}$, $Pd^{4+}$, $Pt^{4+}$, $Rh^{3+}$, $Ir^{3+}$, $Ru^{3+}$, $Co^{2+}$, $Ni^{2+}$, $Cu^{2+}$, $Zn^{2+}$, $Cd^{2+}$, $Pb^{2+}$, $Mn^{2+}$, $Fe^{3+}$, $Fe^{2+}$, $Au^{3+}$, $Au^+$, $Ag^+$, $Cu^+$, $MoO_2^{2+}$, $Ti^{3+}$, $Ti^{4+}$, $Bi^{3+}$, $CH_3Hg^+$, $Al^{3+}$, $Ga^{3+}$, $Ce^{3+}$, $UO_2^{2+}$, $Yb^{3+}$ and $La^{3+}$.

II. Definitions

For convenience, certain terms employed in the specification and appended claims are collected here.

The terms "Lewis base" and "Lewis basic" are recognized in the art, and refer to a chemical moiety capable of donating a pair of electrons under certain reaction conditions. Examples of Lewis basic moities include uncharged compounds such as alcohols, thiols, and amines, and charged moieties such as alkoxides, thiolates, carbanions, and a variety of other organic anions.

The terms "Lewis acid" and "Lewis acidic" are art-recognized and refer to chemical moieties which can accept a pair of electrons from a Lewis base as defined above.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, J. March, *Advanced Organic Chemistry*, McGraw Hill Book Company, New York, (1977 edition) pp. 251–259. The Hammett constant values are generally negative for electron donating groups (σ[P]=−0.66 for $NH_2$) and positive for electron withdrawing groups (σ[P]=0.78 for a nitro group), (σ[P] indicating para substitution. Exemplary electron-withdrawing groups include nitro, ketone, aldehyde, sulfonyl, trifluoromethyl, —CN, chloride, and the like. Exemplary electron-donating groups include amino, methoxy, and the like.

The term, "chelating agent" refers to an organic molecule having unshared electron pairs available for donation to a metal ion. The metal ion is in this way coordinated by the chelating agent.

The terms, "bidentate chelating agent", "tridentate chelating agent", and "tetradentate chelating agent" refer to chelating agents having, respectively, two, three, and four electron pairs readily available for simultaneous donation to a metal ion coordinated by the chelating agent.

The term "coordination" refers to an interaction in which one multi-electron pair donor coordinatively bonds (is "coordinated") to one metal ion.

The term "coordinate bond" refers to an interaction between an electron pair donor and a coordination site on a metal ion leading to an attractive force between the electron pair donor and the metal ion.

The term "coordination site" refers to a point on a metal ion that can accept an electron pair donated, for example, by a chelating agent.

The term "free coordination site" refers to a coordination site on a metal ion that is occupied by a water molecule or other species that is weakly donating relative to a polyamino acid tag, such as a histidine tag.

The term "coordination number" refers to the number of coordination sites on a metal ion that are available for accepting an electron pair.

The term "complex" as used herein and in the claims means a coordination compound formed by the union of one or more electron-rich and electron-poor molecules or atoms capable of independent existence with one or more electronically poor molecules or atoms, each of which is also capable of independent existence.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms "heterocyclyl" or "heterocyclic group" refer to 3- to 12-membered ring structures, more preferably 3- to 7-membered rings, whose ring structures include one to four heteroatoms. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. Preferred heteroatoms are nitrogen, oxygen, sulfur and phosphorous.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art recognized and refer to both unsubstituted and substituted amines, e.g., a moiety that can be represented by the general formula:

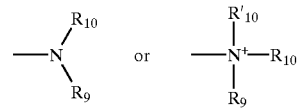

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

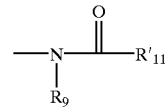

wherein R9 is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

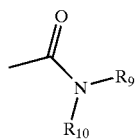

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

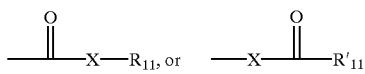

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formyl" group. In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

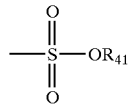

in which $R_{41}$ is an electron pair, hydrogen, alkyl cycloalkyl, or aryl.

The term "sulfate" is art recognized and includes a moiety that can be represented by the general formula:

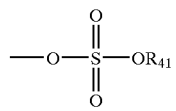

in which $R_{41}$ is as defined above.

The term "sulfonamido" is art recognized and includes a moiety that can be represented by the general formula:

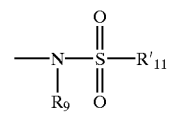

in which $R_9$ and $R'_{11}$ are as defined above.

The term "sulfamoyl" is art-recognized and includes a moiety that can be represented by the general formula:

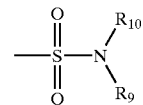

in which $R_9$ and $R_{10}$ are as defined above.

The terms "sulfoxido" or "sulfinyl", as used herein, refers to a moiety that can be represented by the general formula:

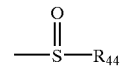

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

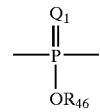

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

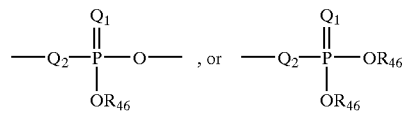

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" can be represented in the general formula:

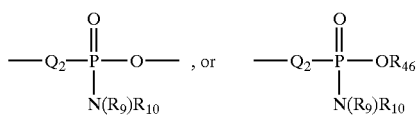

wherein $R_9$ and $R_{10}$ are as defined above, and $Q_2$ represents O, S or N.

A "phosphonamidite" can be represented in the general formula:

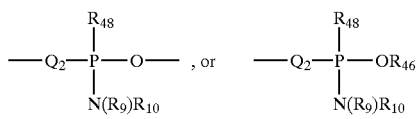

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The phrase "protecting group" as used herein means substituents which protect the reactive functional group from undesirable chemical reactions. Examples of such protecting groups include esters of carboxylic acids, ethers of alcohols and acetals and ketals of aldehydes and ketones.

In the context of this invention, a "saccharide" refers to any monosaccharide or oligosaccharide. A "monosaccharide" is a saccharide that is not hydrolyzable into smaller saccharide units. Monosaccharides include unsubstituted, non-hydrolyzable saccharides such as glucose, as well as modified saccharides in which one or more hydroxyl groups contain substitutions or have been replaced with hydrogen atoms (i.e., deoxy, dideoxy and trideoxy saccharides). Aza-sugars are another example of a modified monosaccharide. Alternatively, a monosaccharide may be present within an oligosaccharide. "Oligosaccharides" are hydrolyzable saccharides that contain two or more monosaccharides linked together in a linear or branched manner. Preferred oligosaccharides for use as turn elements in the subject invention are disaccharide and trisaccharide.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The term "immobilized", used with respect to a species, refers to a condition in which the species is attached to a surface with an attractive force stronger than attractive forces that are present in the intended environment of use of the surface, and that act on the species. For example, a chelating agent immobilized at a surface, the surface being used to capture a biological molecule from a fluid medium, is attracted to the surface with a force stronger than forces acting on the chelating agent in the fluid medium, for example solvating and turbulent forces.

The term "solid support" refers to a material which is an insoluble matrix, and may (optionally) have a rigid or semi-rigid surface. Such materials will preferably take the form of small beads, pellets, disks, chips, dishes, multi-well plates, wafers or the like, although other forms may be used. In some embodiments, at least one surface of the substrate will be substantially flat. The term "surface" refers to any generally two-dimensional structure on a solid substrate and may have steps, ridges, kinks, terraces, and the like without ceasing to be a surface.

The term "polymeric support", as used herein, refers to a soluble or insoluble polymer to which an amino acid or other chemical moiety can be covalently bonded by reaction with a functional group of the polymeric support. Many suitable polymeric supports are known, and include soluble polymers such as polyethylene glycols or polyvinyl alcohols, as well as insoluble polymers such as polystyrene resins. A suitable polymeric support includes functional groups such as those described below. A polymeric support is termed "soluble" if a polymer, or a polymer-supported compound, is soluble under the conditions employed. However, in general, a soluble polymer can be rendered insoluble under defined conditions. Accordingly, a polymeric support can be soluble under certain conditions and insoluble under other conditions.

The term "functional group of a polymeric support", as used herein, refers to a chemical moiety of a polymeric support that can react with an chemical moiety to form a polymer-supported amino ester. Exemplary functional groups of a polymeric support include hydroxyl and sulfhydryl, and the like. Preferred functional groups of a polymeric support will form polymer-supported amino esters that are covalently bound to the polymeric support under mild conditions that do not adversely affect the polymer or the amino ester, and that are sufficiently stable to be isolated.

The term "synthetic" refers to production by in vitro chemical or enzymatic synthesis.

The phrases "individually selective manner" and "individually selective binding", with respect to binding of a metal atom or other ion with a PBM, refers to the binding of the metal to a certain PBM which binding is specific for, and dependent on, the molecular identity of the PBM.

The term "meso compound" is recognized in the art and means a chemical compound which has at least two chiral centers but is achiral due to a plane or point of symmetry.

The term "chiral" refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" refers to molecules, e.g., saccharides, with identical chemical constitution and containing more than one stereocenter, but which differ in configuration at only one of these stereocenters.

The term "anomers" refers to saccharides that differ in configuration only at the anomeric carbon.

III. Description of Ligand Libraries

In general, the invention contemplates the use of modular components, also referred to herein as "monomeric subunits" or "subunits", to construct a library of potential binding moieties, e.g., for chelating metal or non-metal ions. The modular components are preferably molecular units which can be combined, such as through simultaneous or sequential coupling steps, to construct more complex compounds capable of binding to metal atoms or ions. Such modular components can be non-covalently associated, but are preferably covalently linked to one another, e.g., through linkages including, but not limited to, amide, ester, thioester, carbamate, carbonate, disulfide, hydrazido, phosphoester, and the like. Conveniently, modular components can be selected to facilitate PBM synthesis, e.g., modular components are selected so that coupling of each of the components can be performed according to well-understood techniques such as amino acid coupling or ester bond formation.

In one embodiment, illustrated in FIG. 1, the modular components of the subject method include at least two different classes of monomeric chemical moieties. The first group of monomers (or subunits) are referred to herein as "Metal Binding Groups" or "MBGs", and include compounds having one or more functional groups capable of binding a metal atom or ion. The second group of monomers are the "Turn Element Groups" or "TEGs". These units serve as branching points for disposing two or more MBGs in space. In general, the turn elements will be compounds with defined relative and absolute stereochemistry, and are introduced with the notion that such conformational restriction can encourage the formation of a potential binding site in which one or more metal binding functionalities of the MBGs interact with a metal. That is, the turn element arranges the functional groups of the attached MBGs in space with potential conformations that permit the resulting molecule to multiply coordinate a metal atom or ion.

A third, though optional group of monomeric subunits are the "spacers elements" (not shown in FIG. 1). These compounds are not intended to contain any functional groups which may interact to any great degree with a metal, ion, rather they are incorporated in the PBMs merely to alter the spacial arrangement of functional groups provided by the MBGs. That is, the spacer elements provide greater steric and/or stereochemical diversity in the PBM library.

The libraries can also include "end cap" elements and linkers, which may or may not effect the ability of functional groups on the MBGs to bind to a metal or ion. In certain embodiments, the selection of end cap elements can be motivated, at least in part, by such factors as an elements ability to protect MBG substituents, to enhance solubility under certain conditions, and/or to provide certain steric environments around a metal-binding center formed by MBGs.

As illustrated by FIG. 1, a library of PBMs is generated by the combinatorial coupling of at least one or more turn elements with metal binding groups. Diversity can be generated in the library in any of a number of ways. The PBM library can be generated from a variegated population of MBGs. For instance, the MBGs can introduce variation into the library due to the presence in these compounds of different functional groups, as well as differences in the locations (positions of attachment) and dispositions of these functional groups in the MBG structure, e.g., differences arising from chemical and steric features and/or stereochemistry of the MBG. To illustrate, where the MBGs of the library include amino acids, the PMB library can be generated with different amino acids, e.g., aspartic acid, glutamic acid, histidine, cysteine, methionine or tyrosine, etc., as well using different isomers of a given amino acid, e.g., L and D isomers.

Heterogeneity in the PBM library can also be introduced by the use of variegated populations of turn elements. As detailed below, the TEG subunits used in the combinatorial synthesis which constitute the generation of the library can be compounds of different chemical make-up and/or of different stereochemistries. For instance, a library of PMBs can be generated from a mixture of different cyclic alcohols and amines (see Example 1) as turn elements, e.g., substituted pyrrolidines, indanes, etc.

Figure 3A:
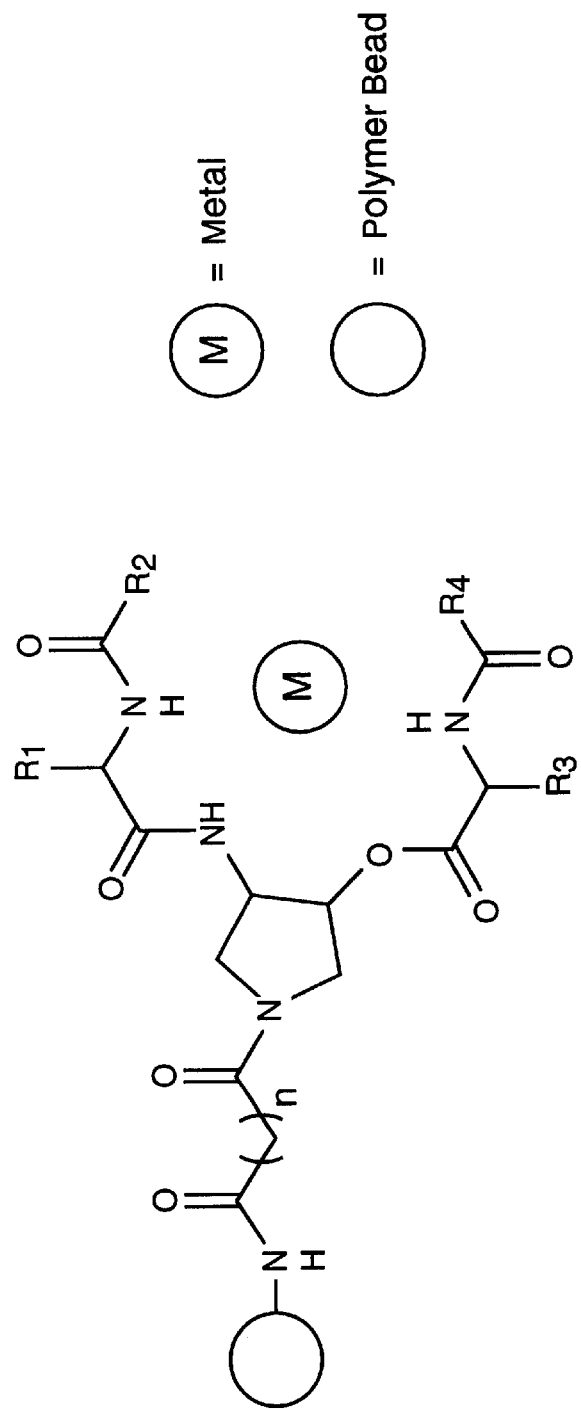
FIGS. 3A–B depict an exemplary turn-element which can be designed to introduce stereodiversity into the PBM library by exploiting chiral turn elements.
Figure 3B:
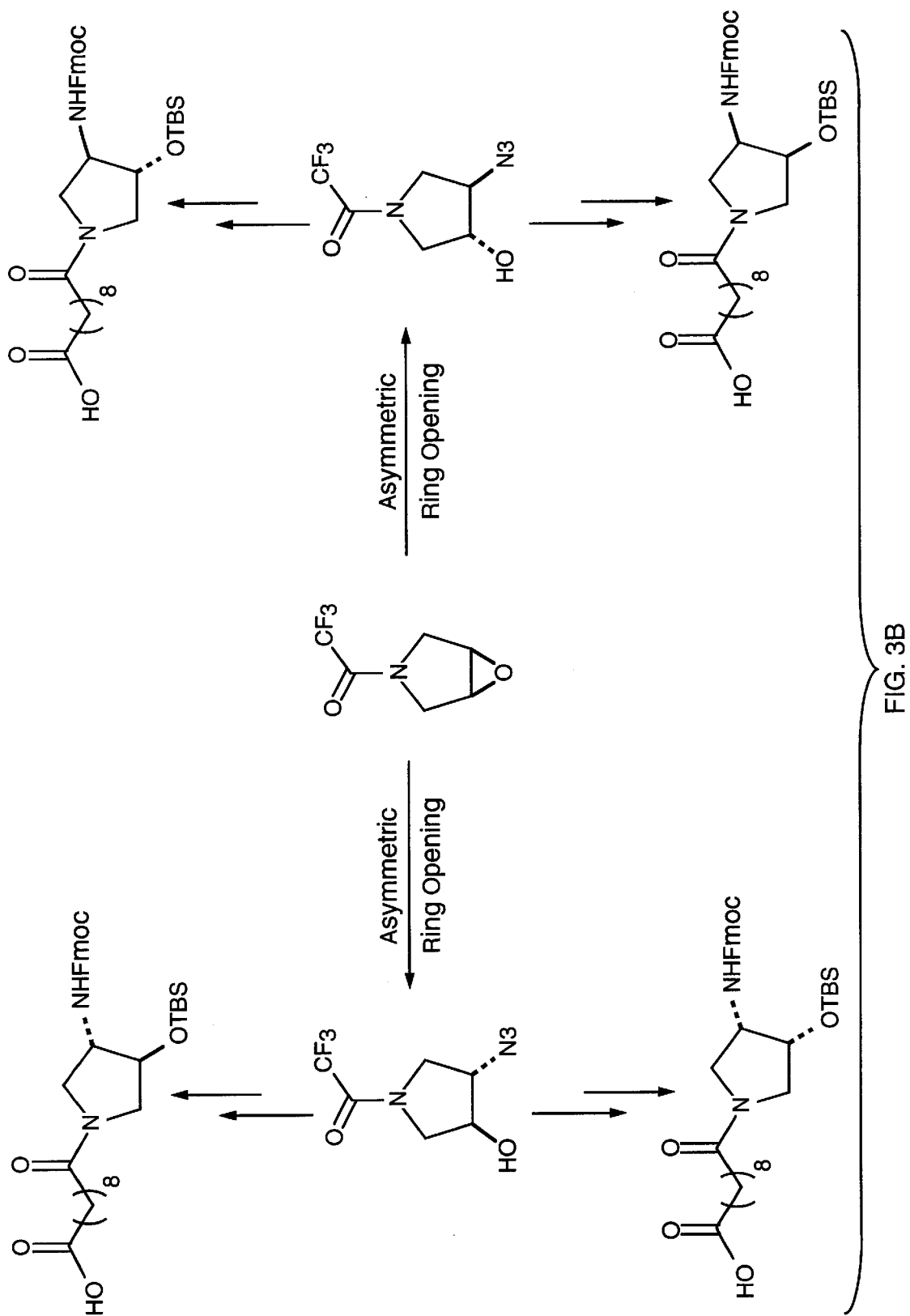

The stereochemistry of the turn element can also be used to variegate the PBM library, such as by the inclusion of different steroisomers of the same compound, e.g., resulting in diastereomeric, enantiomeric and/or regioisomeric diversity in the turn element. For example, FIGS. 3A and 3B illustrate the generation of (3R,4R), (3S,3R), (3S,4S) and (3R,4S) isomers of substituted 4-aminotetrahydro-3-pyrrolol-derived turn elements. As shown in FIG. 3B, the meso epoxide tetrahydro-1-aH-oxireno[2,3-c]pyrrole can be reacted with a nucleophile, e.g., trimethylsilyl azide (TMS-$N_3$), in the presence of a chiral catalyst to produce an enantiomeric pair of 4-azido-3-pyrrolidinols, which can in turn be used to generate the diasteromeric pairs bearing a t-butyldimethylsilyl ether (OTBS) protecting group.

Yet another means for introducing diversity into the PBM library, as indicated above, is through the use of spacer elements. Spacer elements are compounds which provide variability in the library with respect to relative distance and/or orientation of the functional groups of MBGs. For example, the spacer element can be alkyl chains of varying lengths. It will be understood that the role of a spacer element can also be effectively replaced by the choices for the MBGs subunits.

Thus, in an illustrative embodiment where the PBMs of a given library have one turn element position, the members of the library can be represented by the general formula $T(-R)_n$ where T represents a turn element, n is the number of substituted branch points on the turn element (e.g., an integer greater than or equal to 2) and R represents, independently for each of its n occurrences, a ligand sidechain comprising one or more metal binding moities. The number of different PBMs which can be provided in such a library is given by the formula $TE \times [Z_1 \times Z_2 \times \ldots Z_m]_1 \times [Z_1 \times Z_2 \times \ldots Z_m]_2 \times \ldots [Z_1 \times Z_2 \times \ldots Z_m]_n$, where TE is the number of turn element groups, and each Z is the number of MBGs (or other diversomer) at each of m combinatorial positions in each of the n ligand sidechains branching from the turn element. The number of diversomers at any given position in the PBM, be it a turn element or in a ligand sidechain, is the sum of different chemical moieties and/or stereoisomers which can occur at that position. In preferred embodiments, the PBM library includes at least 100 different molecular species, more preferably at least $10^3$, $10^4$ or $10^5$ different species of PBM, though libraries with the range of conventional combinatorial synthesis techniques are anticipated, e.g., exceeding $10^{13}$ distinct members.

Another aspect of the present invention relates to the generation of non-polymeric PBMs, e.g., which may be considered "non-modular" in structure. Exemplary PBMs of this class include salens, porphyrins, crown ethers, azacrown ethers, cyclams, phthalocyanines, and the like.

a). Metal Binding Groups

The role of the metal binding groups is to provide functional moieties in the PBM structure that can coordinate a metal atom in a chelate-type bonding arrangement. That is, the combinatorial synthesis of PBMs from metal binding monomers is intended to provide poly-functionalized ligands. In general, the MBGs will include organic electron donor moieties. Large metal cations that necessarily (by definition) are Lewis acidic are able to bind various Lewis basic entities, including those that are negatively charged. Accordingly, in a preferred embodiment, the subject libraries are generated with MBGs including one or more functional groups having an electron pair donor (Lewis base) capable of coordination with the transition metal. In general, the functional group will be a strongly acidic group, e.g., with a pKa less than about 7, and more preferably less than 5, which can produce a conjugate base that, under the reaction conditions, is a strong enough Lewis base to donate an electron pair to a metal atom to form a coordinate bond with the cationic form of the metal. However, the degree of this Lewis acid-to-Lewis base interaction is a function not only of the particular metal center coordinated to a functional group, but also of the Lewis base itself, since the latter could vary in the degree of basicity as well as in size and steric accessibility.

As set out above, the term "Lewis base" refers to any chemical species which is an electron pair donor. Two-electron Lewis bases are those bases which may donate a single pair of electrons. The types of Lewis base functional groups capable of forming coordinate complexes with metal ions are too numerous to categorize, though in preferred embodiments such compounds will include bases which bear atoms from Periodic Groups 15 and 16.

Lewis bases from Group 15 contain nitrogen, phosphorous, arsenic, antimony or bismuth atoms as electron pair donors. Preferable Lewis bases from Group 15 contain nitrogen, phosphorous, and antimony, and more preferably, nitrogen or phosphorous.

Lewis bases from Group 16 contain oxygen, sulfur, or selenium atoms as electron pair donors. Preferable Lewis bases from Group 16 contain oxygen or sulfur.

Exemplary Lewis basic moieties which can be used in the MBGs include amines (primary, secondary, and tertiary) and aromatic amines, amino groups, amido groups, nitro groups, nitroso groups, amino alcohols, nitrites, imino groups, isonitriles, cyanates, isocynates, phosphates, phosphonates, phosphites, (substituted) phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls and sulfinyls.

Illustrative of suitable MBGs are those organic compounds containing at least one Lewis basic nitrogen, sulfur, phosphorous or oxygen atom or a combination of such nitrogen, sulfur, phosphorous and oxygen atoms. The carbon atoms of the MBGs can be part of an aliphatic, cycloaliphatic or aromatic moiety. Typically, the MBG will contain at least 2 carbon atoms, though generally no more than 40 carbon atoms. In addition to the organic Lewis base(s), the MBG may also contain other atoms and/or groups as substituents, such as alkyl, aryl and halogen substituents. Metal Binding Groups useful as in generating PBMs in the subject method include linear and branched functional olefinic compounds having at least one functional terminal reactive group which can act as a Lewis base. Examples of the Lewis base are: amines, particularly alkylamines and arylamines, including methylamine, diphenylamine, trimethylamine, triethylamine, N,N-dimethylaniline, methyldiphenylaniline, pyridine, aniline, morpholine, N-methylmorpholine, pyrrolidine, N-methylpyrrolidine, piperidine, N-methylpiperidine, cyclohexylamine, n-butylamine, dimethyloxazoline, imidazole, N-methylimidazole, N,N-dimethylethanolamine, N,N-diethylethanolimine, N,N-dipropylethanolamine, N,N-dibutylethanolamine, N,N-dimethylisopropanolamine, N,N-diethylisopropanolamine, N,N-dipropylisopropanolamine, N,N-dibutylisopropanolamine, N-methyldiethanolamine, N-ethyldiethanolamine, N-propyldiethanolamine, N-butyldiethanolamine, N-methyldiisopropanolamine, N-ethyldiisopropanolamine, N-propyldiisopropanolamine, N-butyldiisopropanolamine, triethylamine, triisopropanolamine, tri-s-butanolamine and the like; amides, such as N,N-dimethylformamide, N,N-dimethylacetamide, N-methylpyrrolidone, hexamethylphosphoric acid triamide and the like; sulfoxide compounds, such as dimethylsulfoxide and the like; ethers such as dimethyl ether, diethyl ether, tetrahydrofuran, dioxane and the like; thioethers such as dimethylsulfide, diethyl thioether, tetrahydrothiophene and the like; esters of phosphoric acid, such as trimethyl phosphate, triethylphosphate, tributyl phosphate and the like; esters of boric acid, such as trimethyl borate and the like; esters of carboxylic acids, such as ethyl acetate, butyl acetate, ethyl benzoate and the like; esters of carbonic acid, such as ethylene carbonate and the like; phosphines, including di- and trialkylphosphines, such as tributylphosphine, triethylphosphine, triphenylphosphine, diphenylphosphine and the like; and monohydroxylic and polyhydroxylicalcohols of from 1 to 30 carbon atoms such as methyl alcohol, ethyl alcohol, n-propyl alcohol, isopropyl alcohol, n-butyl alcohol, isobutyl alcohol, tert-butyl alcohol, n-pentyl alcohol, isopentyl alcohol, 2-methyl-1-butyl alcohol, 2-methyl-2-butyl alcohol, n-hexyl alcohol, n-heptyl alcohol, n-octyl alcohol, isooctyl alcohol, 2-ethylhexyl alcohol, n-nonyl alcohol, n-decyl alcohol, 1,5-pentanediol, 1,6-hexanediol, allyl alcohol, crotyl alcohol, 3-hexene-1-ol, citronellol, cyclopentanol, cyclohexanol, salicyl alcohol, benzyl alcohol, phenethyl alcohol, cinnamyl alcohol, and the like.

Because the Lewis basic groups function as the coordination site or sites for the metal cation, it may be preferable that the deformability of the electron shells of the Lewis basic groups and the metal cations be approximately similar in order to provide selectivity to the PBM. For instance, sulfur groups may be desirable as the Lewis basic groups when the metal cations are transition metals or inner transition elements. Especially preferred Lewis basic groups for transition elements and the heavy metals are those containing sulfur. Especially preferred are oligopeptides such as glutathione and cysteine, mercapto ethanol amine, dithiothreitol, amines and peptides containing sulfur and the like Nitrogen containing groups are preferably employed as the Lewis basic groups when aluminum, lithium, boron, strontium, magnesium, and other small atomic diameter cations function as the metal.

In one arrangement, the collection of MBGs in any given ligand create a polyanionic surface that binds to a metal cation. However, a neutral Lewis base, such as an ether or amine compound, may also be associated with the complex, however, such is generally not preferred.

In yet other embodiments, the functional group can be be an aryl group, alkenyl group, alkynyl group or other moiety which may bind the metal atom in either a π- or σ-coordinated fashion.

As a further illustration, exemplary MBGs include bifunctional compounds such as amino acids, hydroxy acids, hydroxy thiols, mercapto amines, and the like. The term "amino acid" is intended to embrace all compounds, whether natural or synthetic, which include both an amino functionality and an acid functionality, including amino acid analogs and derivatives. Also included in the term "amino acid" are amino acid mimetics such as β-cyanoalanine, norleucine, 3-phosphoserine, homoserine, dihydroxyphenylalanine, 5-hydroxytryptophan, and the like. Such MBGs can include any and/or all stereoisomers when the modular component admits of such isomers.

Other exemplary modular components include nucleic acids and nucleic acid analogs and derivatives, diacids, diamines, and the like. In certain embodiments, modular components of different types can be combined to form a library of PBMs. For example, a diacid modular component can react with a diamine modular component to produce an amide bond.

In certain preferred embodiments, if the MBGs used to construct a variegated PBM library are amino acids, at least one modular component will be a non-naturally-occurring amino acid. In more preferred embodiments, if all the MBGs are amino acids, at least one MBG of each PBM of the library will include at least one non-naturally-occurring amino acid. Similarly, if all the MBGs used to generate the library are nucleic acids, at least one MBG of each PBM of the library preferably includes at least one non-naturally-occurring nucleic acid.

The process of selecting suitable non-natural amino acids for use in the present invention will parallel the selection of natural amino acids in the invention. For example, preferred embodiments of the natural amino acids identified above include nitrogen or sulfur atoms which bind directly to the metal center, e.g., histidine and cysteine. Similarly, preferred non-natural amino acids will also incorporate a nitrogen and/or a sulfur center for binding to the bridging metal ion.

If desired, one functionality can be selectively protected or blocked to permit reaction of an unblocked functional group. Thus, for example, amino acid MBGs can be blocked and deblocked according to known procedures for selective peptide synthesis. After addition of all MBGs is complete, the PBMs can be modified, e.g., capped or blocked to prevent further reaction.

The metal binding group components can be selected for a particular function when incorporated into libraries of PBMs. For example, the metal-binding libraries described infra are constructed from amino acid modular components. In this illustrative embodiment, one modular component is chosen to be a turn element, which, by restricting the flexibility of the PBM backbone, confers upon each PBM a conformation which may be better suited to metal binding than a linear conformation. Thus, any or all of the modular components can be selected to impart a particular function to the PBMs of a library.

b). Turn Elements

A metal imposes on the ligands coordinated to it a defined geometry dependent on its electronic structure. In this way, a metal ion in a metallo-complex with a PBM can determine the tertiary structure of the PBM, which in turn determines the affinity and specificity of the PBM for the metal. An important feature of chelating ligands is the bite angle, which determines the degree of strain in the complex, and its distortion from ideal geometry vis-a-vis the metal's coordination sphere. Moreover, nonsteric effects from the MBGs and spacers can lead to distorted or unusual geometries in the complex. The binding affinity and specificity of a chelating ligand, e.g., a PBM of the present invention, is therefore influenced by the ability of its metal binding groups to access certain coordination space. A salient feature of the turn elements of the subject PBMs is that they can provide the spatial preorganization of the metal binding groups into conformations which can be complementary to the coordination geometries of a metal ion, as in a combinatorial approach, optimize metal binding affinity and/or specificity by accessing large numbers of spatial arrangements of metal binding groups.

In addition to availability, reactivity and stability, a criteria in the selection of turn elements for generating the PBM library is the "rigidity" of the molecule. For purposes of the invention described herein, the term "rigid" refers to the physical state of molecular structures having degrees of freedom of intramolecular rotation that are restricted in comparison with those of a simple linear chain. The choice of turn elements preferably favors groups with limited degrees of freedoms, though examples of linear turn elements are provided below as well. In preferred embodiments, the turn element has a reduced number of internal rotational bonds, e.g., relative to a straight chain alkyl.

The chelate effect is a thermodynamic phenomenon in which the stability of a metal-ligand complex is enhanced due to the increase in entropy associated with dissociation of solvent molecules from both the metal's coordination sphere and the ligand(s) upon Li-; chelation. However, the process of metal complexation by the subject PBM molecules "freezes out" a large a population of PBM sidechain conformations at an entropic cost. This phenomenon is a manifestation of the entropic source of the chelate effect; fewer degrees of freedom mean a smaller entropy loss upon binding at the second and later coordination sites. On the other hand, too much rigidity can be detrimental if binding causes strain in the system. By controlling the structure of the turn element, based at least in part on use of a conformationally constrained turn element, MBG sidechain lengths and branch multiplicity, the free volume available to the metal binding groups can be controlled in a manner which balances the entropic and steric factors involved in metal coordination, e.g., to provide maximal control of the spatial predisposition of the ligand group(s) towards effective metal complexation.

The stereochemical constraints of a ring turn element can serve to orient and predispose the metal binding groups of its substituents to maximal overlap with available empty metal orbitals, and as appropriate, to maximize ligand-dipole to metal electostatic bonding. In this manner, a turn element(s) can be selected with optimized pre-control and pre-organization in mind, e.g., for reducing the entropic cost of metal complex formation.

The ability to utilize stereochemical diversity in the turn element(s) of the PBM library is described in greater detail in the appended examples. However, the following scheme further illustrates this point. Beginning with a meso epoxide, enantioselective ring opening can provide enantiomerically enriched turn elements which can be further derivatized with, e.g., stereochemically defined MPG monomers to yield libraries of diastereomerically variegated compounds.

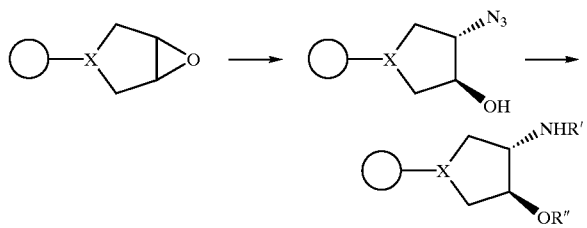

To further elaborate, in one representative embodiment, Tentagel, a polystyrene-polyethylene glycol copolymer resin (Rappe Polymere, Tubingen, Germany) having a cleavable linking arm is cleaved by strong acidic conditions (such as trifluoroacetic acid), is esterified with 4-nitrophenyl chloroformate. The resin is then reacted with tetrahydro-1ah-cyclopenta[b]oxiren-3-ylmethanol to yield the epoxide-derived resin.

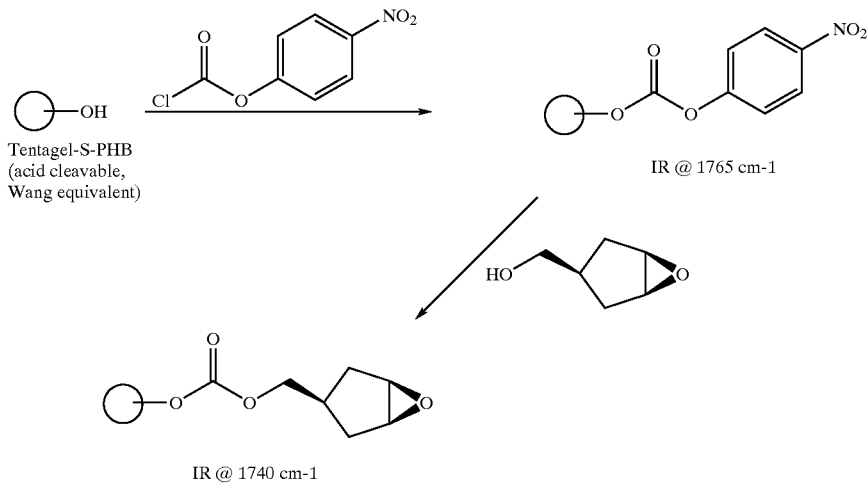

The epoxide is then enantioselectively opened with trimethylsilyl azide (TMSN$_3$) in the presence of a chiral salen catalyst 1,2,-bis(3,5-di-tert-butylsalicylide-amino)cyclohexane: Cr, e.g., see U.S. Pat. No. 5,665,890, to yield, in the illustrate reaction, the enantiomerically enriched 3-azido-4-trimethylsilyloxy-cyclopentyl derived polymer. This serves as a useful

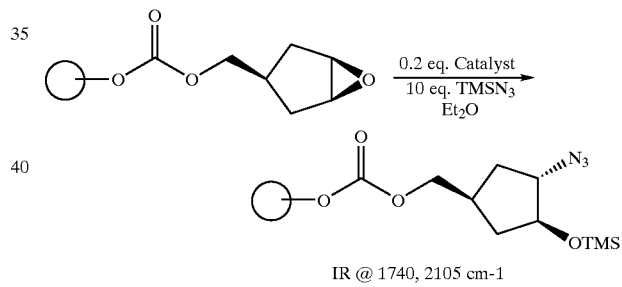

intermediate in the generation of the subject PBM libraries, and the technique can be generally applied to many other epoxides.

In preferred embodiments, the turn element is a ring moiety, e.g., a carbocyclic or heterocyclic moiety which may be monocyclic or polycyclic, aromatic or non-aromatic. Exemplary turn elements of this type include, but are not limited to, acridarsine, acridine, anthracene, arsindole, arsinoline, azepane, benzene, carbazole, carboline, chromene, cinnoline, furan, furazan, hexahydropyridazine, hexahydropyrimidine, imidazole, indane, indazole, indole, indolizine, isoarsindole, isobenzofuran, isochromene, isoindole, isophosphindole, isophosphinoline, isoquinoline, isorasinoline, isothiazole, isoxazole, morpholine, naphthalene, naphthyridine, oxazole, oxolane, perimidine, phenanthrene, phenanthridine, phenanthroline, phenarsazine, phenazine, phenomercurazine, phenomercurin, phenophosphazine, phenoselenazine, phenotellurazine, phenothiarsine, phenoxantimonin, phenoxaphosphine, phenoxarsine, phenoxaselenin, phenoxatellurin, phenothiazine, phenoxathiin, phenoxazine, phosphanthene, phosphindole, phosphinoline, phthalazine, piperazine, piperidine, pteridine, purine, pyran, pyrazine, pyrazole, pyridazine, pyridine, pyrimidine, pyrrolidine, pyrrolizine, quinazoline, quinoline, quinolizine, quinoxaline (such as pyrrole), selenanthrene, selenophene, tellurophene, tetrahydrofuran, tetrahydrothiophene, thianthrene, thiazole, thiolane, thiophene or xanthene.

Thus, in one embodiment the PBMs of the library can be represented by the general formula:

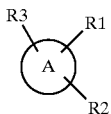

wherein
A represents a carbocycle or heterocycle which can be monocyclic or polycyclic, aromatic or non-aromatic;
R1 and R2 each represent, independently for each occurrence in a PBM of the PBM library, an MPG including a moiety selected from the group consisting of amines (primary, secondary, and tertiary and aromatic amines), amino groups, amido groups, nitro groups, nitroso groups, amino alcohols, nitrites, imino groups, phosphates, phosphonates, phosphites, (substituted) phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfates, sulfonates, sulfonones, sulfonamides, sulfamoyls and sulfinyls, or alkyl alkenyl or alkynyl groups (preferably in the range of $C_1$–$C_{30}$) substituted therewith; and
R3 is absent or represents one or more further MPG substitutions to the ring A, each occurrence of which independently includes a moiety selected from the group consisting of amines (primary, secondary, and tertiary and aromatic amines), amino groups, amido groups, nitro groups, nitroso groups, amino alcohols, nitrites, imino groups, phosphates, phosphonates, phosphites, (substituted) phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfates, sulfonates, sulfonones, sulfonamides, sulfamoyls and sulfinyls, or alkyl, alkenyl, alkynyl or aryl groups (preferably in the range of $C_1$–$C_{30}$) substituted therewith.

One source for the turn elements of the subject method are the conformationally constrained mimetics used to generate peptidomimetics, as for example, the benzodiazepines (see, e.g., James et al. (1993) Science 260:1937), substituted lactam rings (Garvey et al. in Peptides: Chemistry and Biology, G. R. Marshall ed., ESCOM Publisher: Leiden, Netherlands, 1988, p123) and phenoxathin ring systems (Kemp et al. (1988) Tetrahedron Lett. 29:4931; Kemp et al. (1988) Tetrahedron Lett. 29:4935). Thus, many of the conformational motifs used in the peptidomimetic art, such as β-turns, are used to advantage in the present PBM design protocol.

To illustrate, the turn element of the subject method can be produced using either external or internal β-turn mimetics. External β-turn mimetics were the first to be produced. Friedinger et al. (1980) Science 210:656–658, discloses a conformationally constrained nonpeptide β-turn mimetic monocyclic lactam that can readily be substituted with a variety of metal binding groups according to the present method. However, one skilled in the art will appreciate that, in certain embodiments, such external turn elements can give rise to numerous limitations. Chief among these is bulkiness, which may interfere with the metal coordination space accessible to the MBGs added as substitutents to the turn element. Thus, in certain embodiments it will be desirable to use the so-called "internal" β-turn mimetics. The lack of bulk in the internal β-turn can diminish the likelihood of steric hindrance of the added MBGs by the turn element. Internal β-turn mimetics which can be used in the subject method are known in the art. For example, Kahn et al. (1986) Tetrahedron Lett. 27:4841–4844 discloses an internal β-turn mimetic based upon an indolizidinone skeleton.

In preferred embodiments, the turn element is a substituted lactam, e.g., either a monocyclic or a polycyclic lactam. As used herein, a "lactam" includes any organic ring having an amide linkage internal to the ring, as for example β-carbolines containing a γ- or δ-lactam ring.

In still another embodiment, the turn element is generated from a polycyclic moiety, e.g., having two or more rings with two or more common (bridgehead) ring atoms, e.g., so that there are three or more different paths (bridging substituents) between the bridgehead atoms.

In certain instances, the turn element will be a polycyclic alkane, or bridged carbocycle, and may preferably be a bicyclic alkane. The generic name for bicyclic alkanes is bicyclo[x.y.z]alkane, where x, y and z are the numbers of intervening carbon atoms on the three paths between the two bridgehead carbons. Similar nomenclature is used for bridged heterocycles. Exemplary bicyclic alkanes for use in the present invention include such compounds as: 2-methylbicyclo[2.1.0]pentane, bicyclo[2.1.1]hexane, 1,4-dimethylbicyclo[2.2.0]hexane, bicyclo[2.2.1]heptane (norbornane), 7,7-dimethylbicyclo[2.2.1]heptane, endo-2-isopropyl-7,7-dimethylbicyclo[2.2.1]heptane, trans-bicyclo[4.4.0]decan-3-one, bicyclo[2.2.2]octane, 1,4-diisopropylbicyclo[2.2.2]octane, (2s,3s)-2-ethyl-3-methyl-bicyclo[2.2.2]octane, bicyclo[3.1.0]hexane, 2,6,6-trimethylbicyclo[3.1.1]heptane, bicyclo[3.2.0]heptane, bicyclo[3.2.2]nonane, bicyclo[3.3.0]octane, 1,2-dimethylbicyclo[3.3.0]octane, bicyclo[3.3.3]undecane, bicyclo[4.1.0]heptane, (1s,2r,4s,6r)-4-ethyl-1-isopropylbicyclo[4.1.0]heptane, cis-bicyclo[4.2.1]nonane, 1,9-dimethylbicyclo[4.2.1]nonane, trans-1,6-dibromobicyclo[4.3.0]nonane, 1-methyl-8-propylbicyclo[4.3.0]nonane, bicyclo[4.3.2]undecane, cis-bicyclo[4.4.0]decane (cis-decalin), transbicyclo[4.4.0]decane (trans-decalin), and trans-bicyclo[4.4.0]decan-3-one, In other instances, the polycycle used to form the turn element can be a bridged heterocycle. The bridging substituent can be, for example, an azimino (—N=N—HN—), an azo (—N=N—), a biimino (—NH—NH—), an epidioxy (—O—O—), an epidithio (—S—S—), an epithio (—S—), an epithioximino (—S—O—NH—), an epoxy (—O—), an epoxyimino (—O—NH—), an epoxynitrilo (—O—N=), an epoxythio (—O—S—), an epoxythioxy (—O—S—O—), a furano (—$C_4H_2O$—), an imino (—NH—), or a nitrilo (—N=) moiety. Exemplary bridged heterocycles include 7-azabicyclo-[2.2.1]heptane, and 3,6,8-trioxabicyclo[3.2.2]nonane, 2,6-dioxabicyclo[3.2.1]oct-7-yl, and substituted forms thereof.

Preferred bicyclic moieties for use as turn elements are those in which each bridging substitutents includes at least one atom between each bridging atom, e.g., x, y and z are each integers equal to or greater than 1.

In similar fashion, other embodiments of the turn element include polycycles having three or more bridging atoms and three or more rings, e.g., such as the so-called polycyclic cage compounds. For instance, the turn element can be derived from adamantane, diamantane, cubane, quadricyclene (tetracyclo[2.2.1.0$^{(2,6)}$. 0$^{(3,5)}$]heptane), to name but a few. Compounds containing adamantane subunits, for example, have been of interest to chemists due to the rigid structure and well-defined substitution chemistry of the tricyclic compound. This feature of the adamantane molecule can be exploited to generate the subject PBMs. Moreover, numerous synthetic schemes have been derived for substituting the adamantane rings. See, for example, U.S. Pat. Nos. 3,388,164 and 3,391,142 (synthesis of aminoadamantane); Molle et al. (1982) *J Org Chem* 47:4120 (carbocation chemistry of the adamantane system), and U.S. Pat. No. 5,599,998 (subsitution of halo-adamantanes). To illustrate, 1-adamantanamine can be coupled by well-known protocols to an amine-containing support using a homobifunctional crosslinking reagent such as succinic acid (n=2) or the like as a tether to the support.

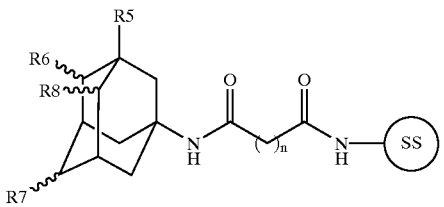

In the illustrated embodiment, R5, R6, R7 and R8 represent substituents on the adamantane rings which include metal binding groups, and (optionally) spacers elements and/or end cap elements. For instance, R5, R6, R7 and R8 represent, independently, amines (primary, secondary, and tertiary and aromatic amines), amino groups, amido groups, nitro groups, nitroso groups, amino alcohols, nitrites, imino groups, phosphates, phosphonates, phosphites, (substituted) phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfates, sulfonates, sulfonones, sulfonamides, sulfamoyls and sulfinyls, or alkyl, alkenyl, alkynyl or aryl groups (preferably in the range of $C_1$–$C_{30}$) substituted therewith.

In another embodiment, the turn element is a saccharide, preferably a mono-, di- or trisaccharide. In preferred embodiments, the turn element is derived from a pentose or hexose sugar or azasugar. Where the saccharide is attached to the solid support, it can be attached glycosidically, retaining the anomeric configuration of the sugar. In other embodiments, the saccharides can be subjected to reductive amination in the presence of a solid support bearing a terminal amine functionality, thereby converting the reducing sugar to an aminoalditol. In an illustrative embodiment of the latter, a pentose sugar having a particular stereoconfiguration about each chiral center is coupled to amino groups of polymer (such as amino ethylated polyacrylamide). For instance, the reducing end of the sugar can be attached to an amino-functionalized surface by reductive amination in the presence of sodium cyanoborohydride.

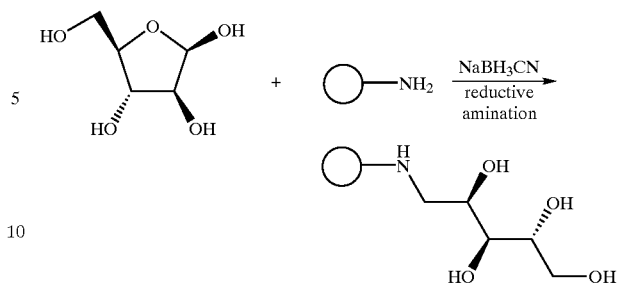

The resulting 1,2,3,4-pentanetetraol provides hydroxyl groups at several chiral sites (asterisks) which are available for further derivatization with MBGs. Because a myriad of cheap, enatiomerically-pure sugars are readily available, such sugars represent an excellent source for a chiral pool of turn elements, e.g., which introduce stereochemical diversity at the turn element position(s).

Specific examples of monosaccharides useful as turn elements in the subject invention include hexoses such as glucose, mannose, galactose, glucosamine, mannosamine and galactosamine; and pentoses such as arabinose, xylose and ribose. Specific examples of oligosaccharides, on the other hand, include disaccharides such as maltose, lactose, trehalose, cellobiose, isomaltose, gentiobiose, melibiose, laminaribiose, chitobiose, xylobiose, mannobiose and sophorose.

In yet another embodiment, the turn element is an azasugar or a phosphanyl sugar, or a derivative thereof. Azasugars include a class of saccharides in which the ring oxygen is replaced by a nitrogen, or in which a ring carbon is replaced with an amino group. A six-membered ring azasugar can be referred to as an azapyranose or a polyhydroxylated piperidine compound. A five-membered ring azasugar can be referred to as an azafuranose or a polyhydroxylated pyrrolidine. An azasugar can also be named as an aza derivative of an otherwise systematically or trivially named pyranose or furanose monosaccharide. Exemplary azasugars which can be used as turn elements may be derived from piperidines (azapyranoses) or from pyrrolidines (azafuranoses). Likewise, phosphanyl sugars include sugars in which a ring position is replaced with a phosphanyl group.

An exemplary use of an azasugar turn element is illustrated below. An azapyranose, such as the (2S,3S,4S,5R) azapyranose shown, can be coupled by well-known protocols to an amine-containing support using a homobifunctional crosslinking reagent such as malonic acid (n=1), succinic acid (n=2) or the like as a tether to the support.

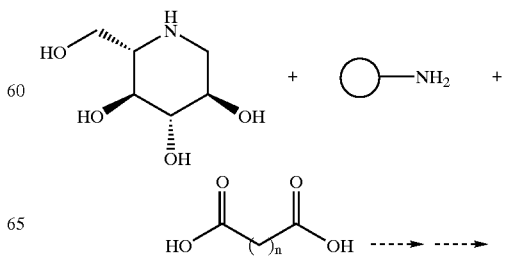

-continued

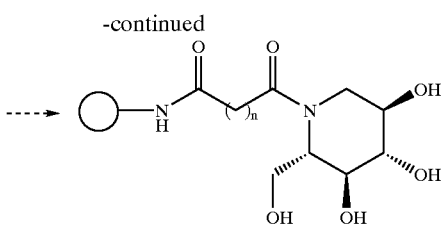

Naturally occurring azasugars can be used to generate the subject turn elements. Exemplary azasugars of this type include 1-deoxynojirimycin (1,5-dideoxy-1,5-imino-D-glucitol), 1-deoxymannojirimycin (1,5-dideoxy-1,5-imino-D-mannitol), and castanospermine (1,6,7,8-tetrahydroxy-octahydroindolizine). 1-Deoxynojirimycin is isolated from plants of the genus Morus (Yagi et al., *Nippnon Nogei Kagaku Kaishi* 1976, 50:5751; Vasella et al., *Helv. Chim. Acta*, 1982 65:1134) and from strains of Bacillus (Daigo et al., *Chem. Pharm. Bull.* 1986, 34:2243). 1-Deoxymannojirimycin is isolated from the legume Lonchocarpus (Fellows et al., *J.C.S. Chem. Comm.* 1979, 977). Castanospermine is a plant alkaloid isolated from seeds of an Australian chestnut tree, *Castanospermum australe* (Saul et al. *Arch. Biochem. Biophys.* 1983, 221 :593].

Both synthetic and semi-synthetic routes have also been used in the syntheses of azasugars and can be readily adapted for generating turn elements in the subject PBM libraries. For instance, synthetic routes to azasugars have commonly entailed processes such as azide displacement/reduction and N-alkylative cyclization with extensive protecting-group manipulation. See, for example, Paulsen et al. (1967) *Chem. Ber* 100:802; Inouye et al. (1968) *Tetrahedron* 23:2125; Saeki et al. (1968) *Chem. Pharm. Bull.* 11:2477; Kinast et al. (1981) *Angew. Chem. Int. Ed. Engl.* 20:805; U.S. Pat. No. 4,266,025; Vasella et al. (1982) *Helv. Chim. Acta* 65:1134; U.S. Pat. No. 4,611,058; Bernotas et al. (1985) *Tetrahedron Lett.* 26:1123; Setoi et al. (1986) *Chem. Pharm. Bull.* 34:2642; Broxterman et al. (1987) *Rec. Trav. Chim. Pays-Bas* 106:571; Fleet et al. (1987) *Tetrahedron* 43:979; Iida et al. (1987) *J. Org. Chem.* 52:3337; Ziegler et al. (1988) *Angew Chem. Int. Ed. Engl.* 27:716; Schmidt et al. (1989) *Liebigs Ann. Chem.* 423; Chida et al. (1989) *J. Chem. Soc., Chem. Commun.* 1230; Beaupere et al. (1989) *Carbohydr. Res.* 191:163; von der Osten et al. (1989) *J. Am. Chem. Soc.* 111:3924, Ikota, N. (1989) *Heterocycles* 22:1469; Tsuda et al. (1989) *Chem. Pharm Bull* 37:2673; Fleet et al. (1990) *Tetrahedron Lett.* 31:490; Anzeveno et al. (1990) *Tetrahedron Lett.* 31 :2085; and Dax et al. (1990) *Carbohydr. Chem.* 9:479.

Natural sugars have been used as starting materials for the production of azasugars, though multiple protection and deprotection steps are required. For example, glucose can be used in the synthesis of 1-deoxynojirimycin and 1-deoxymannojirimycin (Bernotas et al., 1985, supra; and Chen et al., (1990) *Tetrahedron Lett.* 31:2229).

Certain of the semi-synthetic methods can also utilize enzymatic transformations. An enzymatic synthesis based on fructose-1,6-diphosphate (FDP) aldolase (EC 4.1.2.3) has been recently developed and has proven to be a powerful approach for the synthesis of some azasugars (Pederson et al. (1988) *Tetrahedron Lett.* 29:4645; von der Osten et al., supra; Pederson et al. (1989) *Heterocycles* 28:477; Ziegler et al., supra; and Straub et al. (1990) *J. Org. Chem.* 55:3926). This enzymatic method involves the use of FDP aldolase from either rabbit muscle or *Escherichia coli* to catalyze the aldol condensation of dihydroxyacetone phosphate (DHAP; a donor substrate). The omega-azidoketose phosphate produced is dephosphorylated and then reductively cyclized to form a deoxynojirimycin compound. For instance, if DHAP is reacted with (R,S)-3-azido-2-hydroxypropanal in the presence of FDP aldolase, the 2-epimers, 1-deoxynojirimycin and 1-deoxymannojirimycin, are produced upon catalytic reductive amination of the dephosphorylated enzyme reaction products (Pederson et al. *Tetrahedron Lett.* 1988, supra).

TRIS and related compounds can also be ideal bi-functional molecules for use turn elements to which MBGs can join, e.g., via a carboxyl group to the NH2 group or via ester linkage of a carbonyl carbon to a hydroxyl group(s) of TRIS. To illustrate:

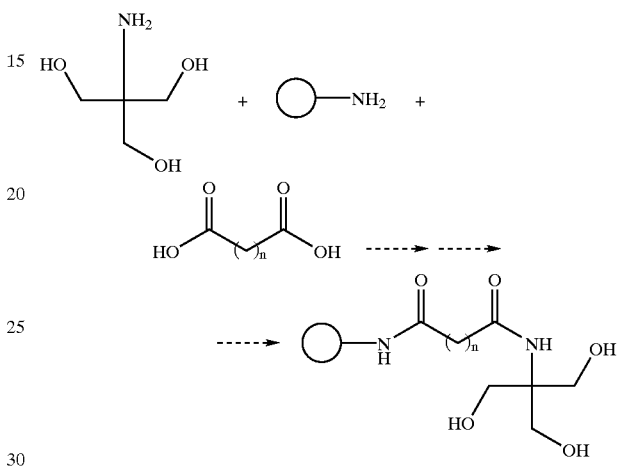

c). End Caps

As described in the appended examples, another component in the synthesis of the subject PBM libraries is the so-called "end cap" units. In general, these components can serve several different purposes. They can, for example, be used as protecting groups for the ends of each string of MBG subunits substituted on a turn element. However, the end caps can also play a role in the metal binding activity of a PBM, e.g., contributing to both affinity and specificity. For instance, as illustrated in the examples, the end cap groups can themselves include Lewis basic atoms which can coordinately bind a metal, and in this regard may also be considered an MBG group. The selection of the end cap can also provide steric diversity around a metal-binding center in the PBM. Likewise, by the use of electron-withdrawing and/or electron-donating groups on the end cap, the Lewis basicity of neighboring MBG units can be influenced. The selection of the end cap can also be used to affect solubility of the PBM.

The phrase "protecting group" as used herein means substituents which protect the reactive functional group from undesirable chemical reactions. Examples of such protecting groups include esters of carboxylic acids, ethers of alcohols and acetals and ketals of aldehydes and ketones.

The phrase "carboxyl-protecting group" as used herein refers to those groups intended to protect a carboxylic acid group, such as the C-terminus of an amino acid or peptide or an acidic or hydroxyl azepine ring substituent, against undesirable reactions during synthetic procedures and includes. Examples for protecting groups for carboxyl groups involve, for example, benzyl ester, cyclohexyl ester, 4-nitrobenzyl ester, t-butyl ester, 4-pyridylmethyl ester, and the like.

The term "amino-blocking group" is used herein as it is frequently used in synthetic organic chemistry, to refer to a group which will prevent an amino group from participating in a reaction carried out on some other functional group, but which can be removed from the amine when desired. Such groups are discussed by T. W. Greene and P. G. M. Wuts in chapter 7 of Protective Groups in Organic Synthesis, 2Ed, John Wiley and Sons, New York, 1991, and by J. W. Barton in chapter 2 of Protective Groups in Organic Chemistry J. F. W. McOmie, ed., Plenum Press, New York, 1973, which are incorporated herein by reference in their entirety. Examples of suitable groups include acyl protecting groups such as, to illustrate, formyl, dansyl, acetyl, benzoyl, trifluoroacetyl, succinyl, methoxysuccinyl, benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonyl-aminocarbonyl. Preferred aminoblocking groups are benzyl (—$CH_2C_6H_5$), acyl [C(O)R] or $SiR_3$ where R is $C_1$–$C_4$ alkyl, halomethyl, or 2-halo-substituted-($C_2$–$C_4$ alkoxy), aromatic urethane protecting groups as, for example, carbonylbenzyloxy (Cbz); and aliphatic urethane protecting groups such as t-butyloxycarbonyl (Boc) or 9-fluorenylmethoxycarbonyl (FMOC).

As shown in the examples, a set of preferred reagents for installing end cap units include: ethanoyl chloride (Acy); 2,2-dimethylpropanoyl chloride (Piv); naphthalenecarbonyl chloride (Nap); 1,3-benzodioxole-5-carbonyl chloride (Pip); methyl 2-chlorocarbonylacetate (Mal); pipicolic or 2-pyridinecarboxylic acid (Pic); 5-oxo-2-pyrrolidinecarboxylic acid (Pga); 4-methyl-1-benzenesulfonyl chloride (Tos); and phenylmethanamide (ICN).

To incorporate N- and/or C-protecting groups, conventional solid phase peptide synthesis methods and other conventional techniques can also be adapted to the subject method. Incorporation of amino-blocking group, for example, can be achieved while the synthesized compound is still attached to the resin, for instance by treatment with suitable anhydride. To incorporate an acetyl protecting group, for instance, the resin-coupled coupled can be treated with 20% acetic anhydride.

IV. Detection of Metal Binding Activity

Libraries of PBMs can be screened for metal-binding activity according to a variety of techniques, some of which are known in the art. For example, as described infra, reagents used in specific qualitative tests for metal ions can be used to determine the presence or absence of metal ions bound to an immobilized PBM. In this embodiment, the immobilized PBMs are contacted with a reagent to detect the presence or absence of particular metal ions. In one embodiment, the metal is detected with an organic spot reagent, e.g., a compound capable of being colored or discolored by reaction with metal ions. At present, a large number of such compounds are known. Exemplary reagents for detecting the metal include: glyoxylbis(2-hydroxyanil), dimethylglyoxime, dithiooxamide, thiocyanate, diphenylthiocarbazide, dimethylglyoxime, benzoinoxime, 8-hydroxyquinoline, dinitrophenylcarbazide, rhodanine, diphenylthiocarbazone, diphenylcarbazone, dithiooxamide, 2-mercapto-4-phenylthiazole, 3,5-dimethylpyrazole, α-naphthylamine-dithiocarbamic acid, benzoinoxime, benzidine, p-dimethylaminobenzylidene rhodanine, salicylaldoxime, triphenyl thiophosphate, p,p'-tetramethyl-diaminodiphenylmethane, anthranilic acid, diphenylbenzine, catechol, gallic acid, dihydroxyriaphthalene, alizarine and quinalizarin.

In addition to detecting colorimetric and/or fluorometric properties of PBMs complexed with metals, the metal-binding abilities of a PBM can be ascertained by detecting other activities of the complex, such as its use as a catalyst (e.g., reaction efficiency and/or specificity).

PBM libraries can also be screened with reagents which detect functional properties of a target or targets (e.g., metal ions). For example, a probe moiety can be combined with a label moiety, such as a dye, a fluorophor, a radiolabel, or the like, to detect the presence of a target (e.g., by staining a bead). The probe can bind reversibly or irreversibly to the target. For example, a PBM can be screened for the presence of Lewis-acidic metal ions by contacting the PBM library with a moiety (e.g., an aldehyde or other Lewis base) which interacts (reversibly) with such Lewis acids, and in which the Lewis base is joined to a label moiety. Any PBM which has bound a Lewis-acidic metal ion will then become associated, through the Lewis basic moiety, with a label, which can be detected. Illustratively, an azulene aldehyde having a blue color can be used to stain blue any PBM which binds a Lewis-acidic metal ion.

V. Tagging/Deconvolution Techniques for Library

A) Direct Characterization

A growing trend in the combinatorial chemistry field is to exploit the sensitivity of such techniques as mass spectroscopy (MS), e.g., which can be used to characterize sub-femtamolar amounts of compound, to directly determine the chemical identity of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used to originally tether the compound to the matrix. For instance, a bead selected from the a PBM library can be irradiated in a MALDI step in order to release the PBM from the matrix and ionize the PBM for MS analysis.

B) Multipin Synthesis

One form that the PBM library of the subject method can take is the multipin library format. Briefly, Geysen and co-workers (Geysen et al. (1984) *PNAS* 81:3998–4002) introduced a method for generating compound libraries by a parallel synthesis on polyacrylic acid-grated polyethylene pins arrayed in the microtitre plate format. The Geysen technique can be used to synthesize and screen thousands of PBMs per week using the multipin method, and the tethered PBMs may be reused in many assays. Appropriate linker moieties can also been appended to the pins so that the PBMs may be cleaved from the supports after synthesis for assessment of purity and further evaluation (c.f., Bray et al. (1990) *Tetrahedron Lett* 31:5811–5814; Valerio et al. (1991) *Anal Biochem* 197:168–177; Bray et al. (1991) *Tetrahedron Lett* 32:6163–6166).

C) Divide-Couple-Recombine

In yet another embodiment, a variegated library of PBMs can be provided on a set of beads utilizing the strategy of divide-couple-recombine (see, e.g., Houghten (1985) *PNAS*

82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the PBM library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where PBM synthesis occurs on resin that is sealed inside porous polypropylene bags (Houghten et al. (1986) *PNAS* 82:5131–5135). Substituents are coupled to the PBM-resins by placing the bags in appropriate reaction solutions, while all common steps such as resin washing and deprotection are performed simultaneously in one reaction vessel. At the end of the synthesis, each bag contains a single PBM moiety. This technique offers advantages of D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271–280; Fodor, S. P. A. (1991) *Science* 251:767; Pirrung et al. (1992) U.S. Pat. No. 5,143,854; Jacobs et al. (1994) *Trends Biotechnol* 12:19–26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each PBM compound is precisely known; hence, its interactions with other molecules can be directly assessed.

In a light-directed chemical synthesis, the products depend on the pattern of illumination and on the order of addition of reactants. By varying the lithographic patterns, many different sets of test PBMs can be synthesized simultaneously; this characteristic leads to the generation of many different masking strategies.

E) Encoded Combinatorial Libraries

In yet another embodiment, the subject method utilizes a PBM library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-oligomers

The principle of using oligonucleotides to encode combinatorial synthetic libraries was described in 1992 (Brenner et al. (1992) *PNAS* 89:5381–5383), and an example of such a library appeared the following year (Needles et al. (1993) *PNAS* 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, PBM libraries can be derived for use in the subject method, where the oligonucleotide sequence of the tag identifies the sequential combinatorial reactions that a particular bead underwent, and therefore provides the identity of the PBM on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test PBM library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529–2531), orthogonality in synthesis is achieved by employing acid-labile protection for the coding strand and base-labile protection for the ligand strand.

In an alternative approach (Nikolaiev et al. (1993) *Pept Res* 6:161–170), branched linkers are employed so that the coding unit and the test PBM can both be attached to the same functional group on the resin. In one embodiment, a cleavable linker can be placed between the branch point and the bead so that cleavage releases a molecule containing both code and PBM (Ptek et al. (1991) *Tetrahedron Lett* 32:3891–3894). In another embodiment, the cleavable linker can be placed so that the test PBM can be selectively separated from the bead, leaving the code behind. This last construct is particularly valuable because it permits screening of the test PBM without potential interference of the coding groups. Examples in the art of independent cleavage and sequencing of peptide library members and their corresponding tags has confirmed that the .tags can accurately predict the peptide structure.

2) Non-sequenceable Tagging: Binary Encoding

An alternative form of encoding the test PBM library employs a set of non-sequenceable electrophoric tagging molecules that are used as a binary code (Ohlmeyer et al. (1993) *PNAS* 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the PBM would be attached to the solid support via the photocleavable linker and the tag is attached through a catechol ether linker via carbene insertion into the bead matrix (Nestler et al. (1994) *J Org Chem* 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027–6031) and provide guidance for generating the subject PBM library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, ligands are partially detached and transferred to assay plates; third, a metal binding assay identifies the active wells; fourth, the corresponding beads are rearrayed singly into new microtiter plates; fifth, single active PBMs are identified; and sixth, the structures are decoded.

VI. Reaction Conditions

In one aspect of the invention, the subject screening method can be carried out utilizing immobilized PBM libraries. The choice of a suitable polymeric support will be routine to the skilled artisan. In general, the polymeric support will be selected according to at least some of the following criteria: (i) it should not be reactive under conditions used for detecting the metal attached; and (ii) it will have little to no background binding to the metal of interest. The PBMs can be derivatized to the polymeric support utilizing appropriate functional groups and methods known in the art. Those embodiments which employ some form of matrix immobilization of the PBM library are amenable to the use of encoding and/or spatial addressing of the library for later deconvolution.

Insoluble polymeric supports include functionalized polymers based on polystyrene, polystyrene/divinylbenzene copolymers, and other polymers known to the skilled artisan. It will be understood that the polymeric support can be coated, grafted, or otherwise bonded to other solid supports.

In another embodiment, the polymeric support can be provided by reversibly soluble polymers. Such polymeric supports include functionalized polymers based on polyvinyl alcohol or polyethylene glycol (PEG). A soluble support can be made insoluble (e.g., can be made to precipitate) by addition of a suitable inert nonsolvent. One advantage of reactions performed using soluble polymeric supports is that reactions in solution can be more rapid, higher yielding, and/or more complete than reactions that are performed on insoluble polymeric supports. Accordingly, in a preferred embodiments, the polymer support is PEG or PEG-OMe.

In still other embodiments, the PBM library can be synthesized in solution, and by the use of deconvolution techniques, or synthesis in multiple reaction vessels (e.g., microtitre plates and the like), the identity of particular members of the library can be determined.

VII. Exemplification

The invention now being generally described, it will be more readily understood by reference to the following examples which are included merely for purposes of illustration of certain aspects and embodiments of the present invention, and are not intended to limit the invention.

EXAMPLE 1

Figure 2A:
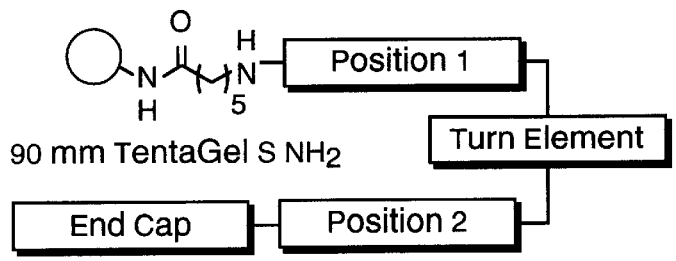
FIGS. 2A–B depict exemplary metal binding moieties of the invention.
Figure 2A:
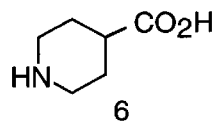
Figure 2A:
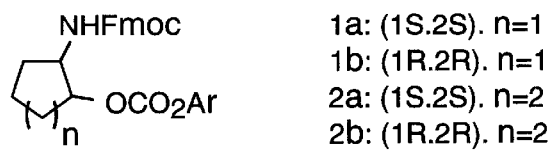
Figure 2A:
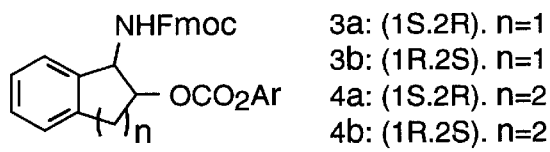
Figure 2A:
Figure 2A:
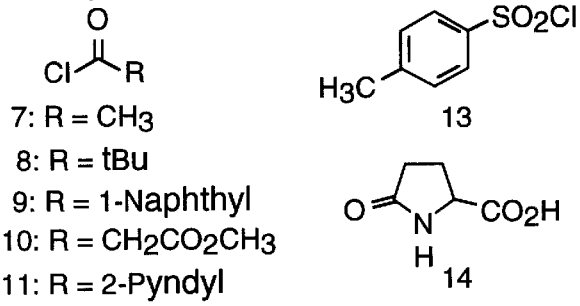
Figure 2A:
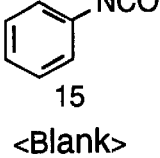

In an exemplary embodiment, see FIG. 2A, the ligand library comprises four variable components: two amino acids (positions 1 and 2), linked by a "turn element" (1a, b–5a, b) and terminated by various capping reagents (7–15).[8] The turn elements are cyclic 1,2-amino alcohol or α-amino acid derivatives with defined relative and absolute stereochemistry, and were introduced with the notion that this conformational restriction would encourage the formation of a potential binding site in which both amino acids side chains might interact with the metal. The ligand library was synthesized on poly(ethylene glycol)-grafted polystyrene (90 μm TentaGel S $NH_2$ resin) using standard splitting/pooling techniques[9] such that each polymer bead displayed a unique ligand structure. The library, which theoretically consists of 12,000 different ligands, was encoded using established tagging methods.[10]

The potential for members of this library to form coordination complexes was evaluated by exposing samples of the beads to homogeneous solutions of selected metal ions. In a representative experiment, a 10 mg. portion of the library (ca. 24,000 beads) was exposed to 0.05 M $Ni(OAc)_2$ in MeOH for 30 min, rinsed with additional MeOH, and air dried. The resulting sample was then treated with a solution of dimethylglyoxime (DMG) in MeOH, a known qualitative test for Ni(II), and the beads were examined under a light microscope. A reddish-pink precipitate was observed to form rapidly and remain trapped in the polymer matrix of about 20% of the beads, confirming the selective incorporation of Ni(II) into some of these ligands.

In order to ascertain which library members had the highest binding affinity for Ni(II), 10 mg library samples were exposed to solutions of decreasing Ni(OAc)$_2$ concentration in methanol buffered with 0.10 M NaOAc and 0.10 M HOAc.[11] As the concentration was lowered, fewer Ni(II) binders were observed, until at a Ni(OAc)$_2$ concentration of $2.5 \times 10^{-4}$ M only 6 binders out of ~24,000 beads[12] were identified.

Figure 2B:
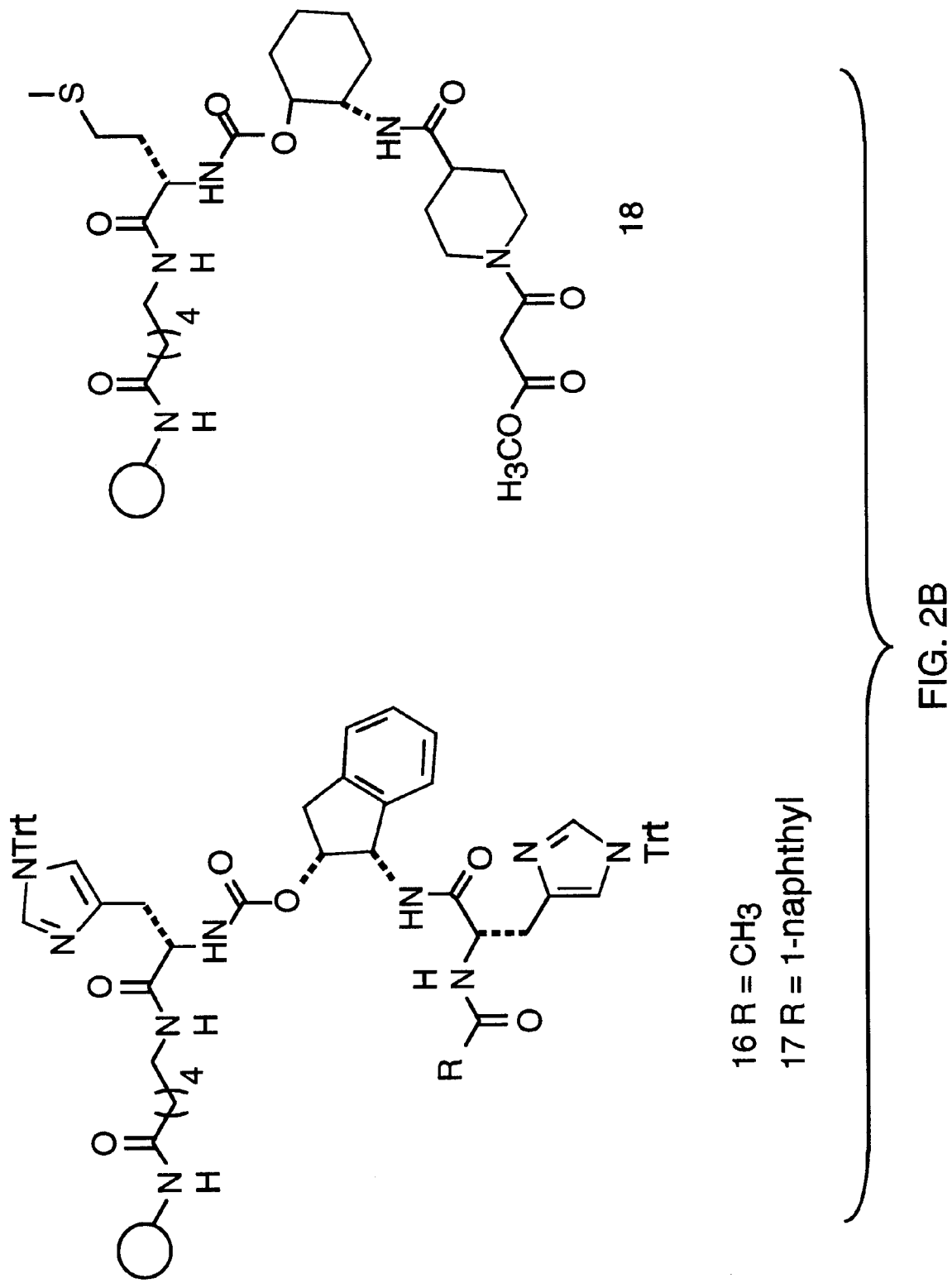

Tag photolysis and GC-ECD analysis (Table 1) allowed the identification of these hits, and revealed a strong structural consensus among the nickle binders. Four different ligands and two duplicates were found, each bearing L-His (Trt) in both amino acid positions. Furthermore, only two turn elements (3a and 2a) and two end caps (7 and 9) were incorporated, suggesting that high affinity binding does not simply result from the presence of the two histidine residues. The identified structures were confirmed to be Ni(II) binders by independent, solution phase synthesis of two of the ligands 16 and 17 (FIG. 2B).[13,14]

TABLE 1

Structures of highest affinity Ni(II) binders.

| Structure | Position 1 | Turn Element | Position 2 | End Cap |
|---|---|---|---|---|
| 1,2 | L-His (Trt) | 3a | L-His (Trt) | 7 |
| 3,4 | L-His (Trt) | 3a | L-His (Trt) | 9 |
| 5 | L-His (Trt) | 2a | L-His (Trt) | 7 |
| 6 | L-His (Trt) | 2a | L-His (Trt) | 9 |

The same ligand library is selective in its complexation of other metal ions. Using conditions similar to those described above, Fe(III) complexes were identified by staining with KSCN in MeOH. Slightly stronger and less discriminate complexation was observed than with Ni(II), with approximately 1% of the ligands incorporating Fe(III) upon exposure to $5 \times 10^{-4}$ M FeCl$_3$, and solutions as dilute as $5 \times 10^{-6}$ M still producing identifiable binders. The structures revealed by tag analysis were found to be very different from those of the Ni(II) binders, and displayed a perfect consensus (64/64 structures) for the unexpected combination of isonipecotic acid (6) in position 2 followed by end cap 10. Half of the high-affinity structures were found to contain Met in position 1 (e.g. 18, FIG. 2B), but no preference for a particular turn element was apparent.

The fact that there is no structural overlap between binders of Ni(II) and of Fe(III) suggested that the library might selectively bind one metal in the presence of the other. A 10 mg sample of the library was exposed to an equimolar solution of Ni(OAc)$_2$ and FeCl$_3$. After 2 h, the sample was rinsed with MeOH and stained sequentially with dithiooxamide in THF (a stain that forms a blue complex with Ni(II)) and KSCN in MeOH (a stain that forms an orange-red complex with Fe(III)). Selective binding to each metal can be identified.

Binding of other ions to the library was also observed, albeit with varying degrees of selectivity. Cu(II) bound to ~30% of the beads, with a marked preference for members containing L-His(Trt). Pt(IV) was also found to complex with up to 30% of the ligands, the majority of which contained a Met residue. Sn(IV) and Pd(II) were observed to bind with vanishing selectivity, suggesting that complexation of these ions might occur solely through the peptide backbone.

EXAMPLE 2

Figure 4A:
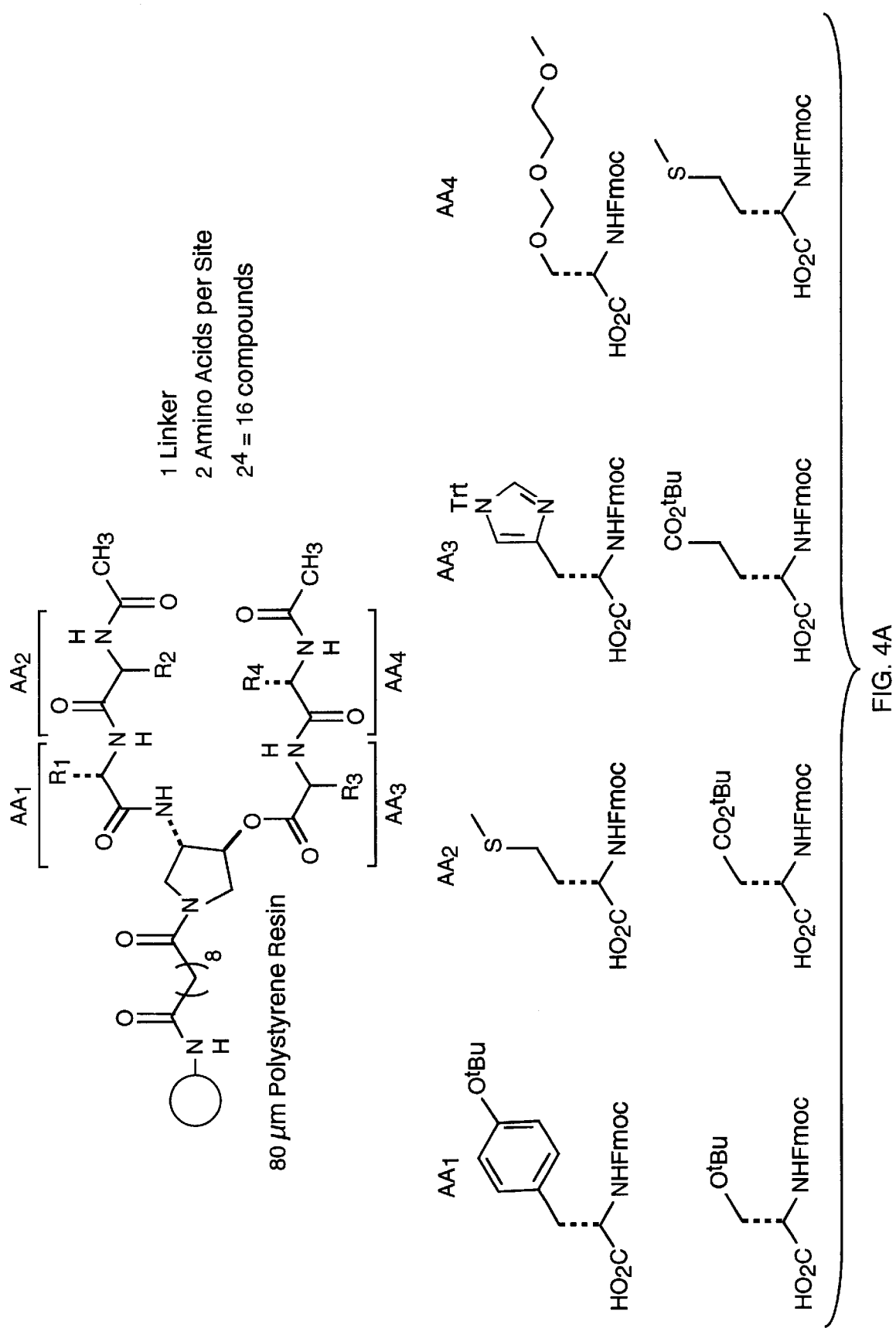
FIGS. 4A–G illustrate the generation of a library of titanium-binding ligands, and the use of these ligands to catalyze the reaction of trimethylsilyl cyanide and benzaldehyde.
Figure 4B:
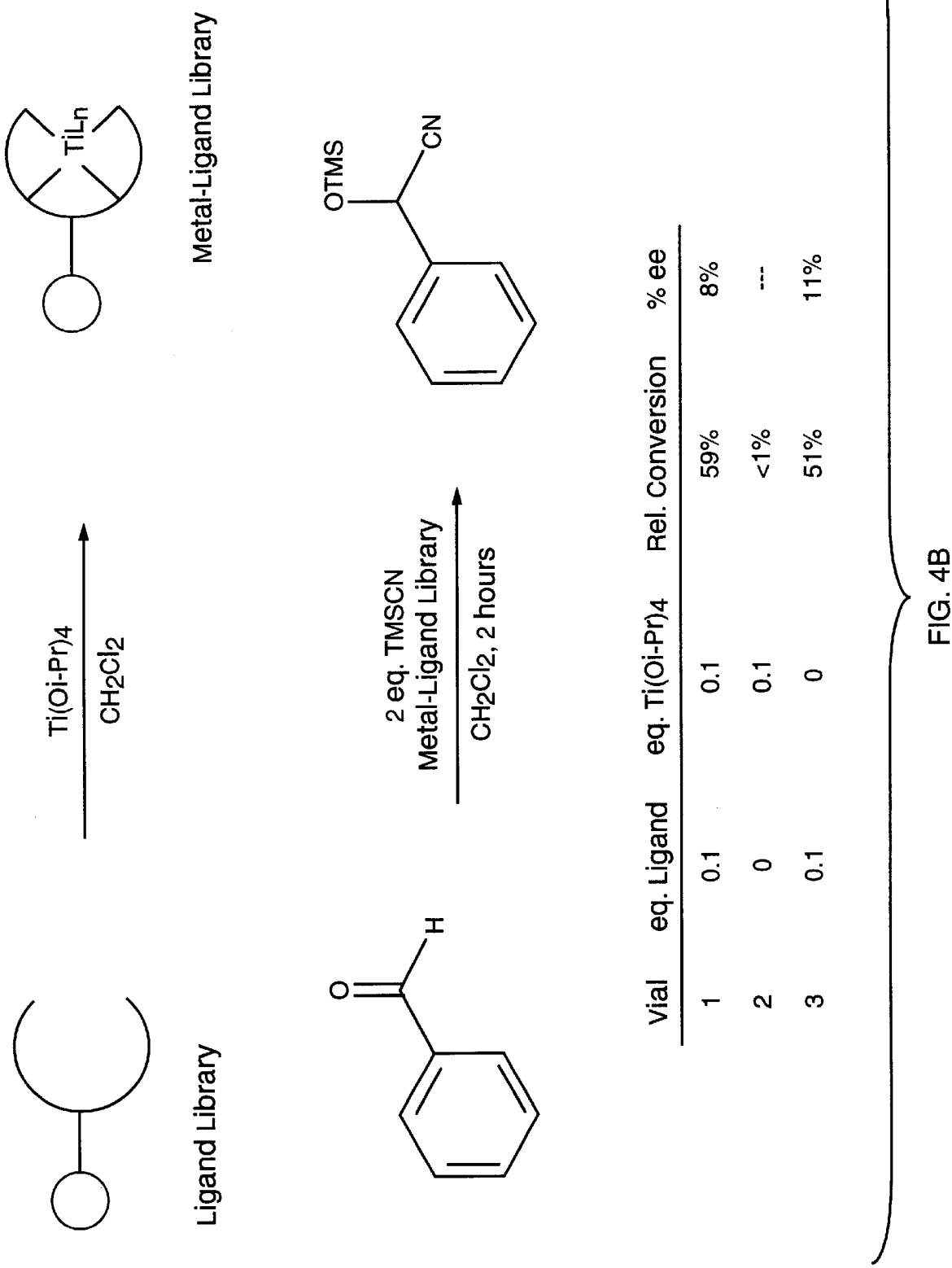

FIGS. 4A–G illustrate the use of the subject method in generating titanium-binding ligands. In an initial reactivity screen, a library of PBMs was generated using a 4-aminotetrahydro-3-pyrrolol-derived turn element substituted with variegated dipeptides (see FIG. 4A). At each amino acid position of the dipeptide substituents, there were provided two possible MBGs, e.g., amino acid residues, so as to yield a library of 16 compounds. As illustrated in FIG. 4B, the ligand library was treated with titanium isopropoxide under conditions wherein the isopropoxide ligand on the titanium could be replaced by members of the ligand library having appropriate affinity for the metal. The metal-ligand library was then provided in a reaction mixture of trimethylsilyl cyanide (TMSCN) and benzaldehyde, and the formation of 2-trimethylsilyloxy-2-phenylacetonitrile was detected. As FIG. 4B illustrates, the PBM library, as a whole, was able to catalyze the reaction.

EXAMPLE 3

Figure 4C:
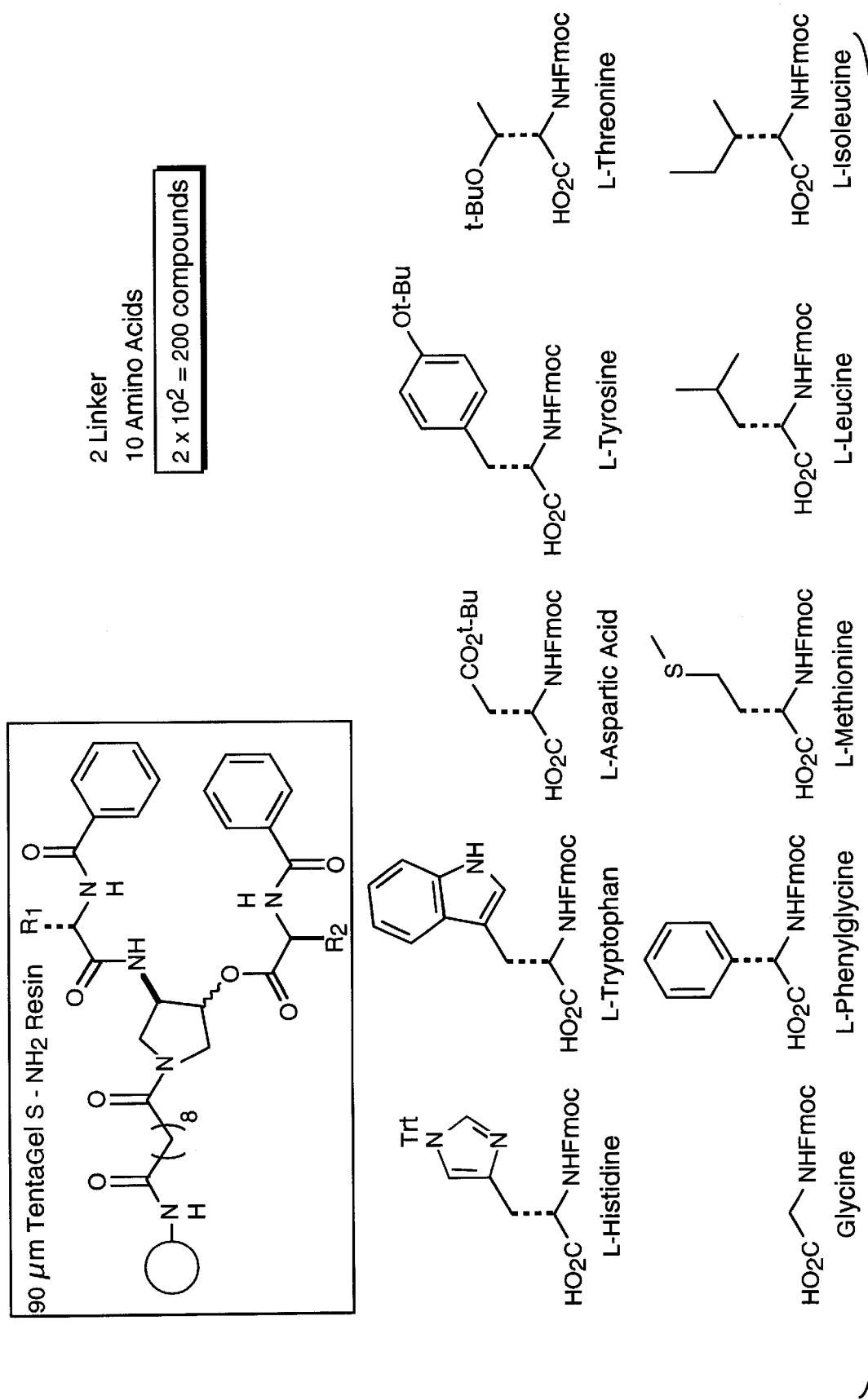
Figure 4D:
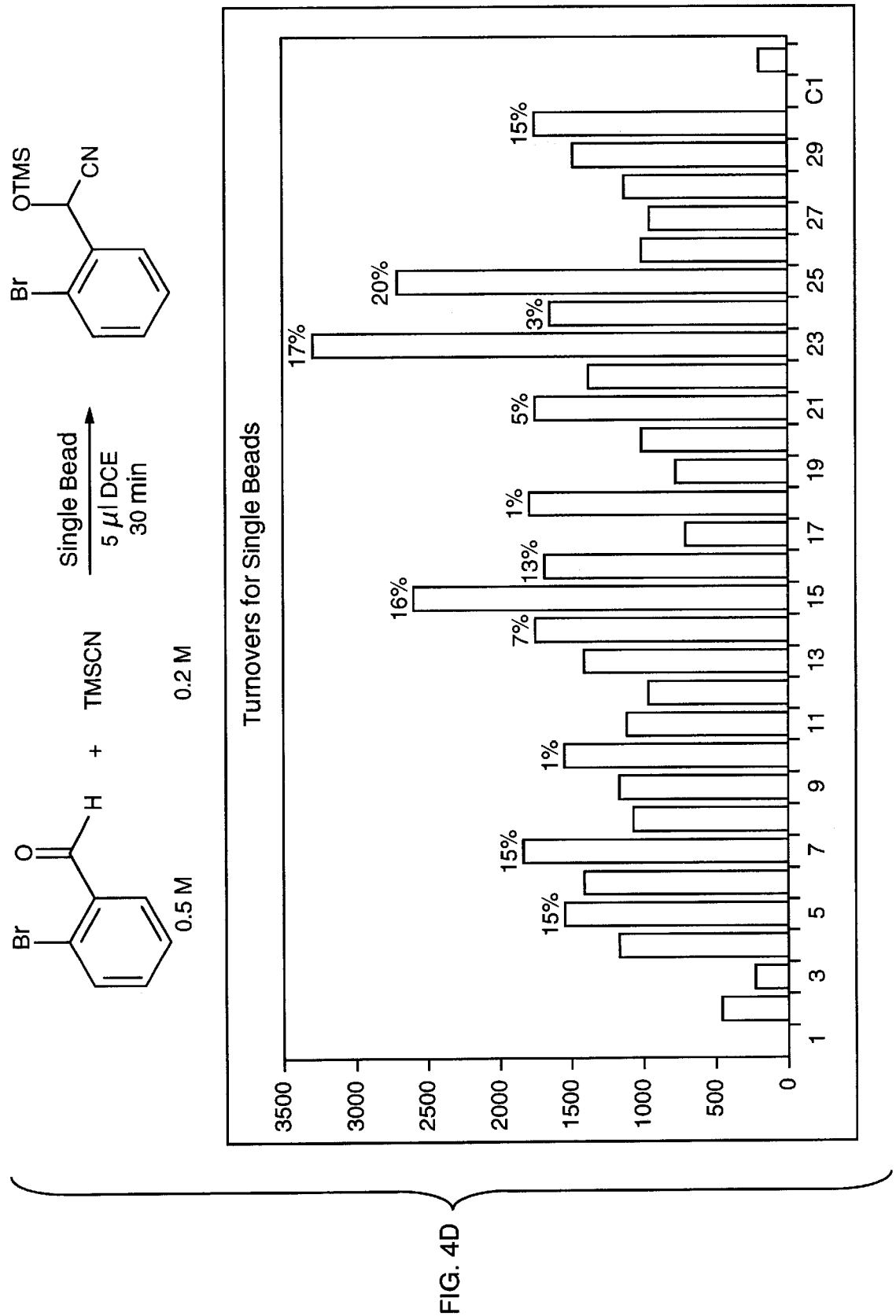
Figure 4E:
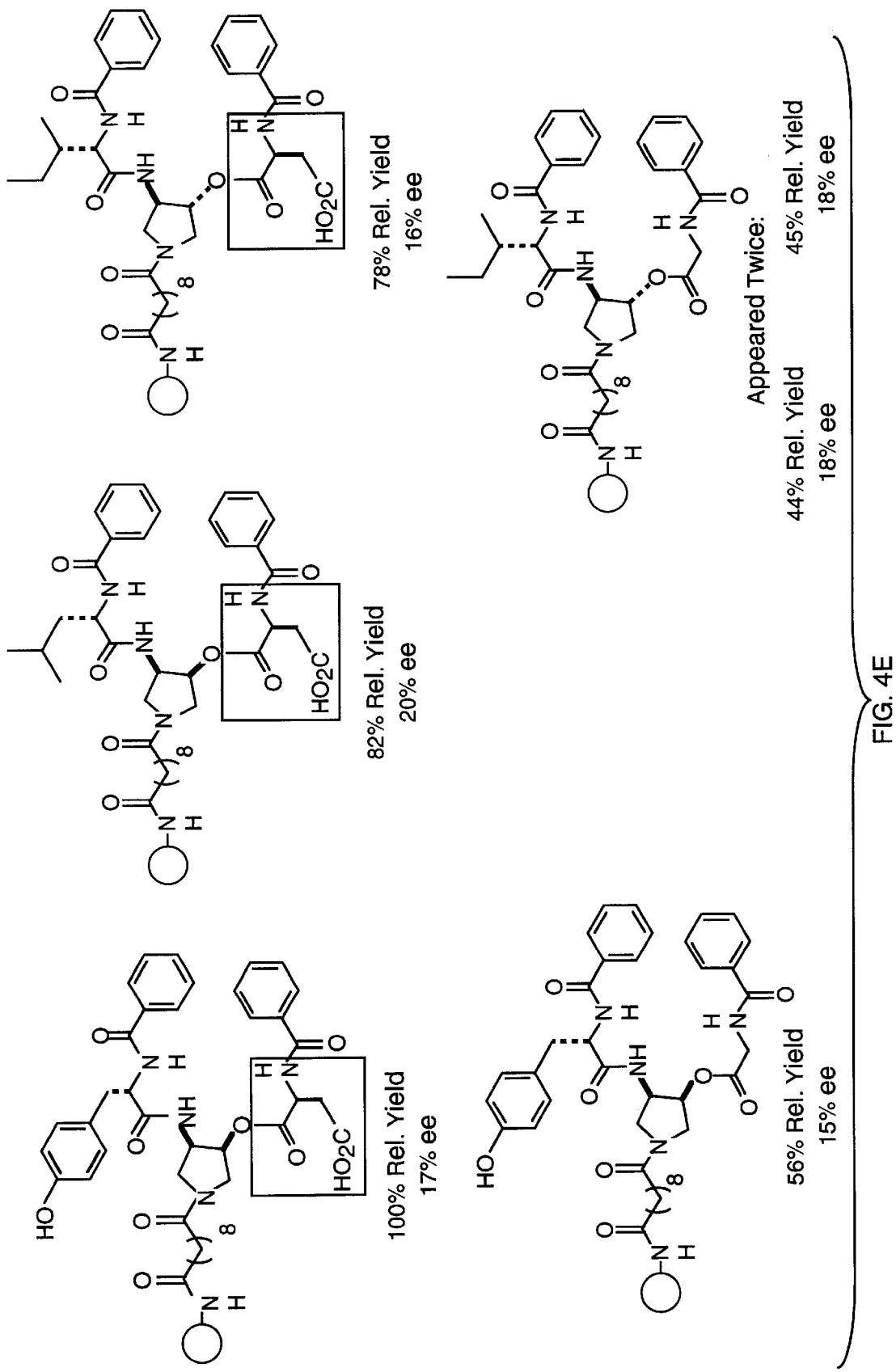
Figure 4F:
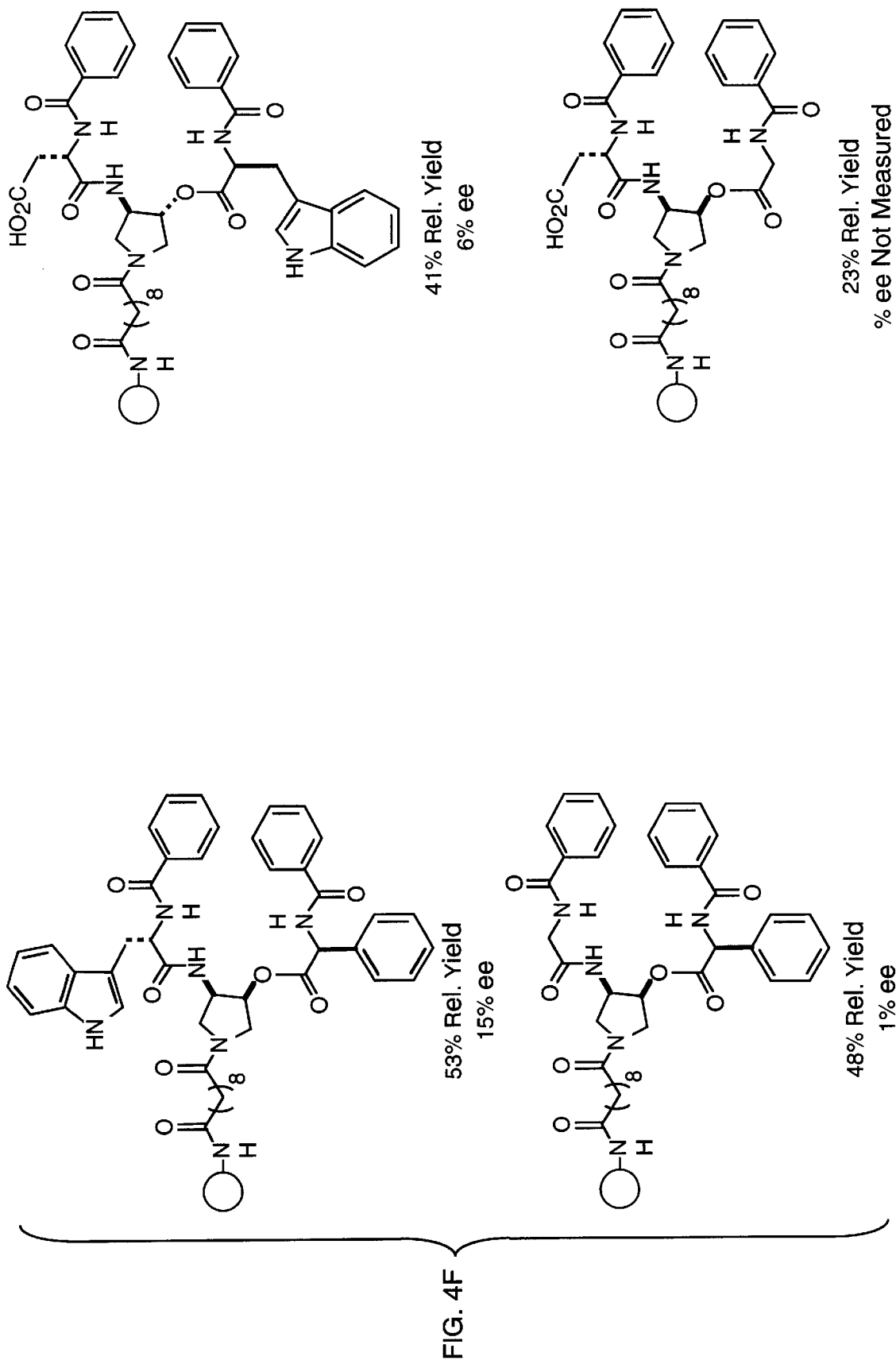
Figure 4G:
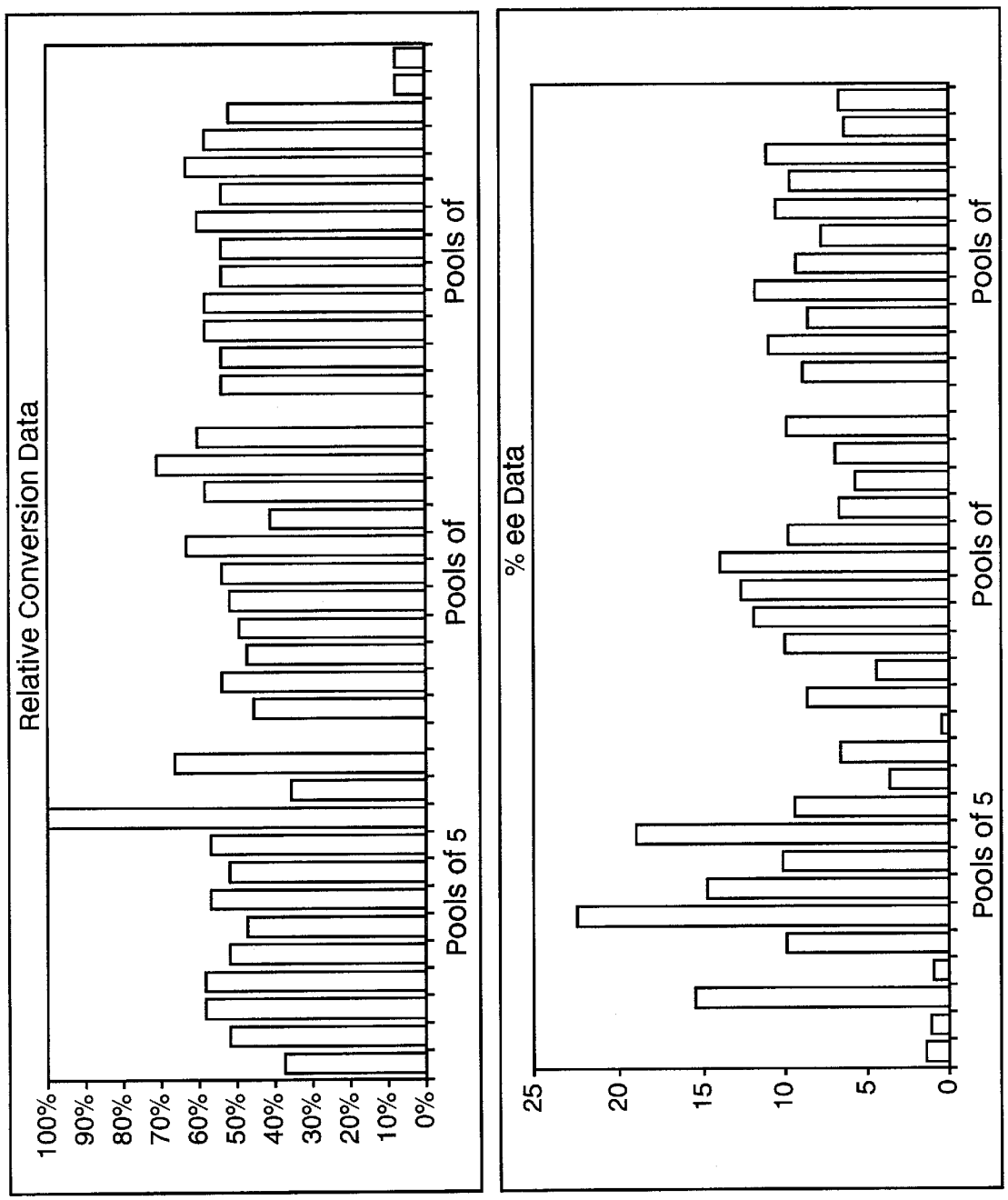

Subsequently, using the same approach, but with an enantiomeric pair of turn elements and 10 different amino acid residues at two different MBG positions, a library of 200 different compounds for screening was generated (see FIG. 4C). The library was synthesized on single beads in a combinatorial manner which produced homogenous PBM populations on each discrete bead. Individual beads were isolated from the library, and each was tested for the ability of the PBM on the bead to catalyze the reaction of TMSCN and 2-bromobenzaldehyde in the presence of titanium (see FIG. 4D). Normalized to the most active bead (bead 23 in FIG. 4D), the most active PBMs were isolated from the library, retested, and the molecular identity of each determined. As illustrated in FIGS. 4E and 4F, certain structural/electronic features of these most active compounds are conserved in interesting ways. FIG. 4G is a bar graph comparing the relative conservation of amino acid residues with the activity and enantioselectivity of the metal-ligand catalysts derived from the subject PBM library.

EXAMPLE 4

Figure 5A:
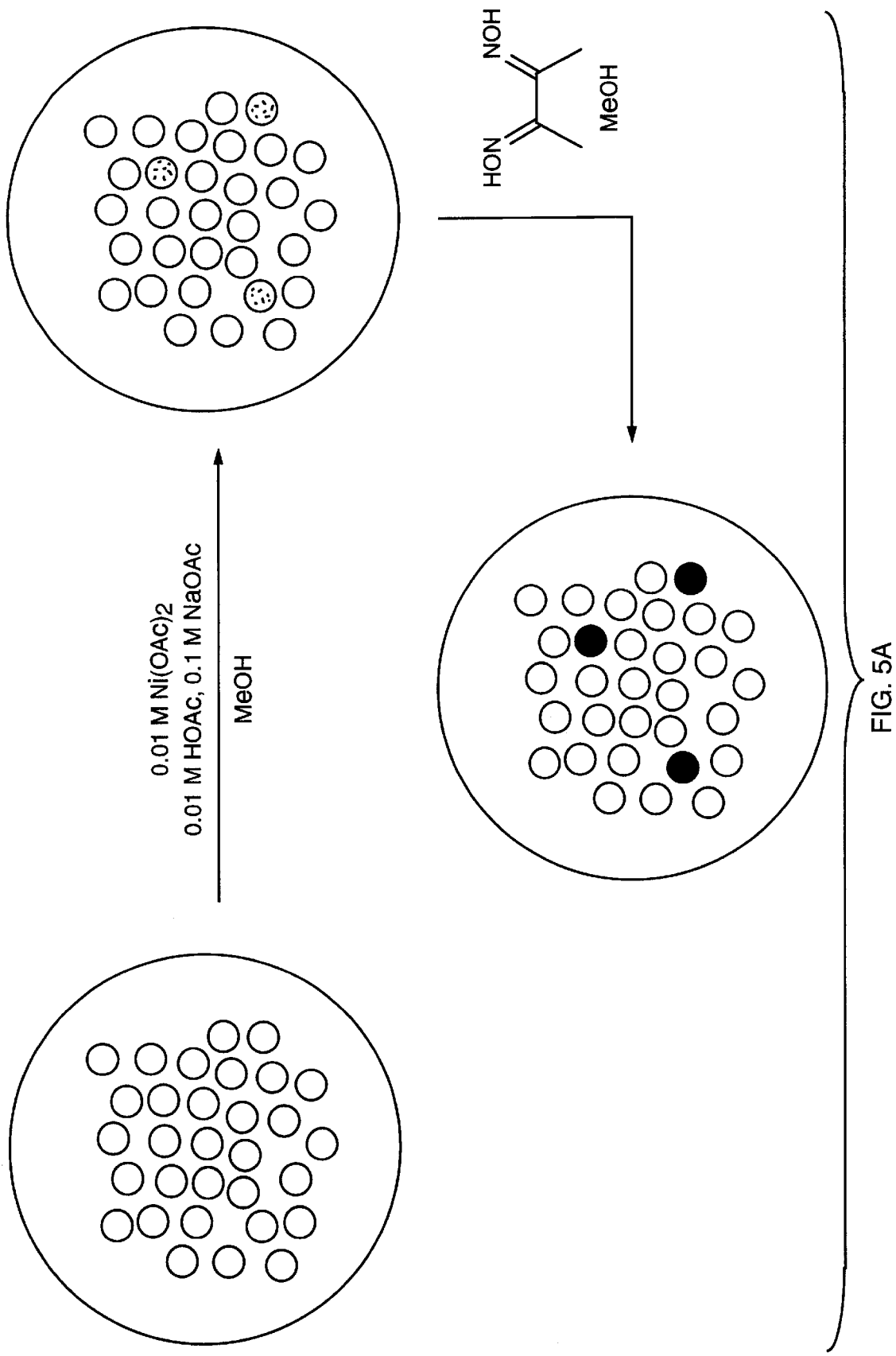
FIGS. 5A–D illustrate the generation of a library of nickel-binding ligands.
Figure 5B:
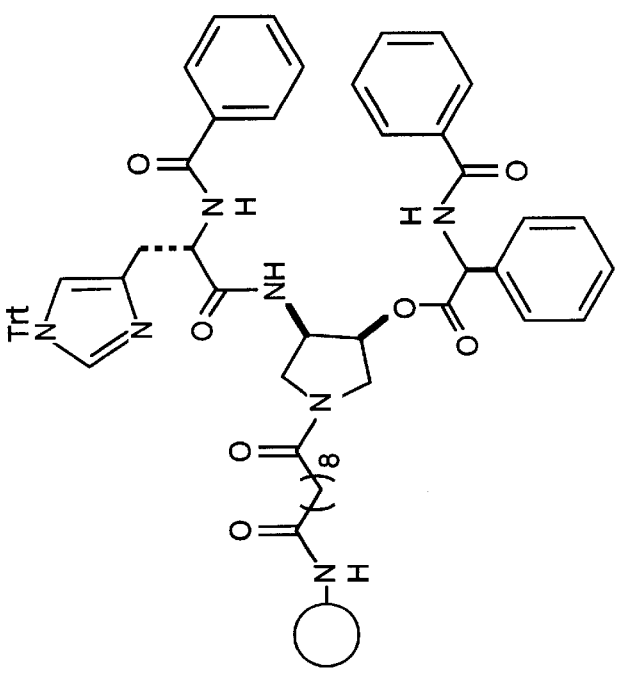

In another validation of the subject combinatorial method, ligands from a library of PBMs were isolated on the basis of ability to bind Ni$^{2+}$. As illustrated in FIG. 5A, and described in detail in Example 1, a library of potential Ni-binding PBMs can be admixed with Ni(OAc)$_2$, and the resulting sample then treated with a solution of dimethylglyoxime (DMG) in MeOH, a known qualitative test for Ni(II). Upon examination of the PBM-bearing beads under a light microscope, the presence of a reddish-pink precipitate on or around a bead indicates the selective incorporation of Ni(II) into ligand present on the bead. By this technique, we screened a variegated library of PBMs generated by use of an enantiomerically diverse turn element position, e.g., generated by incorporation of (R,S) and (R,R) 4-aminotetrahydro-3-pyrrolol-derived turn elements, and variability introduced at certain MBG sites. As indicated in FIG. 5B, certain of the library members demonstrated enhanced nickel-binding activity relative to others and were isolated, with variability in affinity also being observed even amongst these better nickel ligands (shaded entries in FIG. 5B).

EXAMPLE 5

Figure 5C:
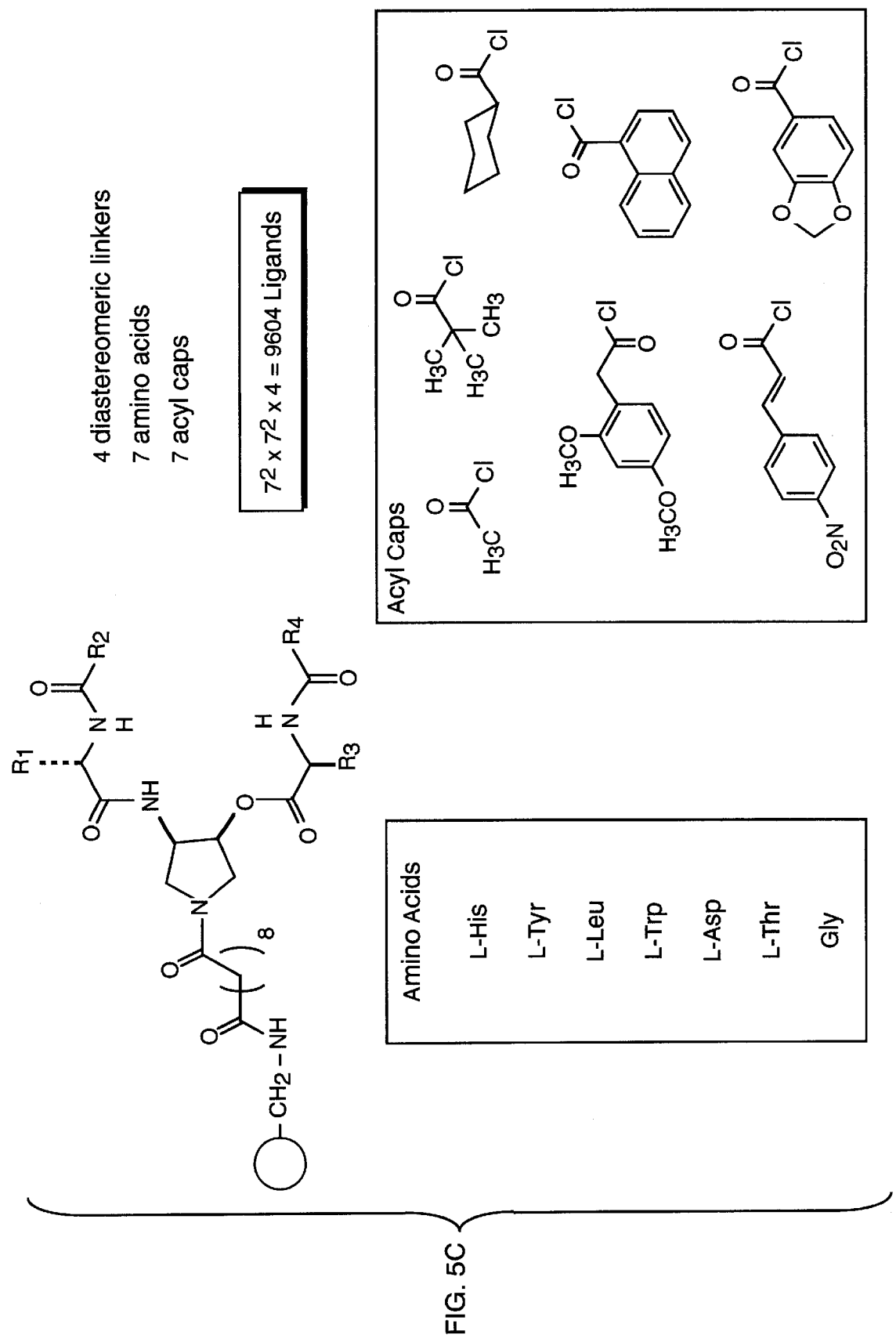
Figure 5D:
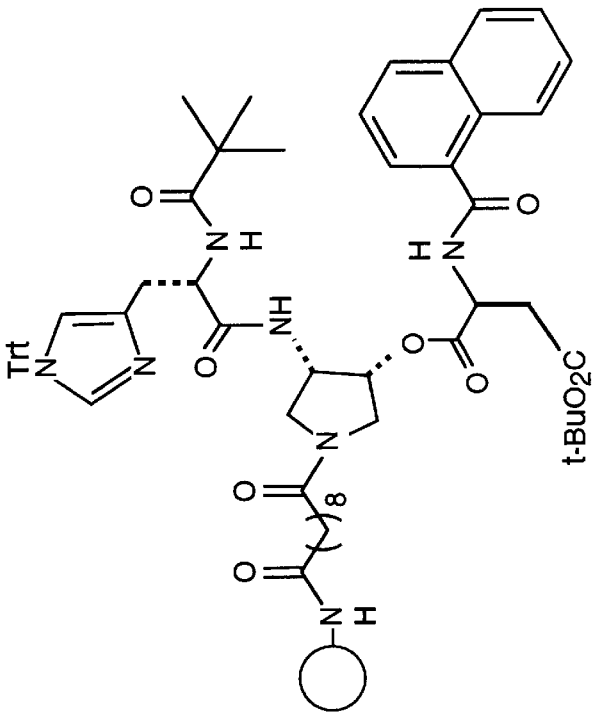

A library of 9604 different PBM entities was also generated by introducing the 4 diasteromeric 4-aminotetrahydro-3-pyrrolol-derived turn elements into the library, as well using 7 different amino acid residues at 2 MBG positions, and 7 different acyl caps (see FIG. 5C). Consistently, the screening of this library selected for PBMS related to the compound shown in FIG. 5D, e.g., having histidine and aspartic acid residues at the two variable MBG sites, and 2,2-dimethylpropanoyl chloride as the acyl endcap adjacent to the histidine.

EXAMPLE 6

Figure 6:
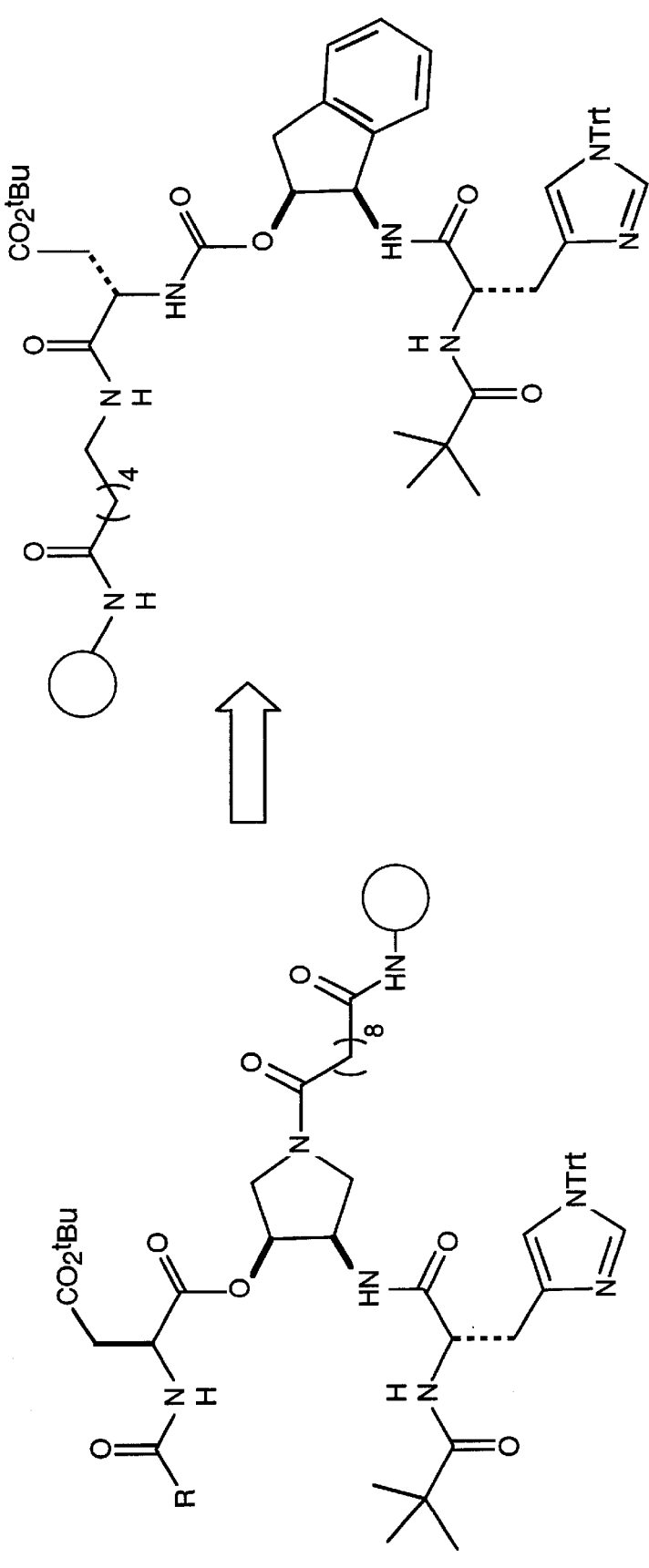
FIG. 6 compares the structure of a so-called "external" turn element with that of an "internal" turn element.
Figure 7A:
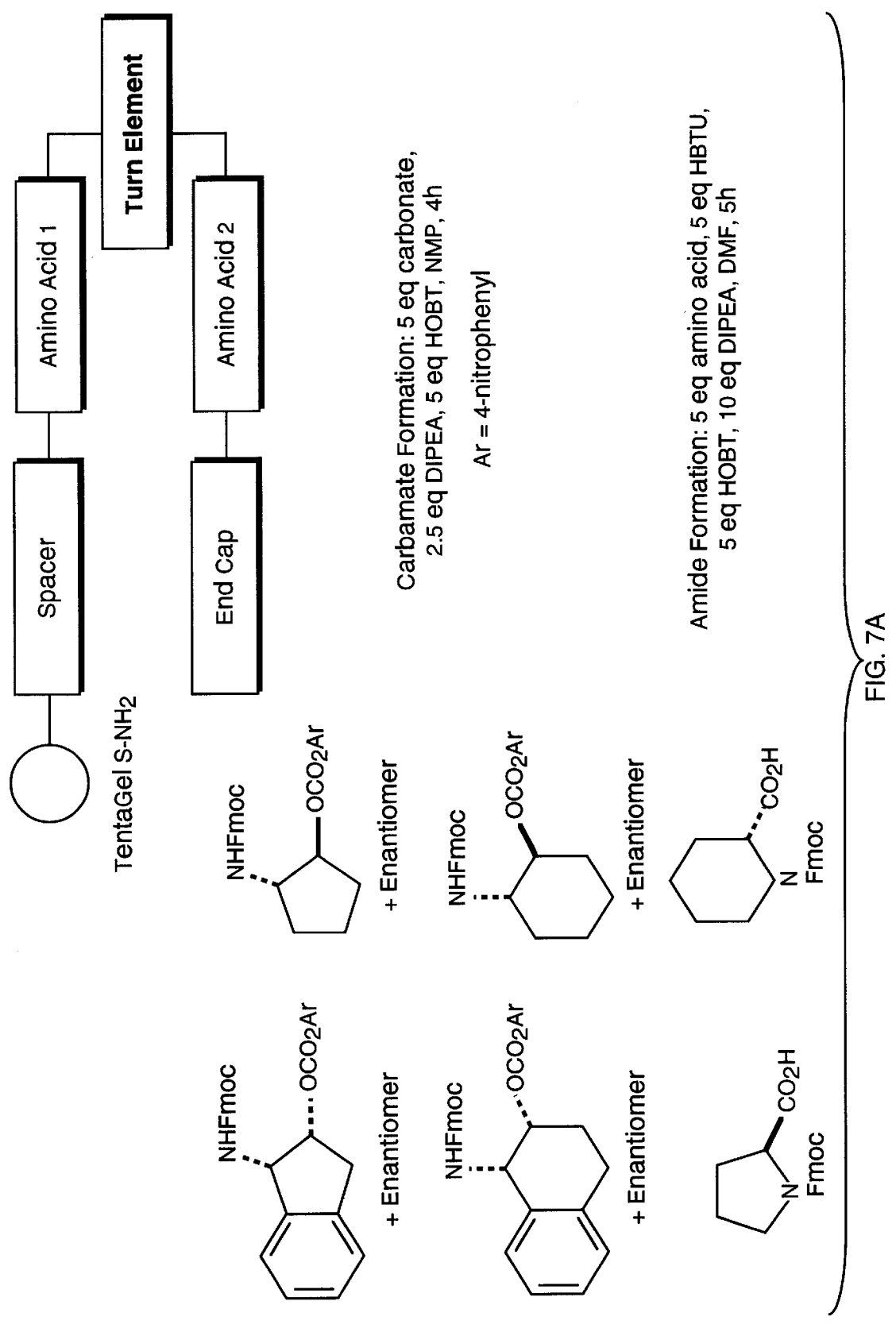
Figure 7B:
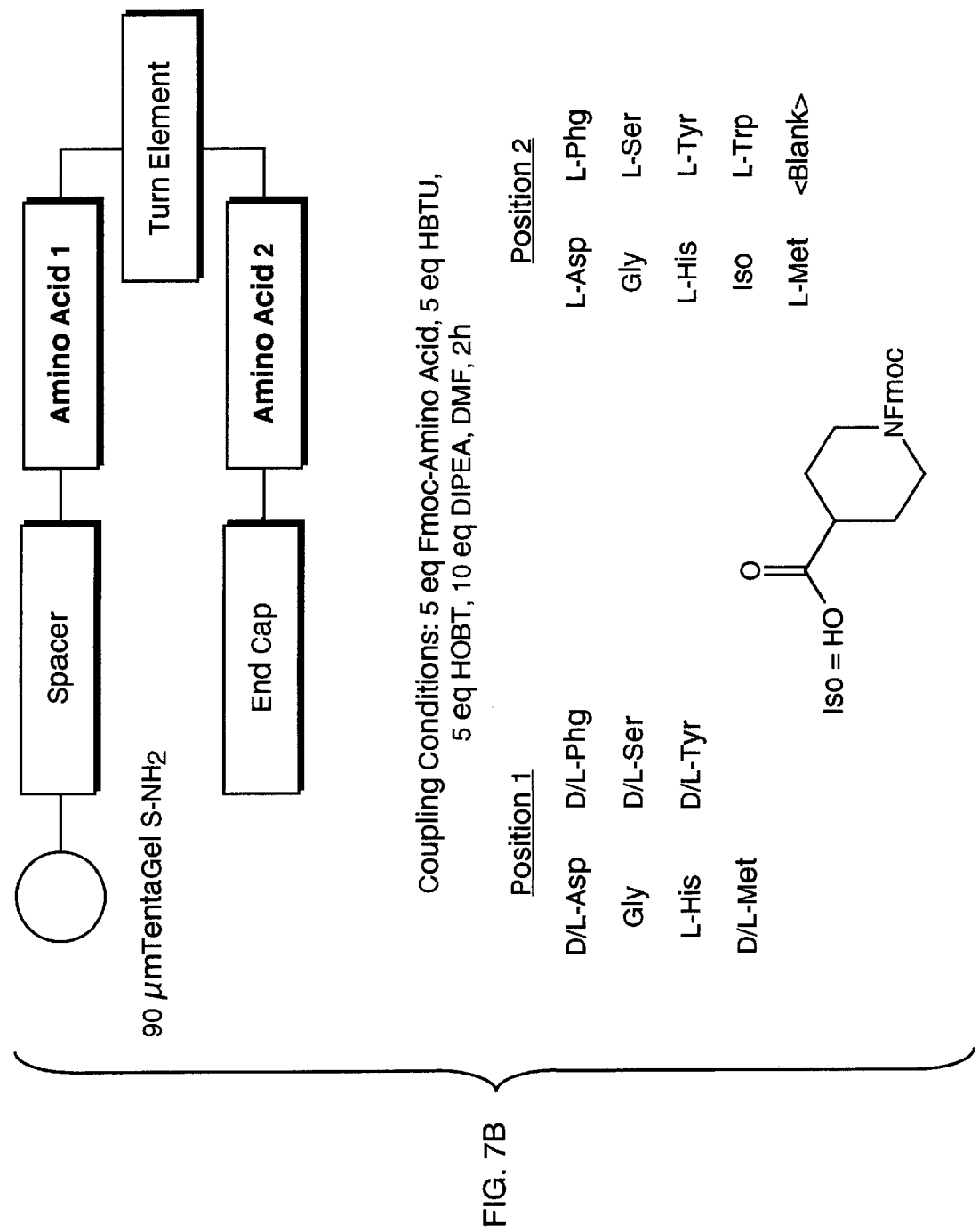
Figure 7C:
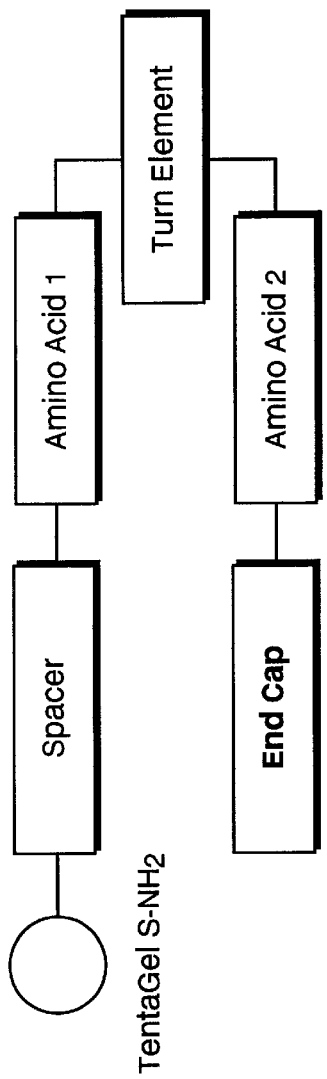
Figure 7C:
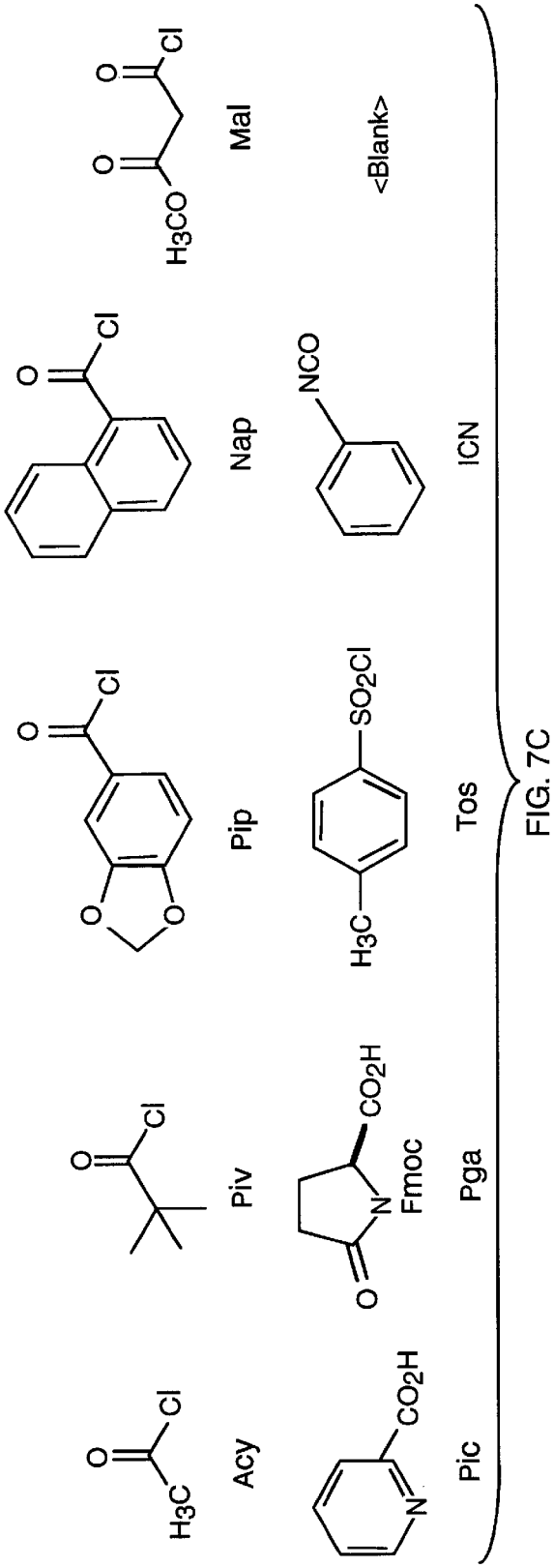
Figure 7D:
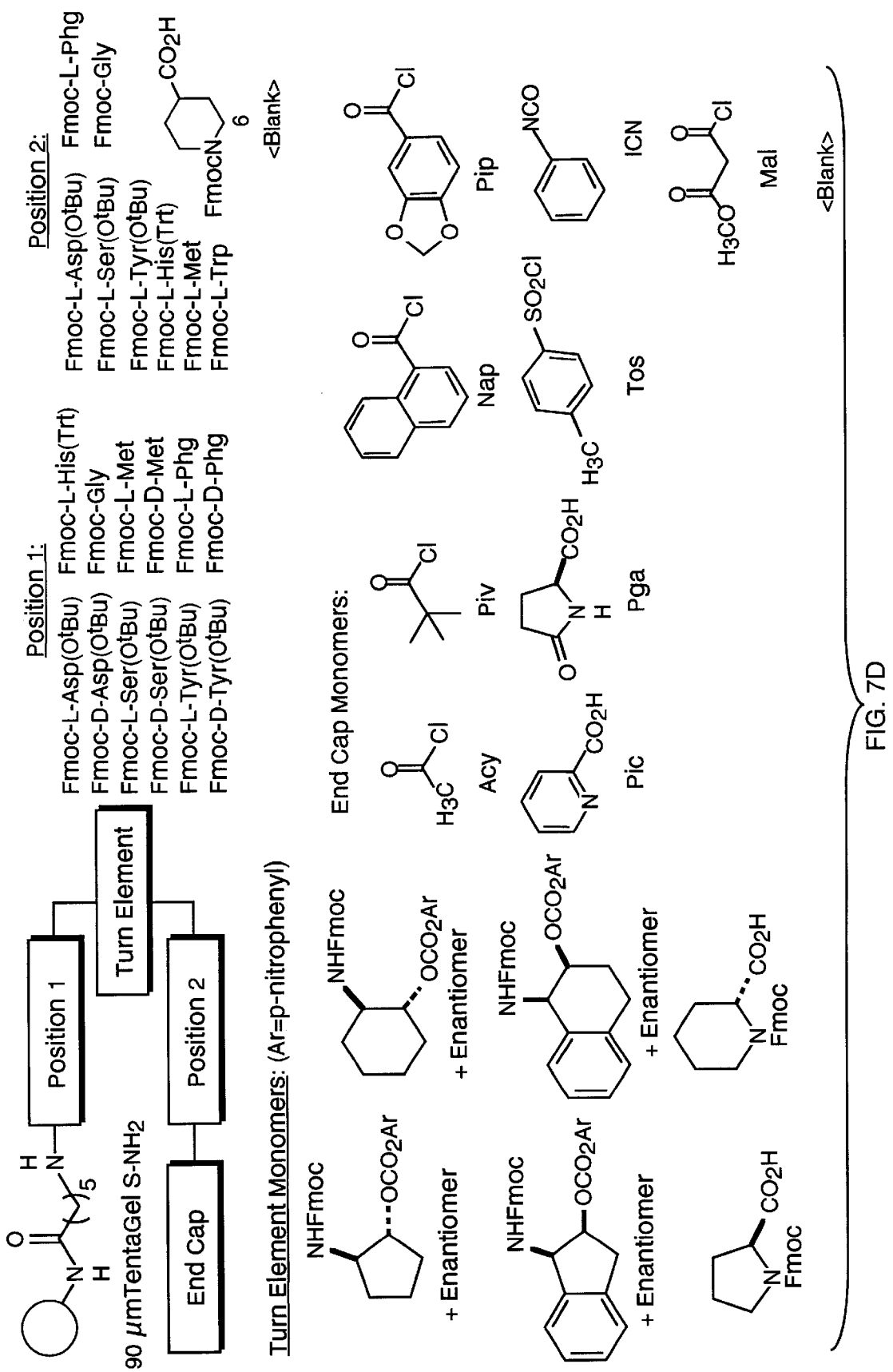

In contrast to the polymer-supported turn elements of the PBM libraries described in Examples 1–5, PBM libraries using "internal" turn elements were also generated. This arrangement is illustrated in FIG. 6 which compares the structure of an $Ni^{2+}$ binder from the PBM libraries described above, with an internal turn element (1-amino-2-indanol) embodiment. The internal turn element maintains the key structural elements for the disposing the metal binding groups in space, but also may permits greater diversity in the selection of turn elements and, in many instances, will be easier to synthesize. FIGS. 7A–7D show the various components used to generate a library of PBMs having an internal turn element format. In particular, the library is variegated by use of multiple different turn elements (FIG. 7A), metal binding groups (FIG. 7B) and end caps (FIG. 7C) so as to produce a library with a potential of 12,000 different variants (FIG. 7D).

Figure 7E:
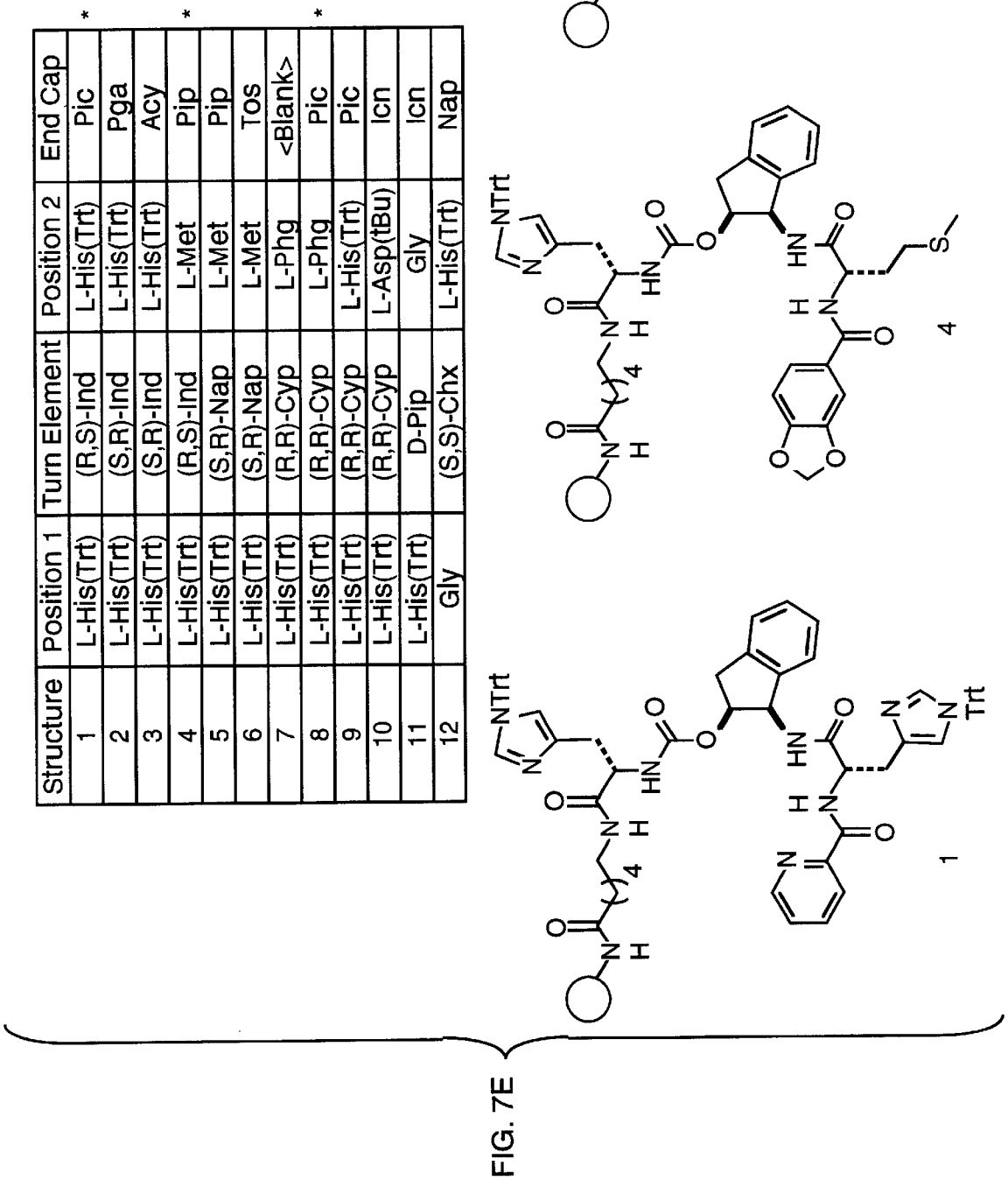
FIG. 7E and FIG. 8 are representative samples of the PBM species which were isolated for $Ni^{2+}$ binding activity.
Figure 8:
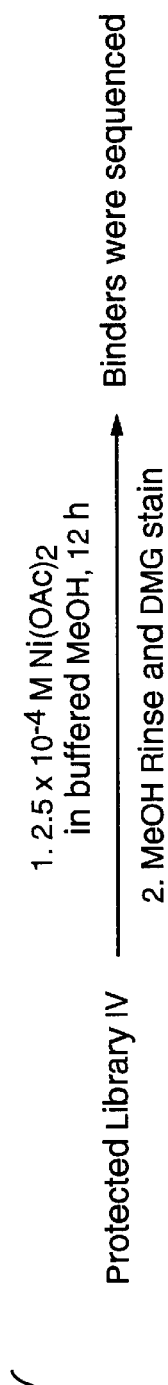
Figure 8:
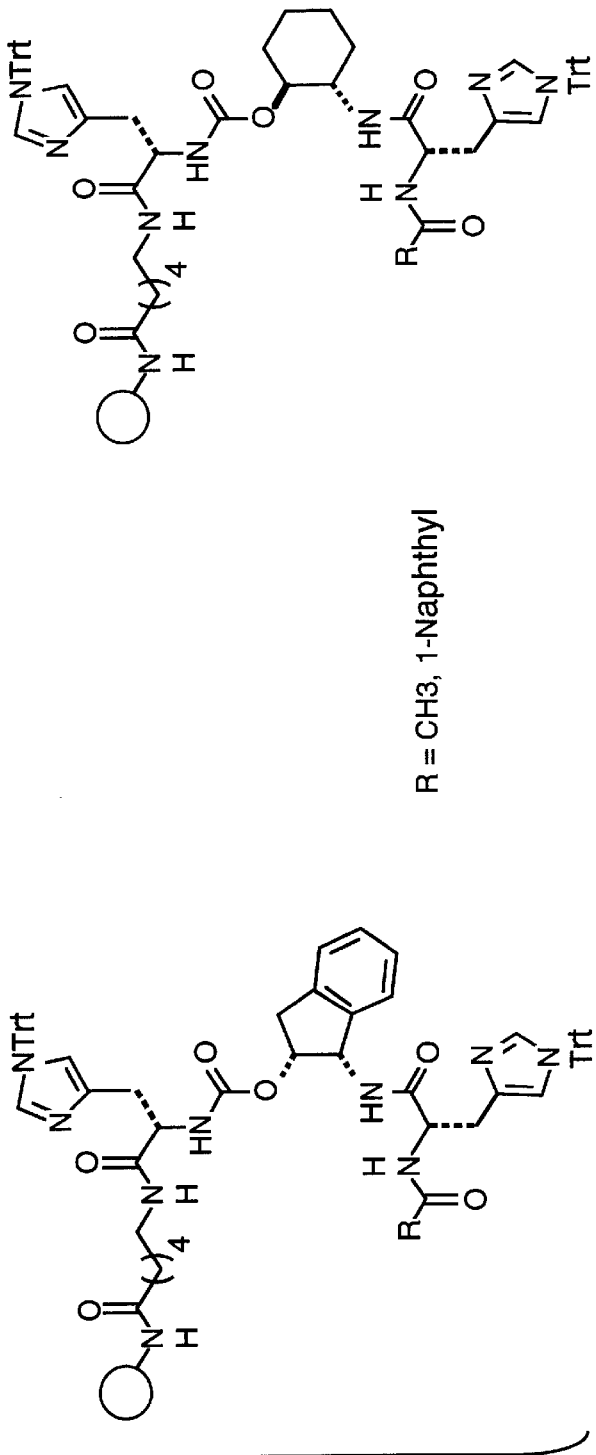

According to the technique described above, the $Ni^{2+}$ binding PBMs were isolated from the library and their identity determined (see FIG. 7E). To further refine our binding assay, e.g., to isolate those $Ni^{2+}$ binding ligands having higher affinity for the metal, the PBM library was treated with a solution having a low concentration $Ni^{2+}$, and the PBMs of the library which could bind under these conditions were isolated and their molecular identity was determined. FIG. 8 illustrates certain convergent tendencies of the library as the criteria for binding affinity are made more strigent.

EXAMPLE 7

Figure 9:
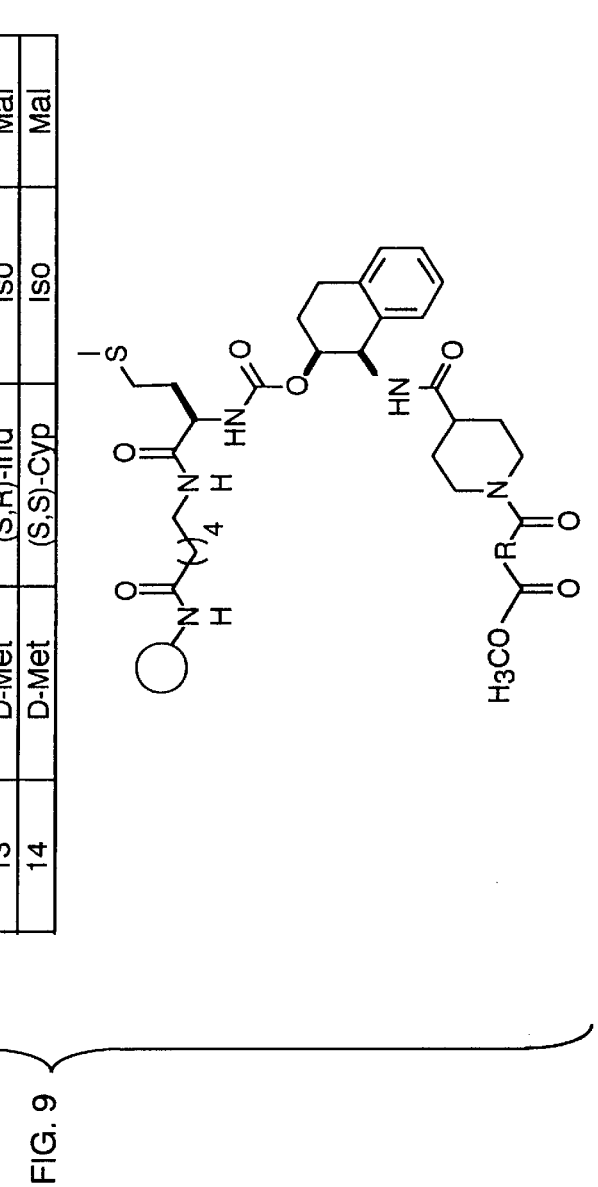
FIG. 9 shows a representative population of Fe(III)-binding ligands isolated from the PBM library of FIG. 7D.

The library described in Example 6 above was also screened for PBMs which could bind to Fe(III) cations. As shown in FIG. 9, PBMs isolated from the library on the basis of their ability to bind the iron cation are of significantly different structure than the nickel binders, and themselves demonstrate a certain convergence in structure and electronic characteristics. This demonstrates the ability of the subject method to not only generate metal ligands, but to generate metal ligands which are selective for different metal ions.

In addition to nickel and iron, we have tested the library of Example 6 against 20 different metal ions, and have found that, with the exception of two metals, the library included PBMs which were able to bind to each metal (see FIG. 10). Our observations also further support the notion that selectivity can be created in the library.

EXAMPLE 8

Figure 11A:
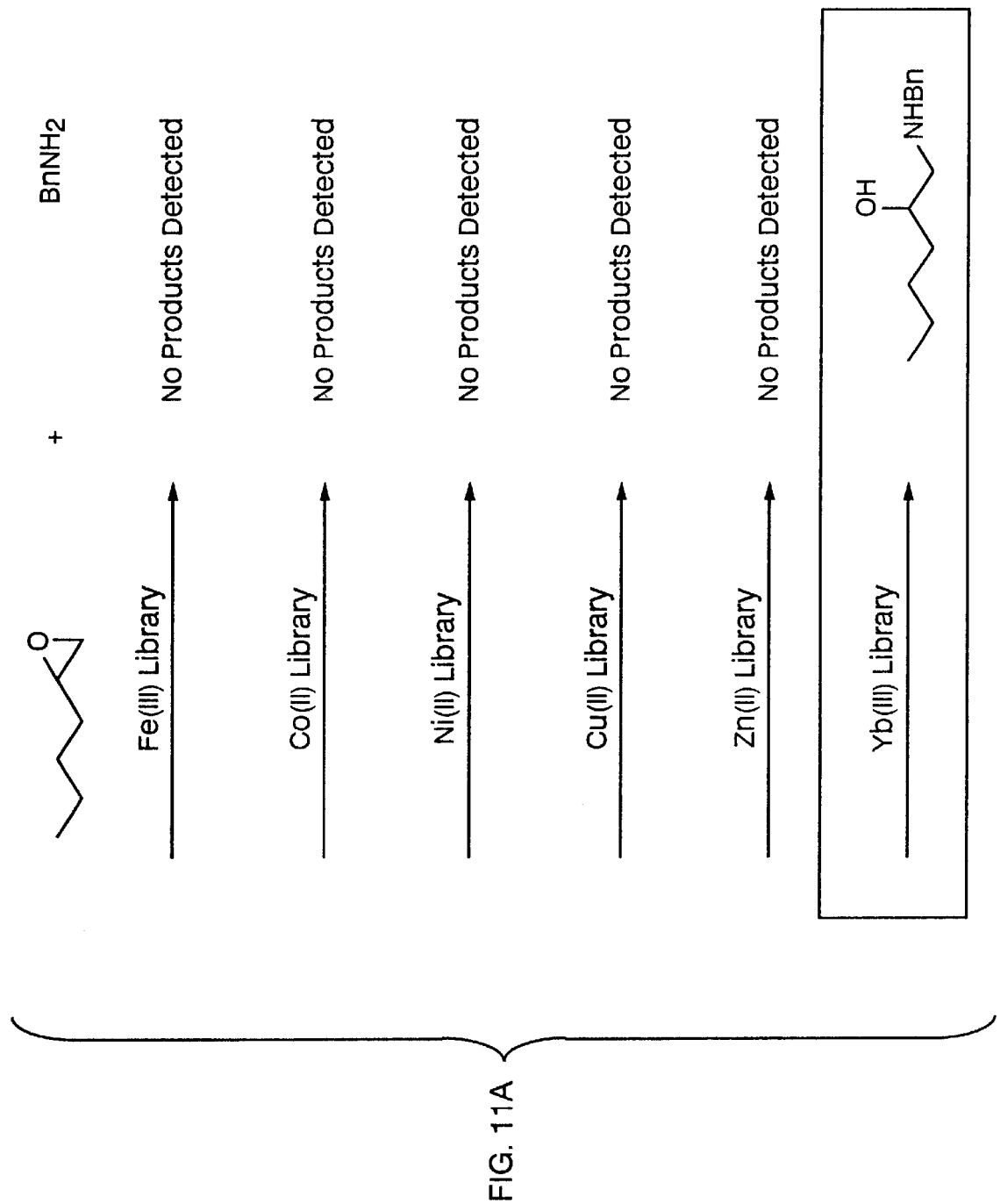
FIGS. 11A–11J illustrate a method for selecting Yb(III) ligands on the basis of the ability to catalyze the synthesis of amino alcohols from epoxides and amines.
Figure 11B:
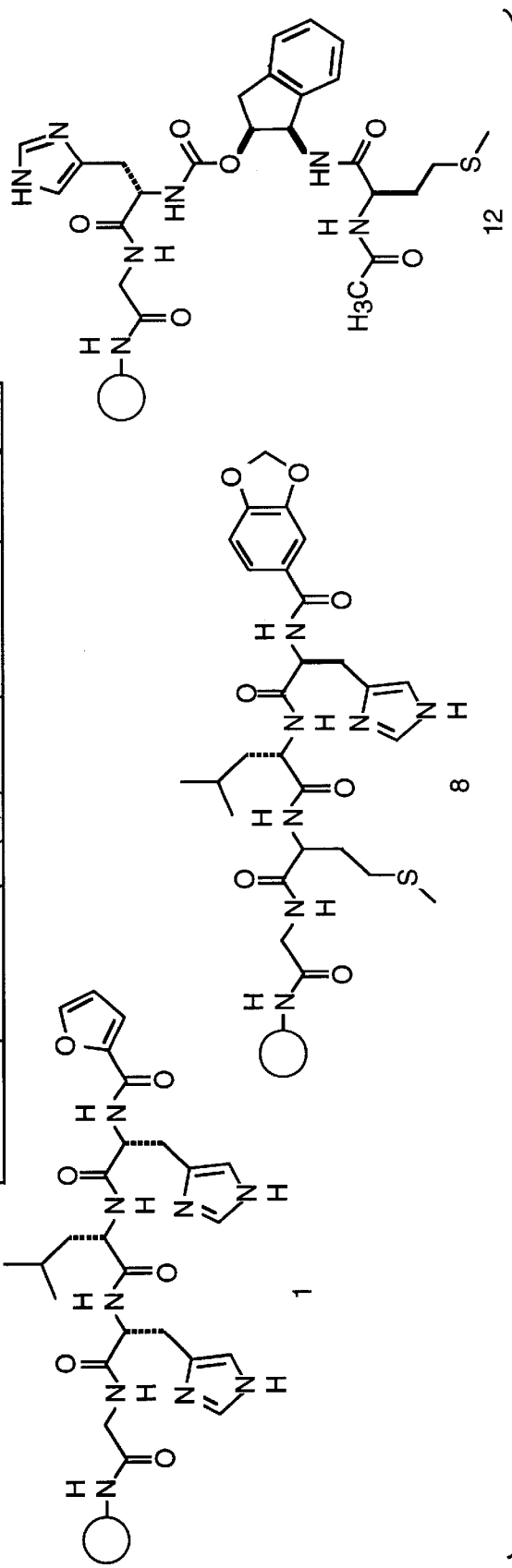

In another exemplary application of the subject method, a PBM-library was screened for metal-ligand combinations optimized for the catalytic synthesis of amino alcohols from epoxides and amines. FIG. 11A illustrates that a library of PBMs were screened in the presence of a variety of different potential metals for metal-ligand pairs capable of catalyzing the synthesis of amino alcohols. Of the 6 different metals tried with the library, only Yb(III) possessed appreciable catalytic activity in the library. The Yitterbium libraries were prepared by admixing, in THF, the combinatorial PBM library with $Yb(OTf)_3$ in the presence of 2,6-lutidine and incubating for 1 hour. In the presence of 2-{[(E)-2-[(2-hydroxyphenyl)imino]ethylidene]amino}phenol and DBU in methanol, the Yb(III) complexes turn red. FIG. 11B shows the identity of certain Yb(III) ligands isolated from the PBM library in this manner.

Figure 11C:
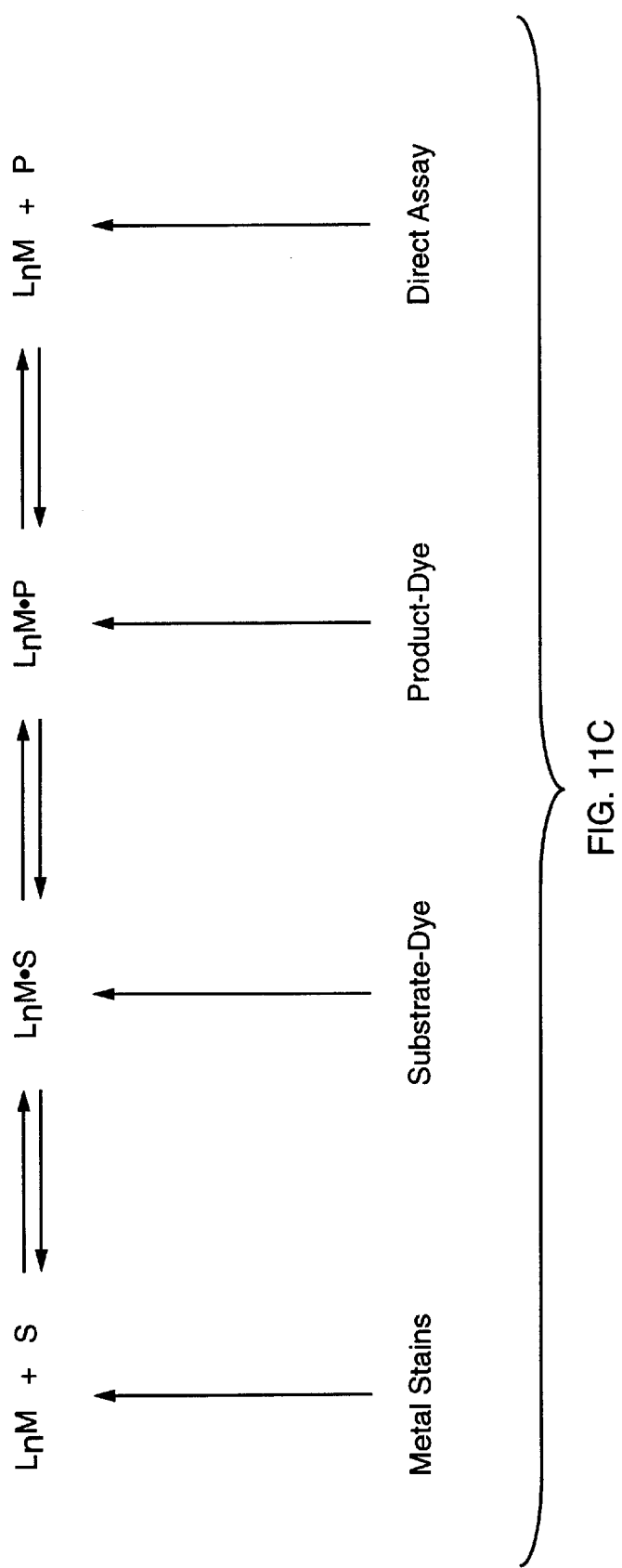
Figure 11D:
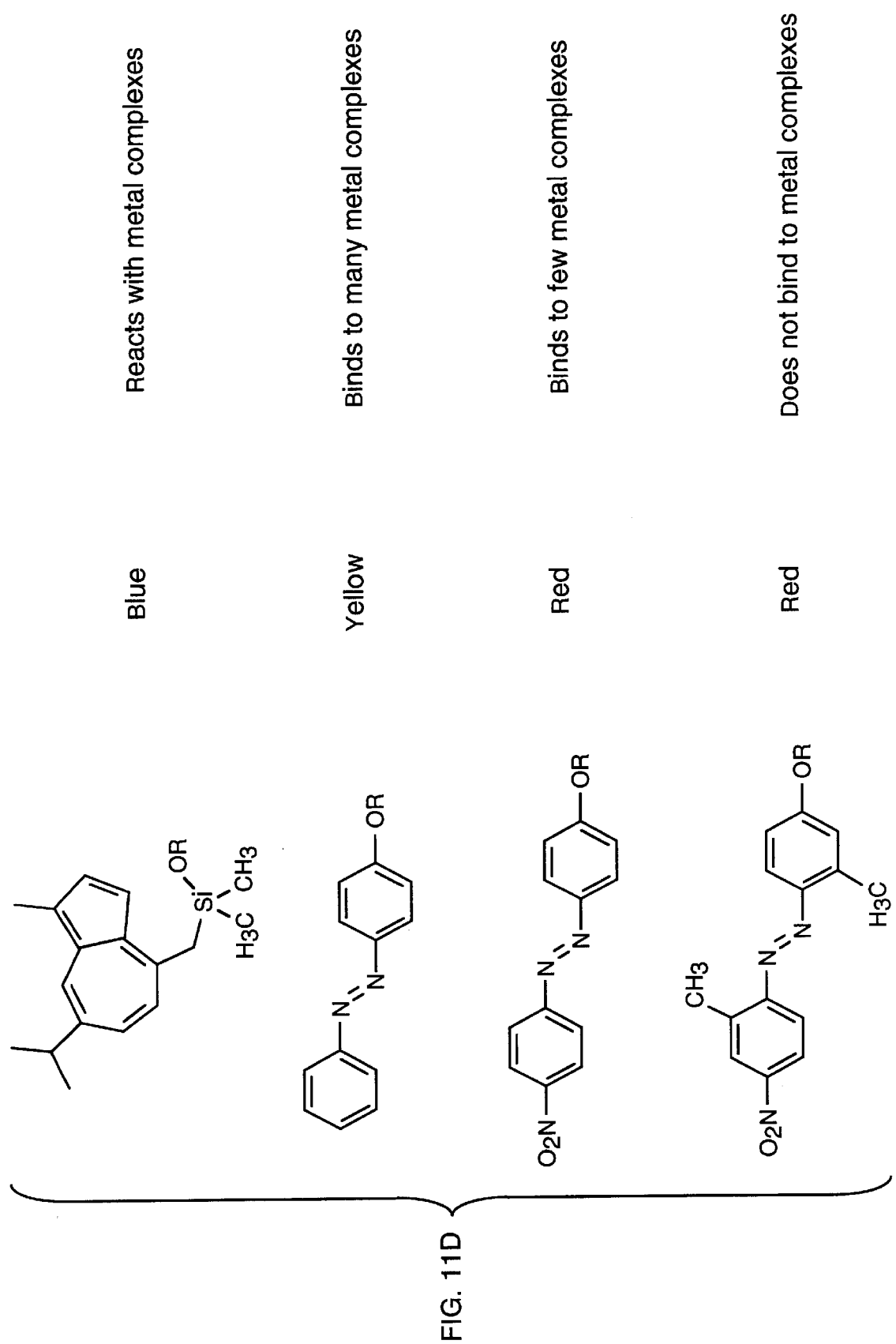
Figure 11E:
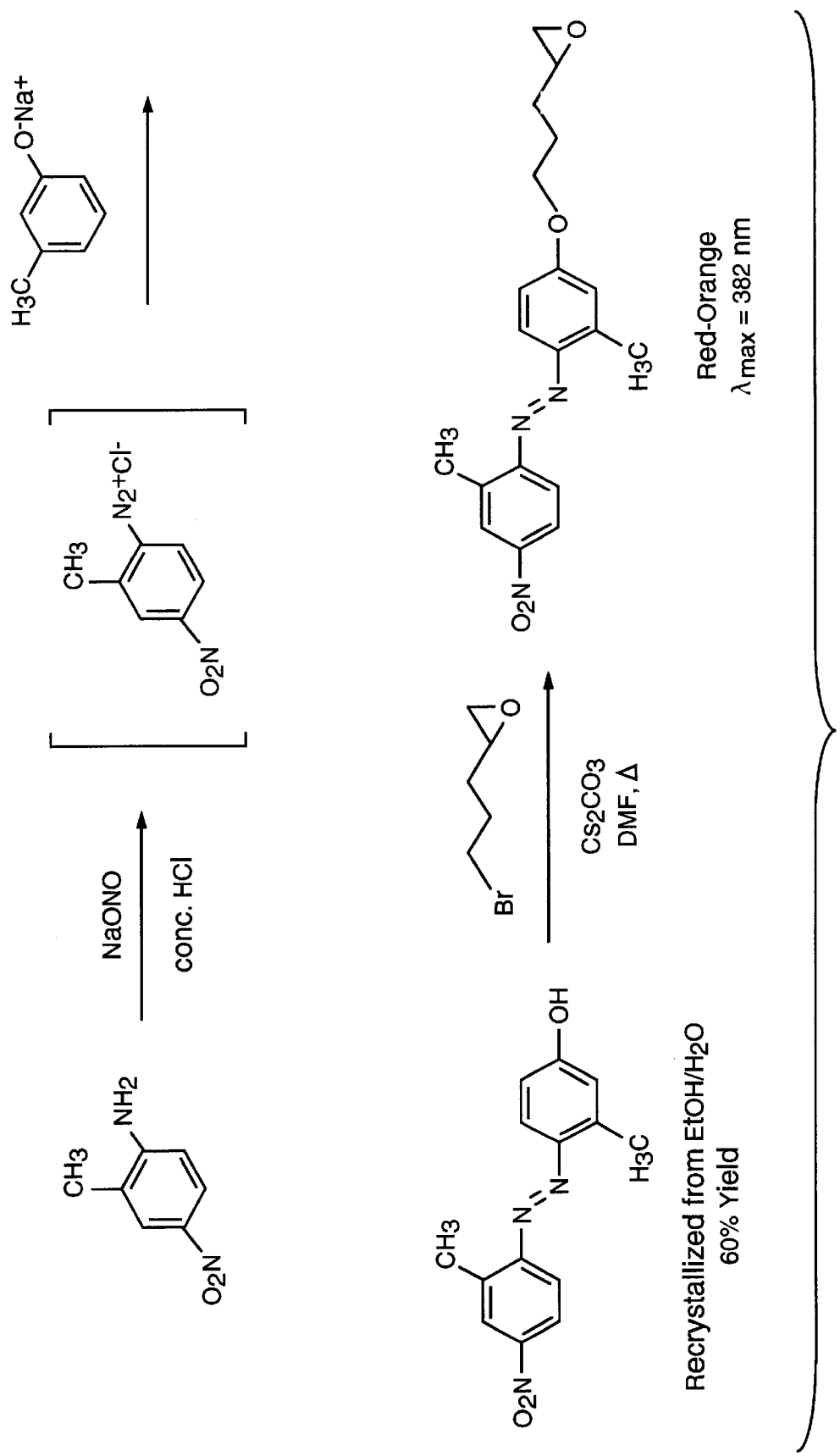
Figure 11F:
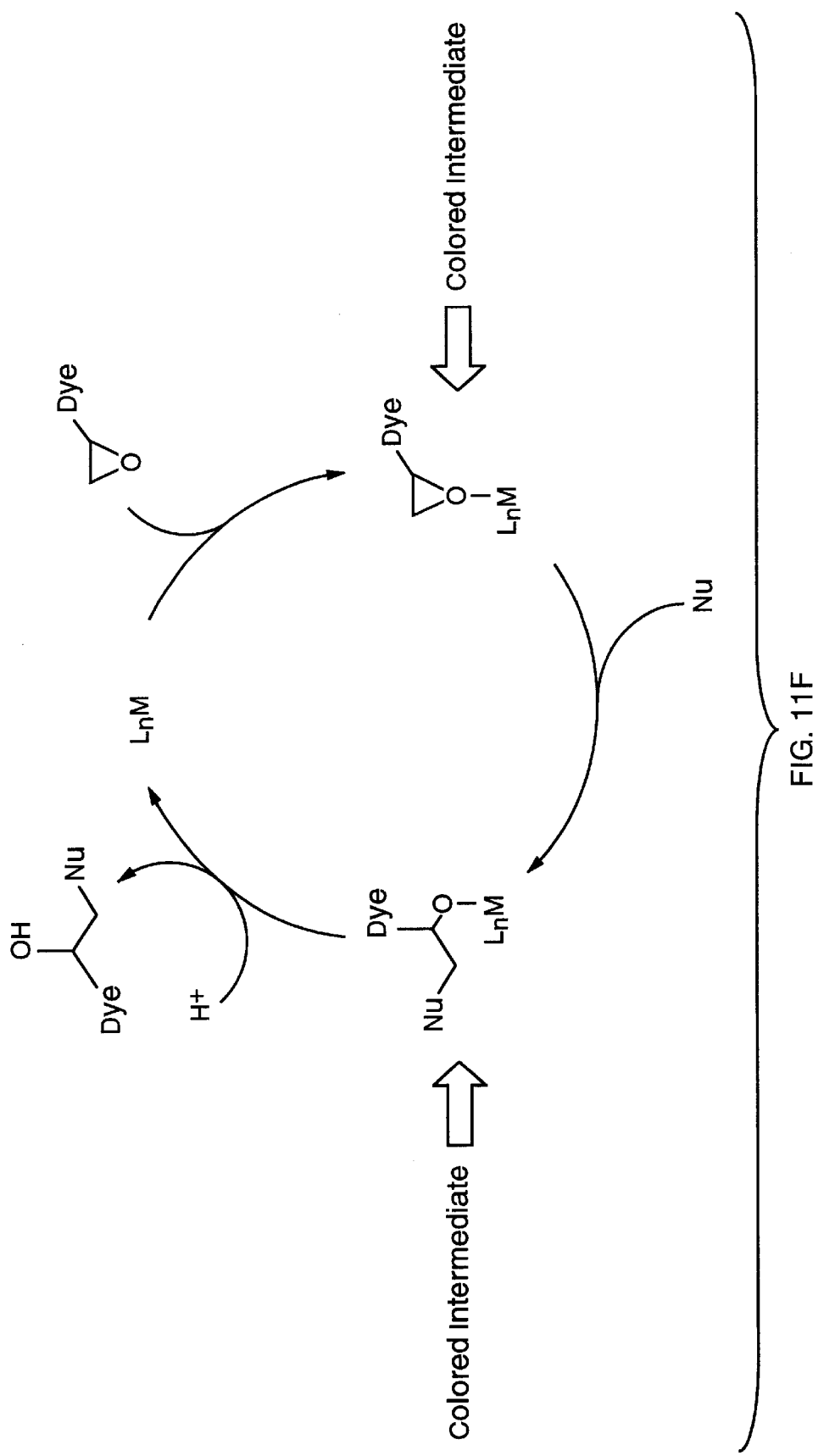
Figure 11G:
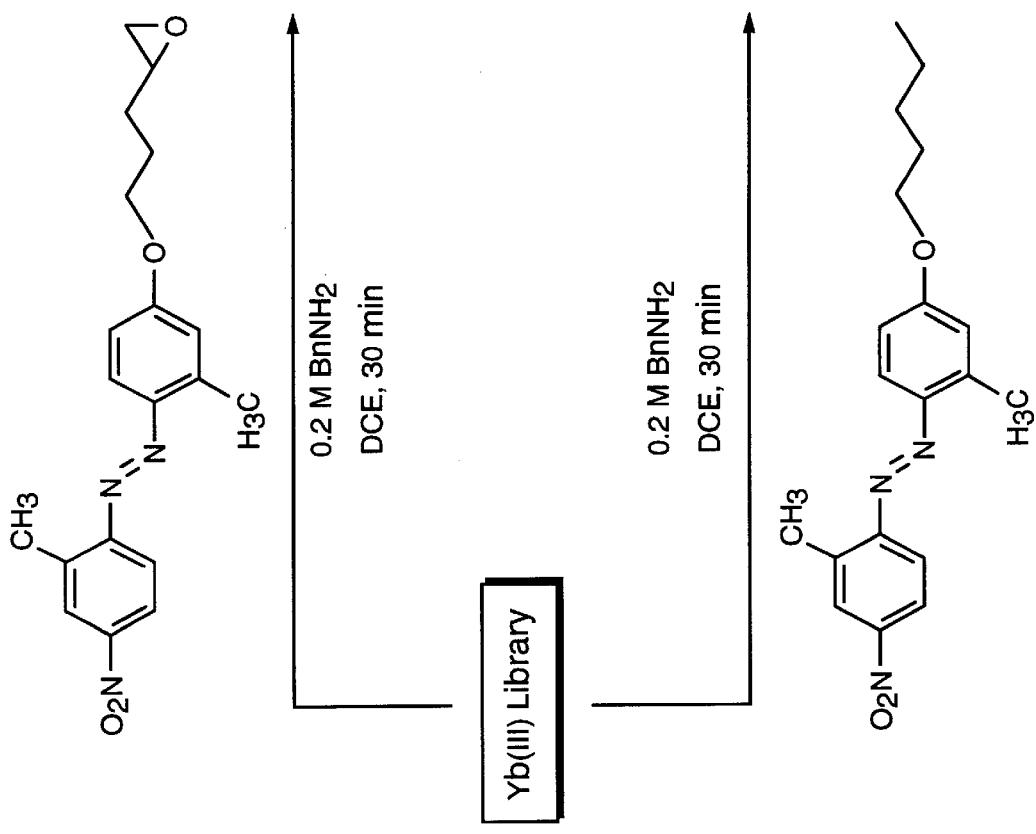
Figure 11H:
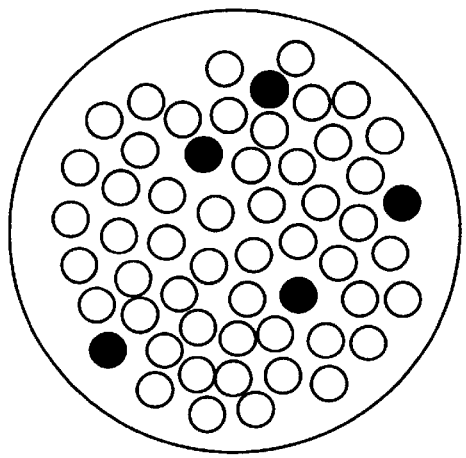
Figure 11H:
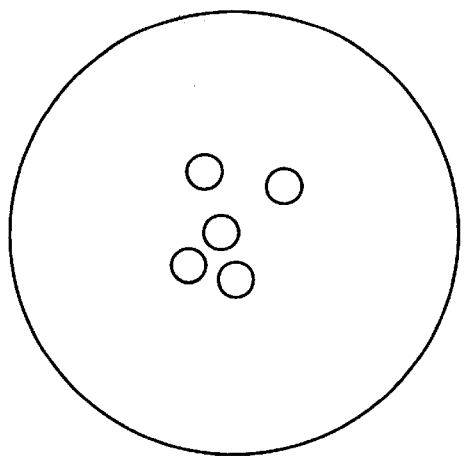
Figure 11H:
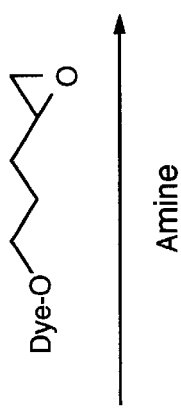
Figure 11H:
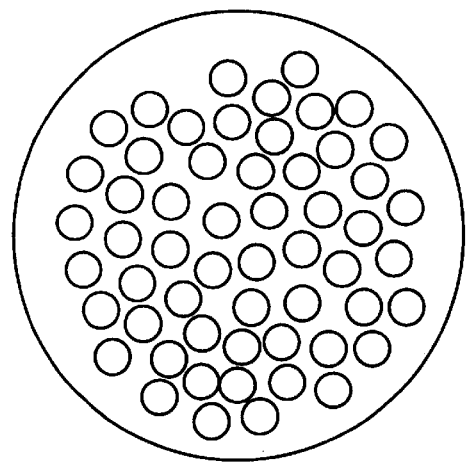
Figure 11H:
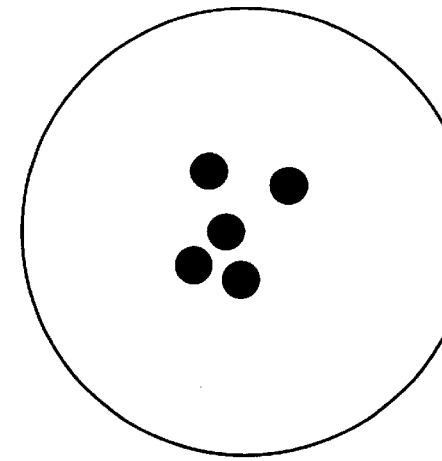
Figure 11I:
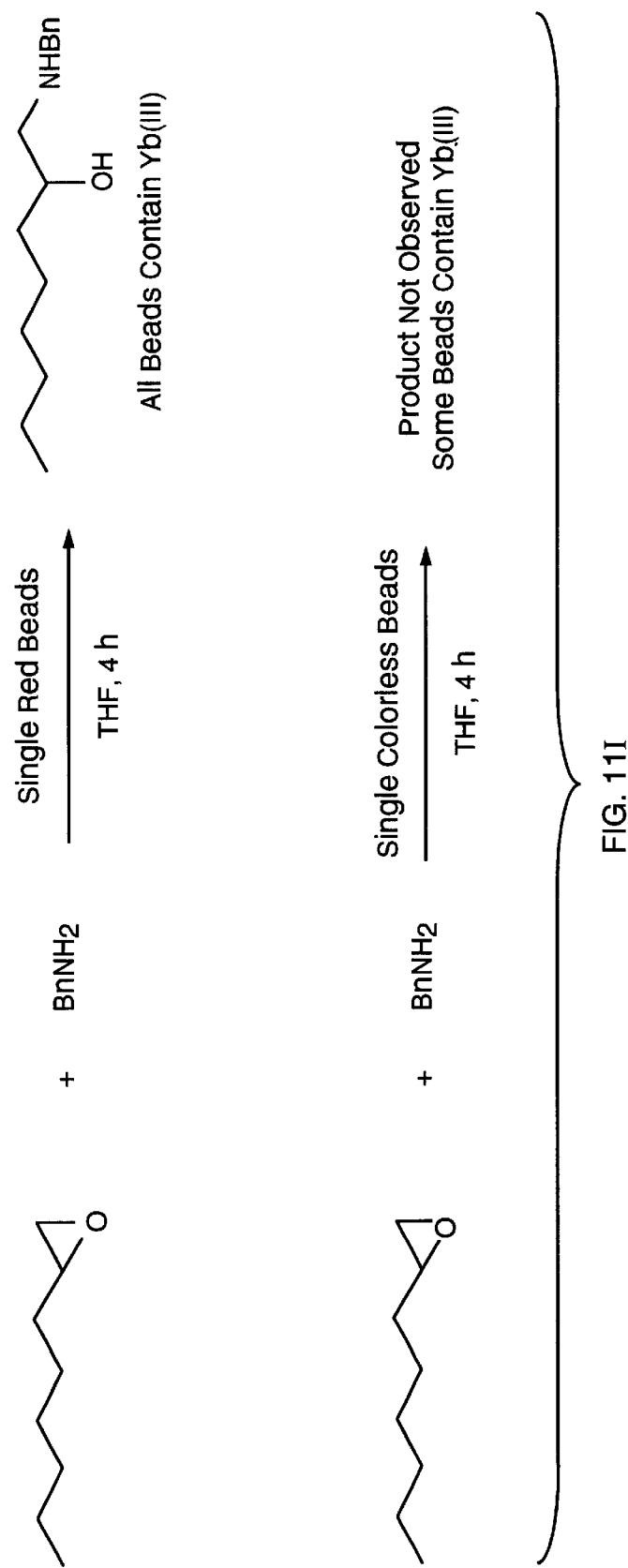
Figure 11J:
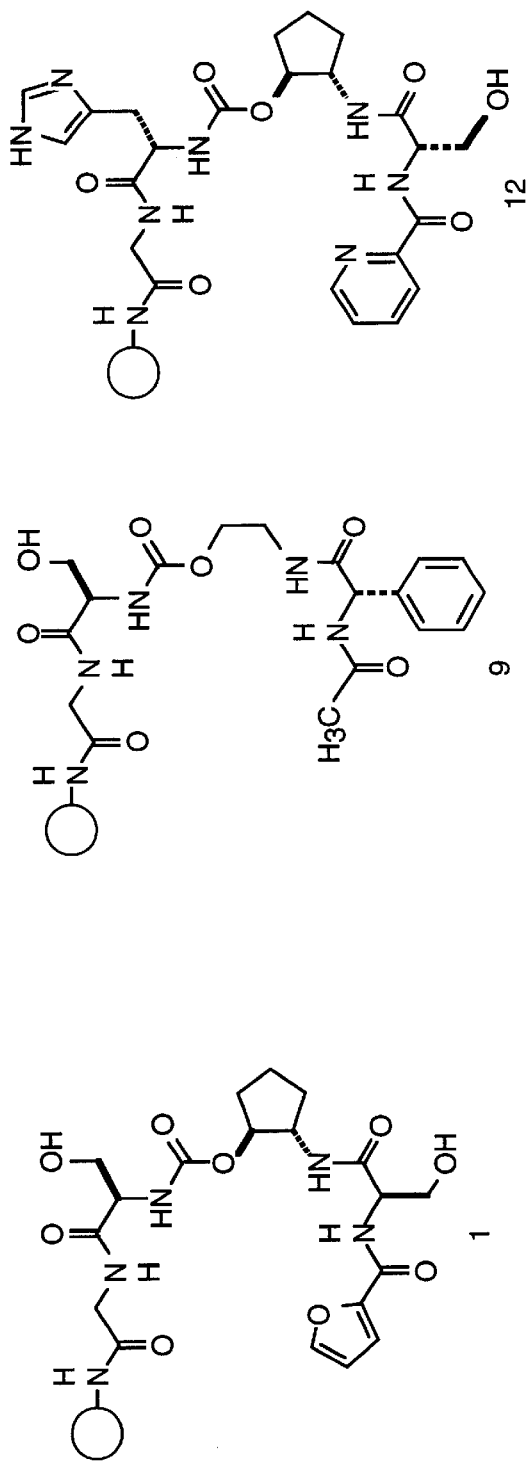

The Yb(III) complexes were then sampled for catalytic activity in the amino alcohol reaction. Briefly, FIG. 11C illustrates several detection techniques for observing this and other catalyzed reactions. As above, the metal-ligand complex can be observed, e.g., with a metal stain. Likewise, dyes sensitive to the substrate or product complex with the metal catalyst can be used to observe these intermediates. Still another means for observing the reaction is to directly assay for the presence of the substrate or products. FIGS. 11D–H outline the generation of an epoxide-dye conjugate which could be used to monitor progress in the synthesis of amino alcohols from epoxides and amines. In particular, this dye was used to isolate PBMs from a bead-linked Yb(III)-PBM library essentially by scoring for the appearance of the colored intermediates. As FIG. 11I illustrates, beads which were selected for because they trapped the epoxide-dye conjugate were found to have PBMs which bound Yb(III). The molecular identity of certain of these PBMs were determined, and each represents a potential novel ligand for Yb(III)-derived metal catalysts.

1. a) *Catalytic Asymmetric Synthesis*; Ojima, I., Ed.: VCH: New York, 1993. b) *Comprehensive Organometallic Chemistry II*; Wilkinson, G.; Stone, F. G. A.; Abel, E. W.; Hegedus, L. S., Eds.; Pergamon: New York, 1995.
2. *Fluorescent Chemosensors for Ion and Molecule Recognition*, Czamik, A. W., Ed.; ACS Symposium Series 538; American Chemical Society: Washington, D.C., 1992.
3. Lippard, S. J.; Berg, J. M. *Principles of Bioinorganic Chemistry*; University Science Books; Mill Valley, Calif., 1994.
4. For recent reviews on strategies for the synthesis of small-molecule libraries, see: a) Thompson, L. A.; Ellman, J. A. *Chem Rev*. 1996, 96, 555. b) Armstrong, R. W.; Combs, A. P.; Tempest, P. A.; Brown, S. D.; Keating, T. A. *Acc. Chem. Res*. 1996, 29, 123. c) Gordon, E. M.; Barrett, R. W.; Dower, W. J.; Fodor, S. P. A.; Gallop, M. A. *J. Med. Chem*. 1994, 37, 1385.
5. For combinatorial approaches to the study of ligand-receptor interactions, see: a) Still, W. C. *Acc. Chem. Res*. 1996, 29, 155, and references therein. b) Yu, H.; Chen, J. K.; Feng, S.; Dalgarno, D. C.; Brauer, A. W.; Schreiber, S. L. *Cell* 1994, 76, 933. c) Combs, A. P.; Kapoor, T. M.; Feng, S.; Chen, J. K.; Daude-Snow, L. F.; Schreiber, S. L. *J. Am. Chem. Soc*. 1996, 118, 287. d) Zuckermann, R. N. et al. *J. Med. Chem*. 1994, 37, 2678. e) Wang, G. T.; Li, S.; Wideburg, N.; Kraffi, G. A.; Kempf, D. J. *J. Med. Chem*. 1995, 38, 2995. f) Campbell, D. A.; Bermak, J. C.; Burkoth, T. S.; Patel, D. V. *J. Am. Chem. Soc*. 1995, 117, 5381.
6. Spatially addressed synthetic libraries have been applied with success for the identification of metal-containing solid-state materials. (Briceno, G.; Chang, H.; Sun, X.; Schultz, P. G.; Xiang, X. D. *Science* 1995, 270, 273), 99mTc-binding peptides a(Malin, R.; J. Schneider-Mergenet et al. *J. Am. Chem. Soc*. 1995, 117, 11821), and selective catalysts (Burgess, K.; Lim, H. J.; Porte, A. M.; Sulikowski, G. A. Angew. *Chem. Int. Ed. Engl*. 1996, 35, 220).
7. Burger, M. T.; Still, W. C. *J. Org. Chem*. 1995, 60, 7382.
8. Experimental procedures for the synthesis of the library and its components are provided as supporting information.

9. Furka, A.; Sebestyen, F.; Asgedom, M.; Dibo, G. *Int. J. Peptide Protein Res.* 1991, 37, 487.
10. Ohlmeyer, M. H. J.; Swanson, R. N.; Dillard, L. W.; Reader, J. C.; Asouline, G.; Kobayashi, R.; Wigler, M.; Still, W. C. *Proc. Natl. Acad. Sci. U.S.A.* 1993, 90, 10922.
11. Equilibration experiments have shown the binding of Ni(II) to be reversible under these conditions.
12. A sample of 24,000 beads, or 2.0 copies of the library, assures that 95% of the ligands are represented with 99% confidence. Burgess, K.; Liaw, A. I.; Wang, N. *J. Med. Chem.* 1994, 37, 2985.
13. Binding experiments carried out 3 times using [Ni(OAc)2]=2.5×10$^{-4}$M and at a variety of higher Ni concentrations led to the identification of 16 and 17 as ligands in every case.
14. For both 16•Ni and 17•Ni. the predominant species corresponds to a 1:1 complex of Ni(II) and doubly-deprotonated ligand (NiLHn-2). Several other hits from this binding screen have been resynthesized on solid phase for binding confirmation. Experiments to determine the association constants of these complexes are underway and will be reported in due course.
15. In all cases, control experiments revealed no measurable metal ion binding to the untreated beads. The structures of representative ligands for each of these metals are provided in the supplementary material.

All of the above-cited references and publications are hereby incorporated by reference.

Equivalents

Those skilled in the art will recognize, or be able to ascertain using no more than routine experimentation, numerous equivalents to the specific polypeptides, nucleic acids, methods, assays and reagents described herein. Such equivalents are considered to be within the scope of this invention.

We claim:

1. A method for identifying a chelating agent for a metal or metal ion, comprising
    (a) chemically synthesizing a variegated library of potential binding moieties (PBMs) from a variegated assortment of metal binding groups (MBGs) bearing Lewis basic atoms and turn elements, the PBMs of the PBM library having at least one turn element substituted twice with MBGs;
    (b) screening compounds obtained in step (a) for metal binding activity; and
    (c) isolating PBMs from the PBM library on the basis of ability to bind to a metal or metal ion;

wherein said turn elements are independently selected from the group consisting of:

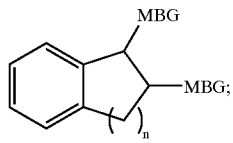

A

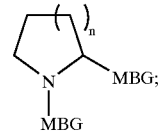

B

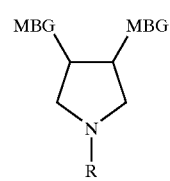

C wherein
R represents a link to a sold support; and
n is independently 1 or 2; and
wherein said metal binding groups comprise amino acids with the following proviso:
in structures A and B one MBG is part of a link to a solid support and the other comprises a protected amino acid; and in structure C both MBGs comprise protected amino acids.

2. The method of claim 1, wherein at least one turn element provided in the PBM library is a chiral turn element.

3. The method of claim 1, wherein screening compounds includes testing the ability of compounds to bind a transition metal.

4. The method of claim 1, wherein screening compounds includes testing the ability of compounds to bind a Lanthanide metal.

5. The method of claim 1, wherein screening compounds includes testing the ability of compounds to bind a metal selected from $Co^{3+}$, $Cr^{3+}$, $Hg^{2+}$, $Pd^{2+}$, $Pt^{2+}$, $Pd^{4+}$, $Pt^{4+}$, $Rh^{3+}$, $Ir^{3+}$, $Ru^{3+}$, $Co^{2+}$, $Ni^{2+}$, $Cu^{2+}$, $Zn^{2+}$, $Cd^{2+}$, $Pb^{2+}$, $Mn^{2+}$, $Fe^{3+}$, $Fe^{2+}$, $Au^{3+}$, $Au^+$, $Ag^+$, $Cu^+$, $MoO_2^{2+}$, $Ti^{3+}$, $Ti^{4+}$, $Bi^{3+}$, $CH_3Hg^+$, $Al^{3+}$, $Ga^{3+}$, $Ce^{3+}$, $UO_2^{2+}$, $Yb^{3+}$, and $La^{3+}$.

* * * * *

UNITED STATES PATENT AND TRADEMARK OFFICE
CERTIFICATE OF CORRECTION

PATENT NO. : 6,489,093 B1
DATED : December 3, 2002
INVENTOR(S) : Jacobsen, E.N. et al.

It is certified that error appears in the above-identified patent and that said Letters Patent is hereby corrected as shown below:

Column 1,
Line 11, replace "GM136639" with -- GM16639 --.

Signed and Sealed this

Twenty-fifth Day of February, 2003

JAMES E. ROGAN
*Director of the United States Patent and Trademark Office*